United States Patent
Blelloch et al.

(10) Patent No.: US 9,353,352 B2
(45) Date of Patent: May 31, 2016

(54) EMBRYONIC STEM CELL SPECIFIC MICRORNAS PROMOTE INDUCED PLURIPOTENCY

(71) Applicant: THE REGENTS OF THE UNIVERSITY OF CALIFORNIA, Oakland, CA (US)

(72) Inventors: Robert Blelloch, San Francisco, CA (US); Robert Laird Judson, San Francisco, CA (US); Collin Alfred Melton, San Francisco, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 14/472,987

(22) Filed: Aug. 29, 2014

(65) Prior Publication Data

US 2015/0024486 A1    Jan. 22, 2015

Related U.S. Application Data

(62) Division of application No. 13/260,904, filed as application No. PCT/US2010/029699 on Apr. 1, 2010, now Pat. No. 8,852,940.

(60) Provisional application No. 61/165,865, filed on Apr. 1, 2009.

(51) Int. Cl.
| | |
|---|---|
| *C12N 5/074* | (2010.01) |
| *C12N 5/0735* | (2010.01) |
| *C12N 7/00* | (2006.01) |
| *C12N 15/00* | (2006.01) |
| *A61K 35/545* | (2015.01) |
| *C12N 15/11* | (2006.01) |

(52) U.S. Cl.
CPC ............ *C12N 5/0696* (2013.01); *A61K 35/545* (2013.01); *C12N 15/111* (2013.01); *C12N 2310/141* (2013.01); *C12N 2320/30* (2013.01); *C12N 2501/602* (2013.01); *C12N 2501/603* (2013.01); *C12N 2501/604* (2013.01); *C12N 2501/65* (2013.01); *C12N 2510/00* (2013.01)

(58) Field of Classification Search
CPC ............... C12N 5/0696; C12N 15/111; C12N 2310/141; C12N 2320/30; C12N 2501/602; C12N 2501/603; C12N 2501/604; C12N 2501/65; C12N 2510/00; A61K 35/545
See application file for complete search history.

(56) References Cited

U.S. PATENT DOCUMENTS

| | | | |
|---|---|---|---|
| 2008/0050722 A1 | 2/2008 | Kim et al. | |
| 2009/0047263 A1* | 2/2009 | Yamanaka et al. | ......... 424/93.21 |
| 2010/0075421 A1 | 3/2010 | Yamanaka et al. | |
| 2010/0221266 A1* | 9/2010 | Gregory et al. | ............ 424/174.1 |

OTHER PUBLICATIONS

Pillai et al., Science, 309: 1573-1576, 2005.*
U.S. Appl. No. 60/996,893, filed Dec. 10, 2007.
Babiarz, Joshua E. et al., "Small RNAs—their biogenesis, regulation and function in embryonic stem cells," (May 31, 2009), *StemBook*, ed. The Stem Cell Research Community, StemBook, doi/10.3824/stembook.1.47.1, http://www.stembook.org.
Judson, Robert L. et al., "Embryonic stem cell specific microRNAs promote induced pluripotency", *Nature Biotechnology* 27(5):459-461 (2009).
Lin, Shi-Lung et al., "Mir-302 reprograms human skin cancer cells into a pluripotent ES-cell-like state," *RNA*, vol. 14, pp. 2115-2124 (2008).
Melton, Collin et al., "Opposing microRNA families regulate self-renewal in mouse embryonic stem cells," (Feb. 4, 2010), *Nature* vol. 463, No. 7281, pp. 621-626 (2010).
Nakagawa, Masato et al., "Generation of induced pluripotent stem cells without Myc from mouse and human fibroblasts," (Jan. 2008), *Nature Biotechnology*, vol. 26, No. 1, pp. 101-106. (2006).
Zhang, Baohong et al., "MicroRNA: A New Player in Stem Cells", (2006), *Journal of Cellular Physiology* 209:266-269.
Takahashi et al., Induction of Pluripotent Stem Cells from Mouse Embryonic and Adult Fibroblast Cultures by Defined Factors, *Cell*, vol. 126, pp. 663-676 (2006).
Baker, "MicroRNAs boost regrogramming, boot out cMyc", *Nature Reports Stems Cells*, pp. 1-3 (2009), accessed online on Jan. 6, 2014.
Wang et al., "MiR-294/-302 promotes proliferation, suppresses G1-S restriction point, and inhibits embryonic stem cell differentiation through separable mechanisms", *Cell Rep.*, vol. 4, No. 1, pp. 99-109 (2013).

* cited by examiner

*Primary Examiner* — Thaian N Ton
(74) *Attorney, Agent, or Firm* — Kilpatrick Townsend & Stockton LLP

(57) ABSTRACT

The methods of the present application describe that introduction of physiologically relevant miRNAs can enhance or modulate somatic cell reprogramming, generating induced pluripotent stem cells (iPS cells). These miRNAs did not further enhance reprogramming in the presence of cMyc. Furthermore, unlike previously described methods of generating iPS cells, such as through the introduction of genetic elements using viruses, the methods of the present invention reduce the risk of activating oncogenes in the iPS cells. The methods of the invention generate iPS cells that can be free of genetic modifications and thus have greater potential for use as therapeutic agents than those generated by existing methods.

11 Claims, 22 Drawing Sheets

| C Cell Lines | Mice Injected | Teratomas Formed | Teratomas Invasive | Day Post-injected Collected | Percent Teratoma | Percent Invasive |
|---|---|---|---|---|---|---|
| V6.5 | 6 | 10 | 0 | 1x15, 4x31, 1x55 | 100 | 0 |
| OSK+Myc | | | | | | |
| 10-4 | 1 | 2 | 0 | 24 | | |
| 10-5 | 1 | 2 | 1 | 15 | | |
| 10-6 | 1 | 2 | 1 | 24 | | |
| 12-2 | 2 | 3 | 0 | 31 | 78 | 43 |
| 12-3 | 3 | 4 | 1 | 31 | | |
| 12-4 | 1 | 0 | 0 | 31 | | |
| 12-5 | 1 | 0 | 0 | 31 | | |
| 14-1 | 1 | 1 | 0 | 31 | | |
| 14-2 | 1 | 1 | 0 | 31 | | |
| OSK+294 | | | | | | |
| 10-1 | 1 | 2 | 0 | 31 | | |
| 10-2 | 1 | 2 | 0 | 31 | | |
| 10-3 | 1 | 2 | 0 | 31 | | |
| 12-19 | 2 | 3 | 0 | 31 | 100 | 0 |
| 12-20 | 2 | 1 | 0 | 31 | | |
| 12-21 | 2 | 2 | 0 | 31 | | |
| 12-22 | 2 | 3 | 0 | 15 | | |
| 12-23 | 1 | 1 | 0 | 15 | | |

EMBRYONIC STEM CELL SPECIFIC MICRORNAS PROMOTE INDUCED PLURIPOTENCY

CROSS-REFERENCES TO RELATED APPLICATIONS

This application is a divisional application of U.S. application Ser. No. 13/260,904, filed Apr. 1, 2010, which claims priority to U.S. Provisional Application No. 61/165,865, filed Apr. 1, 2009, the contents of which are incorporated herein by reference in their entirety for all purposes.

STATEMENT AS TO RIGHTS TO INVENTIONS MADE UNDER FEDERALLY SPONSORED RESEARCH AND DEVELOPMENT

This invention was made with government support under grant nos. NS057221 and NS048118 awarded by the National Institutes of Health. The government has certain rights in the invention.

REFERENCE TO A "SEQUENCE LISTING," A TABLE, OR A COMPUTER PROGRAM LISTING APPENDIX SUBMITTED ON A COMPACT DISK

The Sequence Listing written in file "Sequence Listing 81906-912674.TXT" created on Aug. 29, 2014, 61,440 bytes, machine format IBM-PC, MS-Window operating system, is hereby incorporated by reference in its entirety for all purposes.

FIELD OF THE INVENTION

The present invention relates to development of a method for making induced pluripotent stem (iPS) cells by introducing microRNAs (miRNAs) into somatic cells. In some embodiments, the somatic cells are either adult or embryonic, mouse or human, fibroblasts. Unlike previously described methods of generating iPS cells, such as through the introduction of genetic elements using viruses, the methods of the present invention reduce the risk of activating oncogenes in the iPS cells. The methods of the invention can create iPS cells that lack at least one genetic modification, or are free of genetic modifications, and thus have greater potential for use as therapeutic agents than those generated by existing methods.

Mammalian development follows a carefully orchestrated unfolding of cell fate transitions leading to a complex set of highly specialized cell types. These cell fate transitions involve the silencing of previously active molecular programs along with the activation of new ones. MiRNAs are small non-coding RNAs that are well suited to suppress previously active programs and, thereby, provide robustness to cell fate decisions (Babiarz, J. E. & Blelloch, R. Small RNAs—their biogenesis, regulation and function in embryonic stem cells. StemBook, ed. The Stem Cell Research Community, StemBook, doi/10.3824/stembook. 1.47.1. (2009). Hornstein, E. & Shomron, N. Canalization of development by microRNAs. *Nat. Genet* 38, S20-24 (2006). MiRNAs identify their targets via base pairing of nucleotides 2-8 of the miRNA (the seed sequence) with complementary sequences within the target mRNA's open reading frame (ORF) and 3' untranslated region (UTR) (The Stem Cell Research Community, StemBook, doi/10.3824/stembook. 1.47.1. (2009)). This targeting is carried out in coordination with the RNA-induced silencing complex (RISC) and often results in both destabilization and translational inhibition of the targets. While inhibition of any one target is usually only partial, each miRNA binds and suppresses hundreds of mRNA targets, resulting in large overall changes in the molecular constitution of cells.

BACKGROUND OF THE INVENTION

Differentiated cells are capable of being reprogrammed to an embryonic-like state by transfer of nuclear contents into oocytes or by fusion with embryonic stem (ES) cells. Additionally, studies have shown that mouse embryonic or adult fibroblasts can be induced to become pluripotent cells by using retroviral vectors to induce expression of four factors: Oct3/4, Sox2, c-Myc and Klf3. These induced cells are termed induced pluripotent stem cells (iPS). The iPS cells exhibit the morphology and growth properties of ES cells and express ES cell maker genes. Upon injection into nude mice these cells form tumors, severely limiting their potential use as therapeutic agents. (See, e.g., Takahashi, K. and Yamanaka, S., Induction of Pluripotent Stem Cells from mouse Embryonic and Adult Fibroblast Cultures by Defined Factors, Cell, 126:663-676 (2006)).

MicroRNAs (miRNAs) are single-stranded RNA molecules, typically between 21 and 23 nucleotides in length. They are endogenously occurring, untranslated RNA molecules involved in regulation of gene expression. miRNAs are also important regulators of development and differentiation. (See, e.g., Suh, et al., Human embryonic stem cells express a unique set of microRNAs, Developmental biology, 270:488-498 (2004). miRNAs function to regulate gene expression through targeting mRNAs for cleavage or translation repression. (See, e.g., Bartel, D. P., *MicroRNAs: Genomics, Biogenesis, Mechanism, and Function* Cell 116:281-297 (2004).) At present, nearly all of the identified miRNAs are conserved in closely related animals, such as humans and mouse. (See, e.g., Lagos-Quintana et al., *New microRNAs from mouse and human* RNA 9:175-179 (2003); Lim et al., *Vertebrate microRNA genes* Science 299:1540 (2003)).

One microRNA cluster, designated the miR-290 cluster, constitutes over 70% of the entire miRNA population in mouse ES cells (Marson, A. et al. *Connecting microRNA genes to the core transcriptional regulatory circuitry of embryonic stem cells* Cell 134:521-533 (2008)). Expression of the miR-290 cluster is rapidly down-regulated upon ES cell differentiation (See, e.g., Houbaviy, H. B., Murray, M. F. & Sharp, P. A. *Embryonic stem cell-specific MicroRNAs Dev Cell* 5:351-358 (2003)). A subset of the miR-290 cluster, called the embryonic stem cell cycle (ESCC) regulating miRNAs, enhances the unique stem cell cycle and includes miR-291-3p, miR-294, and miR-295, as well as the human homologues hsa-mir-302a, hsa-miR-302b, hsa-miR-302c, hsa-miR-302d, hsa-miR-371-5p, hsa-miR-372, hsa-miR-373. (See, e.g., Wang, Y. et al. *Embryonic stem cell-specific microRNAs regulate the G1-S transition and promote rapid proliferation* Nat Genet 40:1478-1483 (2008)). This subset includes miR-291-3p, miR-294, and miR-295 and their homologues.

Removal of genes required for maturation of all miRNAs has shown that miRNAs play essential roles in the proliferation and differentiation of Embryonic Stem Cells (ESCs) (Wang, Y. et al., *Nat Genet* 39:380-5 (2007); Kanellopoulou, C. et al. *Genes Dev* 19:489-501 (2005); Murchison, E. P. et al., *Proc Natl Acad Sci USA* 102:12135-40 (2005)). For example, the loss of the RNA binding protein DGCR8, which is required for the production of all canonical miRNAs, results in a cell cycle defect and an inability to silence the self-renewal program of ESCs when they are placed in differentiation-inducing conditions (Wang, Y. et al., *Nat Genet* 39:380-5 (2007). The introduction of individual members of a family of miRNAs, the ESCC miRNAs, into Dgcr8−/− ESCs can rescue the cell cycle defect (Wang, Y. et al., *Nat Genet,* 40:1478-1483 (2008)). We have discovered that these same miRNAs are able to enhance the de-differentiation of somatic cells to iPS cells and also have identified another large family of miRNAs, the let-7 family, which performs the opposite role to the ESCC family. When introduced into Dgcr8−/− ESCs, let-7 silences self-renewal by suppressing many of the same downstream targets that are indirectly activated by the ESCC family. Indeed, co-introduction of the ESCC miRNAs inhibits the capacity of let-7 to silence self-renewal, and suppression of the let-7 family in somatic cells promotes de-differentiation.

BRIEF SUMMARY OF THE INVENTION

The present invention is based on findings that introduction of physiologically relevant miRNAs can affect somatic cell reprogramming.

In a first aspect, the invention provides that the mouse embryonic stem (ES) cell specific microRNAs (miRNA) miR-291-3p, miR-294, and miR-295 enhanced the efficiency of Klf4, Oct4 and Sox2 induced pluripotency. The invention further demonstrates that these miRNAs did not further enhance reprogramming in the presence of cMyc. As cMyc binds the promoter of these miRNAs, these microRNAs may be downstream effectors of cMyc promoted pluripotency. Unlike exogenous cMyc, these miRNAs induced a homogeneous population of reprogrammed colonies suggesting overlapping and independent functions of cMyc and the miRNAs. Further, as microRNAs can be introduced without the use of retroviral vectors, they exhibit significant potential for use as therapeutic agents.

In this aspect, the present invention is based on a method for inducing pluripotency in an isolated cell comprising introducing a physiologically relevant miRNA into said cell. In some embodiments the miRNA contains the seed sequence AAGUGCU (SEQ ID NO:15) or AAGUGC. In some embodiments the miRNA contains the seed sequence AAAGUGC (SEQ ID NO: 16). In some embodiments the miRNA affects cell reprogramming. In some embodiments the effect on cell reprogramming induces pluripotency in the cell. In some embodiments the effect on cell reprogramming induces de-differentiation in the cell. In some embodiments the effect on cell reprogramming induces partial de-differentiation. In some embodiments the effect on cell reprogramming induces trans-differentiation.

In some embodiments, the miRNA is an embryonic stem cell cycle (ESCC) regulating miRNA. In some embodiments the mi RNA is a member of the embryonic stem cell cycle (ESCC) regulating miR-290 cluster.

In some embodiments of the present invention the miRNA is a human miRNA. In some embodiments the miRNA is a mouse miRNA. In some embodiments the miRNA of the present invention is one of miR-291-3p (SEQ ID NO:1), miR-294 (SEQ ID NO:2) miR-295 (SEQ ID NO:3), miR-302d (SEQ ID NO:4), miR-292-3p (SEQ ID NO:5), hsa-miR-302a (SEQ ID NO:8), hsa-miR-302b (SEQ ID NO:9), hsa-miR-302c (SEQ ID NO:10), hsa-miR-302d (SEQ ID NO:11), hsa-miR371-5p (SEQ ID NO:12), hsa-miR-372 (SEQ ID NO:13), hsa-miR-373 (SEQ ID NO:14), hsa-miR-17 (SEQ ID NO:17), hsa-miR-20a (SEQ ID NO:18), hsa-miR-20b (SEQ ID NO:19), hsa-miR-93 (SEQ ID NO:20), hsa-miR-106a (SEQ ID NO:21), or hsa-miR-106b (SEQ ID NO:22).

In some embodiments of the methods of the present invention the cell is a human cell. In some embodiments of the present invention the cell can be any of the cells typically utilized in generating cells that harbor recombinant nucleic acid constructs. In some embodiments the cells can be cultured cells or cell lines such as but not limited to COS, CHO, HeLa, 293T or mouse embryonic fibroblasts (MEFs). In some embodiments the cell types utilized for the methods of the present invention can include naturally occurring cells isolated from tissue samples including but not limited to blood, bone, brain, kidney, muscle, spinal cord, nerve, endocrine system, uterine, ear, foreskin, liver, intestine, bladder or skin. In some embodiments the cells can include neural cells, lymphocytes, epidermal cells, islet cells, intestinal cells or fibroblasts. In some embodiments the cells of the present invention can be autologous or heterologous cells. In some embodiments the cells useful for the methods of the present invention can include animal cells. In some embodiments the cells are mammalian. In some embodiments the cells are diseased human cells, such as cancer cells. In some embodiments the cancer cells can include but are not limited to breast, prostate, liver, bladder, brain, blood or bone cancer cells.

In some embodiments of the present invention the miRNA is 80% or more identical to one of miR-291-3p (SEQ ID NO:1), miR-294 (SEQ ID NO:2), miR-295 (SEQ ID NO:3), miR-302d (SEQ ID NO:4), miR-292-3p (SEQ ID NO:5), hsa-mir-302a (SEQ ID NO:8), hsa-miR-302b (SEQ ID NO:9), hsa-miR-302c (SEQ ID NO:10), hsa-miR-302d (SEQ ID NO:11), hsa-miR371-5 (SEQ ID NO:12), hsa-miR-372 (SEQ ID NO:13), hsa-miR-373 (SEQ ID NO:14), hsa-miR-17 (SEQ ID NO:17), hsa-miR-20a (SEQ ID NO:18), hsa-miR-20b (SEQ ID NO:19), hsa-miR-93 (SEQ ID NO:20), hsa-mir-106a (SEQ ID NO:21), or hsa-mir-106b (SEQ ID NO:22). In some embodiments of the present invention the miRNA contains the seed sequence AAGUGCU (SEQ ID NO:15). In some embodiments of the present invention the miRNA contains the seed sequence AAAGUGC (SEQ ID NO:16). In some embodiments of the present invention the miRNA is 80% or more identical to one of miR-291-3p (SEQ ID NO:1), miR-294 (SEQ ID NO:2), miR-295 (SEQ ID NO:3), miR-302d (SEQ ID NO:4), hsa-miR-302a (SEQ ID NO:8), hsa-miR-302b (SEQ ID NO:9), hsa-miR-302c (SEQ ID NO:10), hsa-miR-302d (SEQ ID NO:11), hsa-miR371-5p (SEQ ID NO:12), hsa-miR-372 (SEQ ID NO:13), hsa-miR-373 (SEQ ID NO:14), hsa-miR-17 (SEQ ID NO:17), hsa-miR-20a (SEQ ID NO:18), hsa-miR-20b (SEQ ID NO:19), hsa-miR-93 (SEQ ID NO:20), hsa-miR-106a (SEQ ID NO:21), or hsa-miR-106b (SEQ ID NO:22), and contains the seed sequence AAGUGCU (SEQ ID NO:15). In some embodiments of the present invention the miRNA is 80% or more identical to one of miR-291-3p (SEQ ID NO:1), miR-294 (SEQ ID NO:2), miR-295 (SEQ ID NO:3), miR-302d (SEQ ID NO:4), hsa-miR-302a (SEQ ID NO:8), hsa-miR-302b (SEQ ID NO:9), hsa-miR-302c (SEQ ID NO:10), hsa-miR-302d (SEQ ID NO:11), hsa-miR371-5p (SEQ ID NO:12), hsa-miR-372 (SEQ ID NO:13), hsa-miR-373 (SEQ ID NO:14), hsa-miR-17 (SEQ ID NO:17), hsa-miR-20a (SEQ ID NO:18), hsa-miR-20b (SEQ ID NO:19), hsa-miR-93 (SEQ ID NO:20), hsa-miR-106a (SEQ ID NO:21), or hsa-miR-106b (SEQ ID NO:22), and contains the seed sequence AAAGUGC (SEQ ID NO:16).

In some embodiments of the present invention the miRNA is a member of miR-290 cluster. In some embodiments the miRNA is one of miR-291-3p (SEQ ID NO:1), miR-294 (SEQ ID NO:2) miR-295 (SEQ ID NO:3), miR-302d (SEQ ID NO:4), miR-292-3p (SEQ ID NO:5), hsa-miR-302a (SEQ ID NO:8), hsa-miR-302b (SEQ ID NO:9), hsa-miR-302c (SEQ ID NO:10), hsa-miR-302d (SEQ ID NO:11), hsa-miR371-5p (SEQ ID NO:12), hsa-miR-372 (SEQ ID NO:13), or hsa-miR-373 (SEQ ID NO:14).

In some embodiments of the present invention the effect on cell reprogramming is to enhance reprogramming. In some embodiments methods of the present invention include inducing pluripotency in a cell, such that the cell becomes capable of dividing and differentiating into any cell type other than embryonic cells. In some embodiments cellular reprogramming can include inducing pluripotency in or de-differentiation of the cell. In some embodiments altering cell reprogramming can refer to enhancing the level of pluripotency or de-differentiation that has been induced by an agent other than a microRNA. In some embodiments, the pluripotent or multipotent cells, also called stem cells, have the ability to divide (self-replicate or self-renew) or differentiate into multiple different phenotypic lineages for indefinite periods. In some embodiments, the cells of the present invention when under specific conditions, or in the presence of optimal regulatory signals, can become pluripotent and differentiate themselves into many different cell types that make up the organism. In some embodiments the pluripotent or multipotent cells of the present invention possess the ability to differentiate into mature cells that have characteristic attributes and specialized functions, such as hair follicle cells, blood cells, heart cells, eye cells, skin cells, pancreatic cells, or nerve cells. In some embodiments of the present invention cell reprogramming can further include partial dc-differentiation to a closely related cell or cell type. In some embodiments cell reprogramming can also include trans-differentiation, wherein a cell of the present invention converts from one differentiated cell type into another differentiated cell type. In some embodiments of the above the cell expresses, or was transduced with retroviruses expressing Oct4, Sox2, and Klf4 (OSK).

In some embodiments of the present invention the enhancement of cell reprogramming constitutes enhancement of pluripotency. In some embodiments the enhancement of cell reprogramming constitutes enhancement of de-differentiation.

In some embodiments the isolated cell of the present invention contains one miRNA. In some embodiments the isolated cell of the present invention contains more than one miRNA. In some embodiments the isolated cell of the present invention contain one miRNA, wherein the miRNA contains the seed sequence AAGUGCU (SEQ ID NO: 15) or AAGUGC. In some embodiments the isolated cell of the present invention contains one miRNA, wherein the miRNA contains the seed sequence AAAGUGC (SEQ ID NO: 16). In some embodiments the isolated cell of the present invention contains more than one miRNA, wherein the miRNA contains the seed sequence AAGUGCU (SEQ ID NO:15) or AAGUGC. In some embodiments the isolated cell of the present invention contains more than one miRNA, wherein the miRNA contains the seed sequence AAAGUGC (SEQ ID NO: 16). In some embodiments of the present invention the miRNA containing cells are in cell culture. In some embodiments of the present invention the miRNA containing cells are in cell culture and contain one or more of the miRNAs.

In embodiments of methods of the present invention the methods include treating an individual with a degenerative disease. In some embodiments of the methods of the present invention comprise treating an individual by administering to an individual a cell containing an miRNA of the present invention. In some embodiments the miRNA contains the seed sequence AAGUGCU (SEQ ID NO:15) or AAGUGC. In some embodiments the miRNA contains the seed sequence AAAGUGC (SEQ ID NO:16). In some embodiments the miRNA affects cell reprogramming. In some embodiments the effect on cell reprogramming induces pluripotency in the cell. In some embodiments the effect on cell reprogramming induces de-differentiation in the cell. In some embodiments the effect on cell reprogramming induces partial de-differentiation. In some embodiments the effect on cell reprogramming induces trans-differentiation. In some embodiments of the present invention the miRNA is 80% or more identical to one of miR-291-3p (SEQ ID NO:1), miR-294 (SEQ ID NO:2), miR-295 (SEQ ID NO:3), miR-302d (SEQ ID NO:4), miR-292-3p (SEQ ID NO:5), hsa-miR-302a (SEQ ID NO:8), hsa-miR-302b (SEQ ID NO:9), hsa-miR-302c (SEQ ID NO:10), hsa-miR-302d (SEQ ID NO:11), hsa-miR371-5p (SEQ ID NO:12), hsa-miR-372 (SEQ ID NO:13), hsa-miR-373 (SEQ ID NO:14), hsa-miR-17 (SEQ ID NO:17), hsa-miR-20a (SEQ ID NO:18), hsa-miR-20b (SEQ ID NO:19), hsa-miR-93 (SEQ ID NO:20), hsa-miR-106a (SEQ ID NO:21), or hsa-miR-106b (SEQ ID NO:22). In some embodiments of the present invention the miRNA contains the seed sequence AAGUGCU (SEQ ID NO:15) or AAGUGC. In some embodiments of the present invention the miRNA contains the seed sequence AAAGUGC (SEQ ID NO:16). In some embodiments of the present invention the miRNA is 80% or more identical to one of miR-291-3p (SEQ ID NO:1), miR-294 (SEQ ID NO:2), miR-295 (SEQ ID NO:3), miR-302d (SEQ ID NO:4), miR-292-3p (SEQ ID NO:5), hsa-miR-302a (SEQ ID NO:8), hsa-miR-302b (SEQ ID NO:9), hsa-miR-302c (SEQ ID NO:10), hsa-miR-302d (SEQ ID NO:11), hsa-miR371-5p (SEQ ID NO:12), hsa-miR-372 (SEQ ID NO:13), hsa-miR-373 (SEQ ID NO:14), hsa-miR-17 (SEQ ID NO:17), hsa-miR-20a (SEQ ID NO:18), hsa-miR-20b (SEQ ID NO:19), hsa-miR-93 (SEQ ID NO:20), hsa-mir-106a (SEQ ID NO:21), or hsa-mir-106b (SEQ ID NO:22), and contains the seed sequence AAGUGCU (SEQ ID NO:15) or AAGUGC. In some embodiments of the present invention the miRNA is 80% or more identical to one of miR-291-3p (SEQ ID NO:1), miR-294 (SEQ ID NO:2), miR-295 (SEQ ID NO:3), miR-302d (SEQ ID NO:4), miR-292-3p (SEQ ID NO:5), hsa-miR-302a (SEQ ID NO:8), hsa-miR-302b (SEQ ID NO:9), hsa-miR-302c (SEQ ID NO:10), hsa-miR-302d (SEQ ID NO:11), hsa-miR371-5p (SEQ ID NO:12), hsa-miR-372 (SEQ ID NO:13), hsa-miR-373 (SEQ ID NO:14), hsa-miR-17 (SEQ ID NO:17), hsa-miR-20a (SEQ ID NO:18), hsa-miR-20b (SEQ ID NO:19), hsa-miR-93 (SEQ ID NO:20), hsa-miR-106a (SEQ ID NO:21), or hsa-miR-106b (SEQ ID NO:22), and contains the seed sequence AAAGUGC (SEQ ID NO:16). The treatments may be ex vivo or in vivo. In some embodiments of any of the above, the cells are autologous. For instance, in some embodiments, the cells may be obtained from the intended recipient having the disease, treated with the miRNA in order to induce pluripotency or reprogram the cells, and returned to the intended recipient.

In some embodiments of the methods of the present invention, the methods include treating and individual with a degenerative disease. In some embodiments the degenerative disease includes but is not limited to Parkinson's Disease, Alzheimer's Disease, skin grafts, Muscular Dystrophy, Amyotrophic Lateral Sclerosis (ALS) (e.g., Lou Gehrig's Disease), Multiple system atrophy, Niemann Pick disease, Atherosclerosis, Progressive supranuclear palsy, cancer, metabolic diseases (including for example but not limited to Tay-Sachs Disease), Diabetes, Heart Disease, Inflammatory Bowel Disease (IBD), Norric disease, Prostatitis, Osteoarthritis, Osteoporosis, Rheumatoid Arthritis, Sickle Cell Anemia, heart disease, spinal and nerve related diseases and disorders (including spinal and nerve related injuries), cancers (including for example but not limited to leukemias and lymphomas), other injuries induced by trauma, as well as regeneration of tissue post-resectioning.

In some embodiments of any of the above, the miRNA is an miRNA set forth in Example 3 or 4.

In a second aspect, the invention provides a method of stabilizing a somatic cell in a differentiated state or of reducing the proliferation rate of a cell by administering a Let-7 miRNA or a miRNA having the seed sequence of Let-7 (e.g., mir-98, (ugagguaguaaguuguauuguu; SEQ ID NO:291)) to the cell and/or by administering an inhibitor of an miRNA according to SEQ ID NOS:1 to 22 or an inhibitor of an miRNA having the seed sequence of SEQ ID NOS:15 or 16 or AAGUGC, or administering an miRNA set forth in Examples 5 or 6. In some embodiments, one, two, three or more of these miRNA and/or their inhibitors is administered to the cell. In some embodiments, the Let-7 miRNA is selected from the group consisting of Let-7a, Let-7b, Let-7c, Let-7d, Let-7e, Let-7f, and Let-7g. In some embodiments, the invention provides a method of treating a subject having a disease mediated by proliferating cells (e.g., cancer, and autoimmune disease) by administering to the subject a therapeutically effective amount of a Let-7 miRNA or a miRNA set forth in Example 5 and/or administering a therapeutically effective amount of an inhibitor of an miRNA according to SEQ ID NOS:1 to 22 or an inhibitor of an miRNA having the seed sequence of SEQ ID NOS:15 or 16 or of AAGUGC.

In another embodiment of this second aspect, the invention provides a method of inducing pluripotency in a somatic cell by administering an inhibitor of a Let-7 miRNA or of an miRNA of Example 5 to the cell and/or by administering an miRNA according to SEQ ID NOS:1 to 22 or an inhibitor of an miRNA having the seed sequence of SEQ ID NOS:15 and 16 or of AAGUGC. In some embodiments of the methods of the present invention, the methods include treating an individual with a degenerative disease by administering a therapeutically effective amount of an inhibitor of a Let-7 miRNA or a miRNA having the seed sequence of Let-7 (e.g., mir-98, (ugagguaguaaguuguauuguu; SEQ ID NO:291)) or an inhibitor of an miRNA of Example 5 or 6 to the cell and/or by administering a therapeutically effective amount of an miRNA according to SEQ ID NOS:1 to 22 or of Examples 3 or 4 or of an miRNA having the seed sequence of SEQ ID NOS:15 and 16 or of AAGUGC. In some embodiments, one, two, three or more of these miRNA or their inhibitors is administered. In some embodiments, the degenerative disease includes but is not limited to Parkinson's Disease, Alzheimer's Disease, skin grafts, Muscular Dystrophy, Amyotrophic Lateral Sclerosis (ALS) (e.g., Lou Gehrig's Disease), Multiple system atrophy, Niemann Pick disease, Atherosclerosis, Progressive supranuclear palsy, cancer, metabolic diseases (including for example but not limited to Tay-Sachs Disease), Diabetes, Heart Disease, Inflammatory Bowel Disease (IBD), Norrie disease, Prostatitis, Osteoarthritis, Osteoporosis, Rheumatoid Arthritis, Sickle Cell Anemia, heart disease, spinal and nerve related diseases and disorders (including spinal and nerve related injuries), cancers (including for example but not limited to leukemias and lymphomas), other injuries induced by trauma, as well as regeneration of tissue post-resectioning.

In another aspect the invention provides a method of supporting, promoting, or stabilizing the differentiation of, or preventing the proliferation of a cell, comprising administering a micronucleic acid or inhibitor (e.g. a member of the let-7 family or a miRNA having the seed sequence of Let-7 (e.g., mir-98, (ugagguaguaaguuguauuguu)); an miRNA of Example 5 an miRNA of FIG. 20, an ESCC miRNA inhibitor, or an inhibitor of any miRNA of Example 4) to the cell. In some embodiments, the cell is an induced pluripotent cell, an embryonic stem cell or is derived from an iPS, or ES cell. In some embodiments of any of the above, the nucleic acid is administered to cells in culture or is administered systemically to a patient, with the intention of targeting the cells. In some embodiments, one, two, three or more of these miRNA and/or their inhibitors is administered. In some embodiments the cells are further introduced into a mammalian host (with a greatly reduced likelihood of any cells therein would be capable of causing a teratoma in the host. The cells may be heterologous or autologous with regard to the host or patient. The cells may be introduced to treat a degenerative condition in the host or restore a cellular function or cell type deficient in the host. In some embodiments, the invention provides cells which have been obtained by administering the micronucleic acid or inhibitor to the cell.

In any of the above embodiments and aspects, the miRNA can be introduced as a pre- or primary miRNA. In some embodiments, an miRNA or inhibitor thereof from Examples 3 to 6, SEQ ID NOS:1 to 14, or having the seed sequence of SEQ ID NOS:15 and 16 or of AAGUGC or let-7 is used to reprogram a cell. In some embodiments, one two, three or more members selected from the miRNAs and inhibitors are used together or sequentially. In some embodiments, the members each act to either to promote de-differentiation of a cell. In other embodiments, the members each act to support, promote, or stabilize the differentiation of, or prevent the proliferation of a cell. In still other embodiments, some members are used first to de-differentiate a cell and other members are later used to re-differentiate, support, promote, or stabilize the differentiation of, or prevent the proliferation of a cell.

DETAILED DESCRIPTION

The breadth and importance of miRNA directed gene regulation is becoming more apparent as more miRNAs and their regulatory targets are identified and described. Recently discovered functions include control of cell proliferation, cell death, fat metabolism in nematodes, modulation of hematopoietic lineage and control of leaf and flower development in plants (see, e.g., Bartel, D. P., *MicroRNAs: Genomics, Biogenesis, Mechanism, and Function* Cell 116:281-297 (2004)).

The methods of the present invention focus on the induction or modulation of pluripotency by miRNAs. In some embodiments the miRNAs of the invention contain a seed sequence (SEQ ID NO:15) or AAGUGC. In some embodiments, the miRNAs are embryonic stem cell cycle regulating miRNAs. In some embodiments, miRNAs are members of the embryonic stem cell cycle regulating cluster miR-290. In some embodiments the miRNAs are human or mouse miRNAs. In some embodiments, the miRNAs are selected from the group including but not limited to miR-291-3p (SEQ ID NO:1), miR-294 (SEQ ID NO:2), miR-295 (SEQ ID NO:3), miR-302d (SEQ ID NO:4), miR-292-3p (SEQ ID NO:5), miR-293 (SEQ ID NO:6), miR-294 mut (SEQ ID NO:7), hsa-miR-302a (SEQ ID NO:8), hsa-miR-302b (SEQ ID NO:9), hsa-miR-302c (SEQ ID NO:10), hsa-miR-302d (SEQ ID NO:11), hsa-miR-371-5p (SEQ ID NO:12), hsa-miR-372 (SEQ ID NO:13), hsa-miR-373 (SEQ ID NO:14), hsa-miR-17 (SEQ ID NO:17), hsa-miR-20a (SEQ ID NO:18), hsa-miR-20b (SEQ ID NO:19), hsa-miR-93 (SEQ ID NO:20), hsa-miR-106a (SEQ ID NO:21), or hsa-miR-106b (SEQ ID NO:22).

Figure 22:
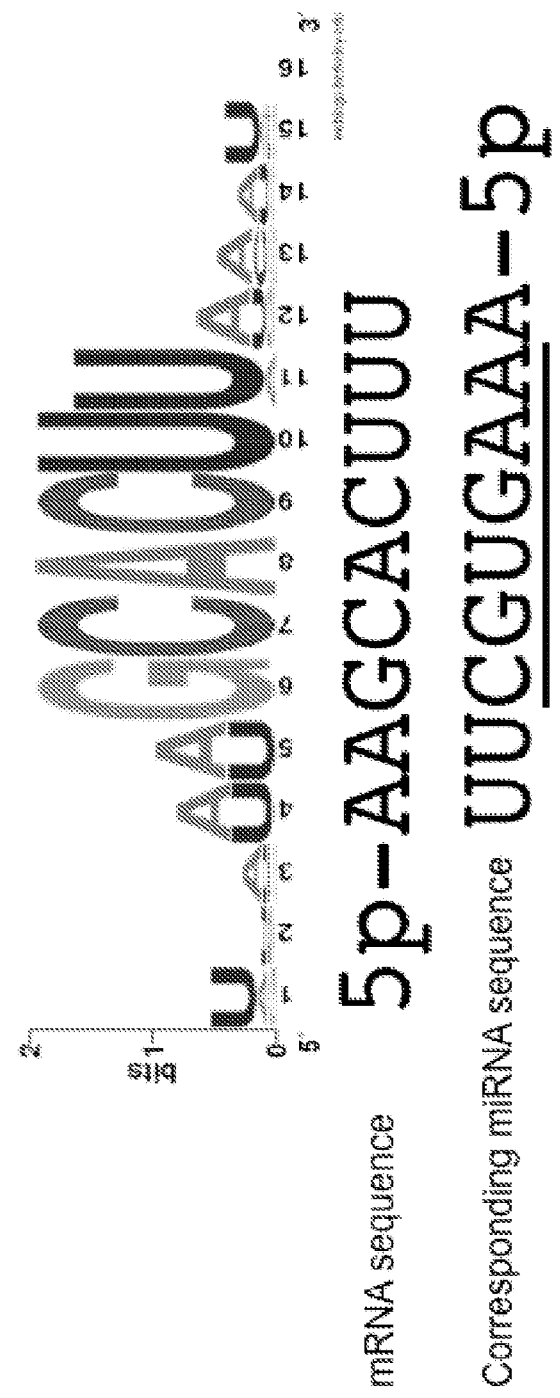
FIG. 22. Results of an experiment looking for enriched motifs located within the 3p UTRs of transcripts which were found to be down-regulated in Dgcr8−/− ESCs 12 hours after introduction of miR-294 miRNA mimic. These motifs were identified as 4 fold or greater enriched in the 3p UTRs of downregulated transcripts compared to all other transcripts on the microarrays. Motifs were measured for their similarity to one another and motifs with 2 or fewer mismatches were clustered together. This particular cluster represents the motifs corresponding to the miRNA seed sequence (SEQ ID NO:277). The consensus of these motifs is shown in this figure. These data support the idea that the minimal seed sequence of AAGUGC is required for ESCC miRNA function.

Accordingly, the invention provides a method of inducing pluripotency in an isolated cell comprising introducing a small nucleic acid into said cell, wherein the nucleic acid affects cell reprogramming; thereby inducing pluripotency in a cell. The nucleic acid can be a microRNA or miRNA mimic. For instance, the miRNA can be a member of the embryonic stem cell cycle (ESCC) miRNAs that include the 290 family 302 cluster, 17 to 19 cluster, and mir-106. The miRNA can also be a member of the 370 family in humans. In some embodiments, the miRNA contains the seed sequence AAGUGCU (SEQ ID NO:15) or AAGUGC or AAAGUGC (SEQ ID NO:16) or the sequence AAGUGC (see, FIG. 22). In other embodiments, the miRNA is any of the miRNAs listed in Example 4. In yet other embodiments, the nucleic acid is an inhibitor of a microRNA (e.g., the small nucleic acid is an inhibitor of the miRNA of the let-7 family). In some further embodiments, the nucleic acid inhibits an miRNA listed in Example 5 or a silencing miRNA of FIG. 20. In yet other embodiments, the miRNA being inhibited is a silencing miRNA of FIG. 20. In some embodiments, one, two, three or more of these miRNA and/or their inhibitors is administered to the cell. In any of the above embodiments, the miRNA and the cell is human or mouse. For instance, the isolated cell may be a human or mouse fibroblast or keratinocyte. In still other embodiments, the miRNA is (i) substantially identical or 80% or more percent identical in sequence to one of miR-291-3p (SEQ ID NO:1), miR-294 (SEQ ID NO:2), miR-295 (SEQ ID NO:3), miR-302d (SEQ ID NO:4), miR-292-3p (SEQ ID NO:5), hsa-miR-302a (SEQ ID NO:8), hsa-miR-302b (SEQ ID NO:9), hsa-miR-302c (SEQ ID NO:10), hsa-miR-302d (SEQ ID NO:11), hsa-miR-372 (SEQ ID NO:13), hsa-miR-373 (SEQ ID NO:14), hsa-miR-17 (SEQ ID NO:17), hsa-miR-20a (SEQ ID NO:18), hsa-miR-20b (SEQ ID NO:19), hsa-miR-93 (SEQ ID NO:20), hsa-miR-106a (SEQ ID NO:21), or hsa-miR-106b (SEQ ID NO:22); or a miRNA of Example 4; and (ii) contains the seed sequence AAGUGCU (SEQ ID NO:15) or AAAGUGC (SEQ ID NO:16) or (iii) contains the sequence AAGUGC. In some additional embodiments, the nucleic acid is an ESCC microRNA selected from miR-291-3p (SEQ ID NO:1), miR-294 (SEQ ID NO:2) miR-295 (SEQ ID NO:3), miR-302d (SEQ ID NO:4), miR-292-3p (SEQ ID NO:5), hsa-miR-302a (SEQ ID NO:8), hsa-miR-302b (SEQ ID NO:9), hsa-miR-302c (SEQ ID NO:10), hsa-miR-302d (SEQ ID NO:11), and could also include members of the 370 cluster of microRNAs in the human: hsa-miR371-5p (SEQ ID NO:12), hsa-miR-372 (SEQ ID NO:13), or hsa-miR-373 (SEQ ID NO:14). In still other embodiments of any of the above, the effect on reprogramming is to enhance reprogramming (e.g., enhancement of pluripotency or de-differentiation).

In other further embodiments of the above, one or more reprogramming factors are also introduced to the cell. These factors include Oct4, Sox2, and Klf4 (OSK), cMyc, Nr5a2, Essrb, cyclinD1, Nanog, Lin28, Sa114, UTF1 or other members of these families. For instance, the contemplated factors include inhibitors to p53, p16, p19, p21 or other family members. The factors can be introduced virally, via a plasmid, via a transposon, as a protein, as RNA or DNA encoding the factor. The factors and small molecules (e.g., VPA, TSA, 5'-azac, kenpaullone, TGFβ-inhibitors, Wnts, vitamin C, BIX-01294, BayK8644), as well as the nucleic acids, can be introduced into the cell directly or to the cell media.

Accordingly, in still other embodiments the invention provides isolated cells produced by the above methods. The cell may, for instance, contain one, two, three or more miRNAs containing seed sequence AAGUGCU (SEQ ID NO:15) or AAAGUGC (SEQ ID NO:16) or AAGUGC. The invention also provides a method of treating a patient comprising, 1) obtaining and culturing and/or expanding a population of cells from the patient or compatible donor (e.g., fibroblasts, keratinocytes, somatic cells) 2) de-differentiating the cells with a mixture of reprogramming factors including ESCC miRNAs and/or Let7 inhibitors to generate iPS cells, optionally further culturing and expanding the iPS cell population, 3) differentiating the iPS into cell types required by the patient; and 4) treating the cells with Let-7miRNA and/or ESCC inhibitors to help maintain the differentiated phenotype and/or reduce or prevent the presence of any pluripotent cells; and administering (e.g., injecting or returning) the cells to the patient. Most commonly used cells are derived from skin biopsies, hair follicles, newborn foreskin, human cord blood, human fetal neural stem cells of the patient or donor. The cells are preferably returned or instilled into the tissue or site of their deficiency. In some embodiments, the individual has a degenerative disease. In some such embodiments, the degenerative disease is one or more of Parkinson's Disease, Alzheimer's Disease, skin grafts, Muscular Dystrophy, Amyotrophic Lateral Sclerosis (ALS) (e.g., Lou Gehrig's Disease), Multiple system atrophy, Niemann Pick disease, Atherosclerosis, Progressive supranuclear palsy, cancer, metabolic diseases (including for example but not limited to Tay-Sachs Disease), Diabetes, Heart Disease, Inflammatory Bowel Disease (IBD), Norrie disease, Prostatitis, Osteoarthritis, Osteoporosis, Rheumatoid Arthritis, Sickle Cell Anemia, heart disease, spinal and nerve related diseases and disorders, cancers (including for example but not limited to leukemias and lymphomas), other injuries induced by trauma, or regeneration of tissue post-resectioning.

An exemplary method of inducing de-differentiation of human somatic cells is to 1) plate the cells on gelatin (e.g., plate 30,000 cells on gelatin in a 6-well plate); 2) at about 24 hours later, introduce exogenous factors such as Oct4, Sox2 and Klf4 into the cells (e.g., by viral transduction, transfection, or introduction of the proteins); 3) at 2 days post infection, switch the cells to human ES medium containing 10 ng/ml bFGF. Transfection mixes consisting of 50 or 100 nM of the small RNA mimic and the transfection reagent Dharmafect1 are added to the cells on days 3 and 10 post infection. The culture medium can be changed every other day. Colonies typically appear between 2 to 4 weeks post infection. Colonies can be picked onto irradiated MEFs and passaged according to standard practices used for passaging human ES cells. In embodiments where administration of a re-programmed human cell to humans is contemplated, "xeno free" or "humanized" conditions as known to persons of ordinary skill in the art can be used to culture the cells.

When embryonic stem cells (ESCs) differentiate, they must both silence the ESC self-renewal program as well as activate new tissue specific programs. In the absence of DGCR8 (Dgcr8−/−), a protein required for microRNA (miRNA) biogenesis, mouse ESCs are unable to silence self-renewal. Here, we also report that the introduction of let-7 miRNAs, a family of miRNAs highly expressed in somatic cells, can suppress self-renewal in Dgcr8−/−, but not wild-type ESCs. Introduction of ESC cell cycle regulating (ESCC) miRNAs into the Dgcr8−/− ESCs, blocks the capacity of let-7 to suppress self-renewal. Profiling and bioinformatic analyses show that let-7 inhibits while ESCC miRNAs indirectly activate numerous self-renewal genes. Furthermore, inhibition of the let-7 family promotes de-differentiation of somatic cells to induced pluripotent stem (iPS) cells. Together, these findings show how the ESCC and let-7 miRNAs act through common pathways to alternatively stabilize the self-renewing versus differentiated cell fates.

Figure 14:
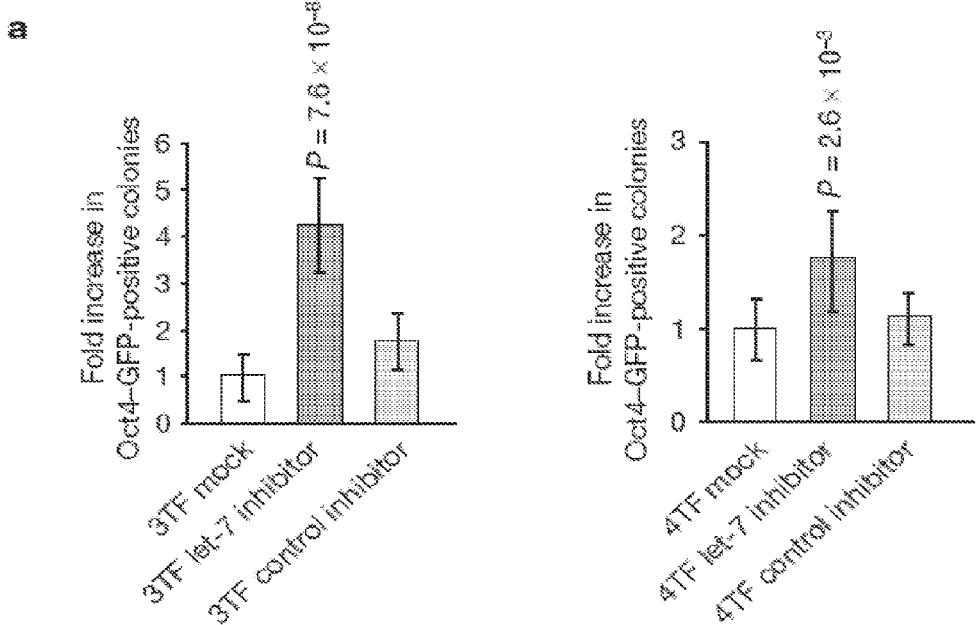
FIG. 14. Inhibition of let-7 miRNAs promotes reprogramming to induced pluripotency (a) Fold increase of Oct4::GFP positive colonies in reprogramming with transduction of 3TFs (Pou5fl/Oct4, Sox2, and Klf4) or 4TFs (+cMyc) after mock, let-7 inhibitor, or control inhibitor transfection. P-values are indicated for p<0.01 calculated by Bonferroni corrected t-test. n=10 for mock and let-7 inhibitor samples and n=6 for control inhibitor samples (b) A model of the antagonism between the miR-294 and let-7c in the stabilization of the self-renewing and differentiated states. Bold and enlarged genes and arrows are active in the indicated state. Mechanisms of ESCC upregulation of Lin28 and cMyc are unknown and represented by a question mark.
Figure 14:
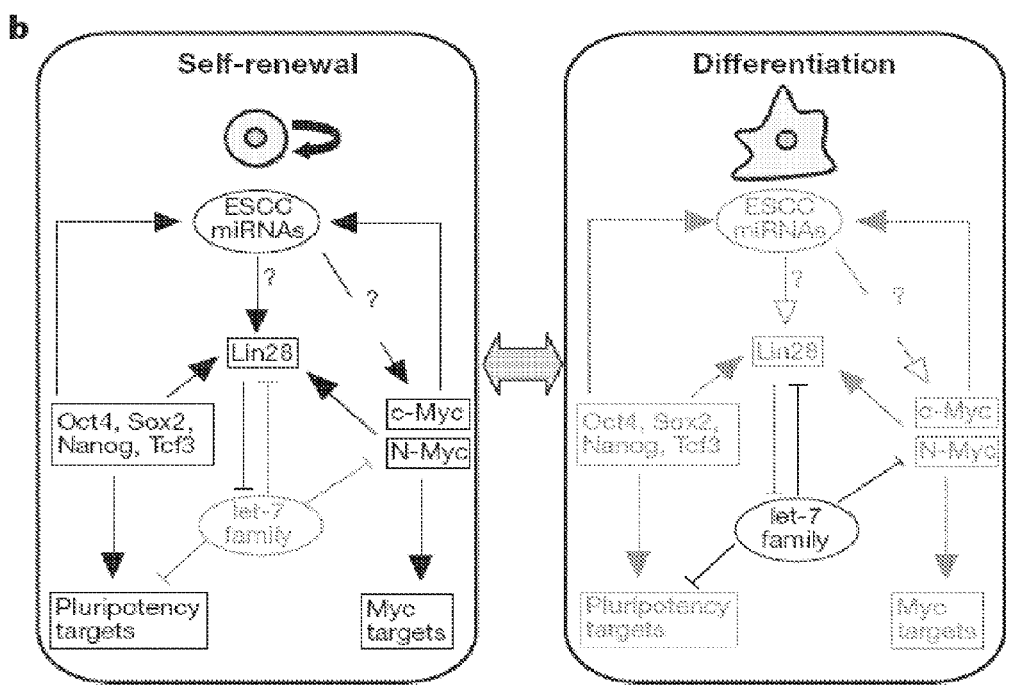

Our findings show that the let-7 and ESCC miRNA families have opposing effects on ESC self-renewal. Without being held to theory, we believe that they act in self-reinforcing loops to maintain the ESC self-renewing versus differentiated cell states (FIG. 14b). In the self-renewing state, ESCC miRNAs would then indirectly increase expression of Lin28 and cMyc. Lin28 functions to block the maturation of let-7 (Rybak, A. et al. *Nat Cell Biol* 10:987-93 (2008); Viswanathan, S. R. et al., *Science* 320:97-100 (2008); Heo, I. et al. *Mol Cell* 32:276-84 (2008); Newman, M. A. et al., *RNA* 14:1539-49 (2008)). Therefore, the ESCC miRNAs prevent co-expression of let-7 miRNAs. Additionally, without being bound to theory, we believe the ESCC-induced upregulation of cMyc forms a positive feedback loop in which cMyc and nMyc, along with Pou5fl/Oct4, Sox2, and Nanog, bind and activate expression of the ESCC miRNAs in the miR-290 miRNA cluster (Judson, R. et al., *Nat Biotech* (2009); Marson, A. et al. *Cell* 134:521-33 (2008)). As ESCs differentiate, Pou5fl/Oct4, Sox2, and Nanog are then downregulated, resulting in the loss of ESCC and Lin28 expression. With the loss of Lin28, mature let-7 rapidly would increase. This increase in let-7 would then be enhanced by a positive feedback loop in which let-7 suppresses its own negative regulator Lin28. In the differentiated state, downregulation of Myc activity by let-7 would prevent co-expression of the ESCC miRNAs. Furthermore, let-7 inhibits downstream targets of Pou5fl/Oct4, Sox2, Nanog, and Tcf3 to stabilize the differentiated state. Sal14, like Myc and Lin28, is positively regulated by the ESCC family and negatively regulated by let-7 family. Decreases in Myc, Sa114, and Lin28 all promote ESC differentiation (Lim, C. Y. et al. *Cell Stem Cell* 3:543-54 (2008); Zhang, J. et al. *Nat Cell Biol* 8:1114-23 (2006); Heo, I. et al. *Cell* 138:696-708 (2009); Cartwright, P. et al. *Development* 132:885-96 (2005)).

In this model, the function of let-7 in repressing the self-renewing state is restricted to cells that do not express high levels of ESCC miRNAs. In fact, our model suggests that let-7 and ESCC miRNAs are not normally co-expressed at high levels. For this reason, we propose that the let-7 family does not function to initiate differentiation, but rather the antagonism between the let-7 and ESCC families stabilizes the switch between self-renewal and differentiation. Consistent with this model, the introduction of either ESCC miRNAs (Judson, R. et al., *Nat Biotech* (2009)) or let-7 inhibitors into somatic cells promotes their de-differentiation into iPS cells. Additionally, the ESCC and let-7 miRNAs make up a preponderance of the miRNAs in self-renewing ESCs and somatic cells respectively (Marson, A. et al. *Cell* 134:521-33 (2008)), supporting a major role in influencing these alternative cell fates.

Other miRNAs have been reported to target the ESC transcriptional network (Tay, Y. M. et al. *Stem Cells* 26:17-29 (2008); Tay, Y. et al., *Nature* 455:1124-8 (2008); Xu, N. et al., *Cell* 137:647-658 (2009)). Unlike the let-7 family, these other miRNAs have a more limited tissue distribution (Landgraf, P. et al. *Cell* 129:1401-1414 (2007); Chen, C. et al. *Mamm. Genome* 18:316-327 (2007)), suggesting that they may suppress self-renewal during differentiation along specific developmental pathways. Alternatively, these miRNAs may be involved in the early and transient stages of ESC differentiation while the let-7 miRNAs are involved in stabilizing the resulting differentiated cell fate. miRNAs related to the ESCC family (miR-17, miR-20, miR-93, and miR-106) and let-7 miRNAs play analogous roles in cancer with the ESCC related miRNAs promoting and the let-7 miRNAs inhibiting cancer growth (Mendell, J. T. *Cell* 133:217-222 (2008); Bussing, I. et al., *Trends in Molecular Medicine* 14:400-409 (2008)). Thus, we contemplate that these miRNAs can act through similar opposing pathways in cancer.

A "target gene" refers to any gene suitable for regulation of expression, including both endogenous chromosomal genes and transgenes, as well as episomal or extrachromosomal genes, mitochondrial genes, chloroplastic genes, viral genes, bacterial genes, animal genes, plant genes, protozoal genes and fungal genes.

A "microRNA" or "miRNA" refers to a nucleic acid that forms a single-stranded RNA, which single-stranded RNA has the ability to alter the expression (reduce or inhibit expression; modulate expression; directly or indirectly enhance expression) of a gene or target gene when the miRNA is expressed in the same cell as the gene or target gene. In one embodiment, a miRNA refers to a nucleic acid that has substantial or complete identity to a target gene and forms a single-stranded miRNA. In some embodiments miRNA may be in the form of pre-miRNA, wherein the pre-miRNA is double-stranded RNA. The sequence of the miRNA can correspond to the full length target gene, or a subsequence thereof. Typically, the miRNA is at least about 15-50 nucleotides in length (e.g., each sequence of the single-stranded miRNA is 15-50 nucleotides in length, and the double stranded pre-miRNA is about 15-50 base pairs in length). In some embodiments the miRNA is 20-30 base nucleotides. In some embodiments the miRNA is 20-25 nucleotides in length. In some embodiments the miRNA is 20, 21, 22, 23, 24, 25, 26, 27, 28, 29, or 30 nucleotides in length. (see, Griffiths-Jones S, Saini H K, van Dongen S, Enright A J., NAR 2008 36 (Database Issue):D154-D158; Griffiths-Jones S, Grocock R J, van Dongen S, Bateman A, Enright A J., NAR 2006 34 (Database Issue):D140-D144; Griffiths-Jones S. NAR 2004 32 (Database Issue):D109-D111; and Ambros V, Bartel B, Bartel D P, Burge C B, Carrington J C, Chen X, Dreyfuss G, Eddy S R, Griffiths-Jones S, Marshall M, Matzke M, Ruvkun G, Tuschl T. RNA 2003 9(3):277-279).

A given miRNA sequence includes both the human and murine homologues or orthologs having structural and functional similarity to the referenced miRNA. The term, homolog applies to the relationship between genes separated by the event of speciation (see ortholog) or to the relationship between genes separated by the event of genetic duplication (see paralog). Orthologous miRNAs are miRNAs in different species that are similar to each other because they originated from a common ancestor. Homologous sequences are similar sequences which share a common ancestral DNA sequence or which would have been expected to share such given their high degree of sequence identity. Accordingly, in some embodiments, the ortholog or homologue is any sequence which differs from the sequence of the referenced miRNA by at most one, two or three nucleic acid residues.

An inhibitor of a miRNA can be an antisense nucleic acid or siRNA which is complementary to or shares substantial identity with the miRNA and can block the function of the miRNA.

"Substantial identity" refers to a sequence that hybridizes to a reference sequence under stringent conditions, or to a sequence that has a specified percent identity over a specified region of a reference sequence.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization.

Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and Current Protocols in Molecular Biology, ed. Ausubel, et al.

The terms "substantially identical" or "substantial identity," in the context of two or more nucleic acids or polypeptide sequences, refer to two or more sequences or subsequences that are the same or have a specified percentage of amino acid residues or nucleotides that are the same (i.e., at least about 60%, preferably 65%, 70%, 75%, preferably 80%, 85%, 90%, or 95% identity over a specified region), when compared and aligned for maximum correspondence over a comparison window, or designated region as measured using one of the following sequence comparison algorithms or by manual alignment and visual inspection. This definition, when the context indicates, also refers analogously to the complement of a sequence. Preferably, the substantial identity exists over a region that is at least about 6-7 amino acids or 25 nucleotides in length, or more preferably over a region that is 50-100 amino acids or nucleotides in length, or the entire length. Preferable percent identities are at least 65%, 70%, 75%, preferably at least 80%, 85%, 90%, or 95% identity over the specified region For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions of a sequence. The segment can encompass an entire referenced sequence or be selected from the group consisting of from 10 to 600, 10 to 30, 20 to 600, about 50 to about 200, or about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The phrases "regulating expression of a target gene" or "regulation of gene expression" refer to the ability of a miRNA of the invention to regulate expression of the target gene. In some embodiments, gene regulation can include targeting of mRNAs for cleavage. In some embodiments gene regulation can include translational repression. To examine the extent of gene regulation, samples or assays of the organism of interest or cells in culture expressing a particular construct are compared to control samples lacking expression of the miRNA. Control samples (lacking construct expression) are assigned a relative value of 100%. Inhibition of expression of a target gene is achieved when the test value relative to the control is about 90%, preferably 50%, more preferably 25-0%. Suitable assays include, e.g., examination of protein or mRNA levels using techniques known to those of skill in the art such as dot blots, northern blots, in situ hybridization, ELISA, immunoprecipitation and enzyme function, as well as phenotypic assays known to those of skill in the art.

A "label" or a "detectable moiety" is a composition detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), digoxigenin, biotin, luciferase, CAT, beta galactosidase, GFP, or haptens and proteins which can be made detectable, e.g., by incorporating a radiolabel into the peptide or used to detect antibodies specifically reactive with the peptide.

"Biological sample" includes tissue; cultured cells, e.g., primary cultures, explants, and transformed cells; cellular extracts, e.g., from cultured cells, tissue, embryos, cytoplasmic extracts, nuclear extracts; blood, etc. Biological samples include sections of tissues such as biopsy and autopsy samples, and frozen sections taken for histologic purposes. A biological sample, including cultured cells, is typically obtained from a eukaryotic organism, most preferably a mammal such as a primate, e.g., chimpanzee or human; cow; dog; cat; a rodent, e.g., guinea pig, rat, mouse; rabbit; or a bird; reptile; or fish. iPS cells can be derived from any biological sample, including but not limited to those listed above.

"Nucleic acid" refers to deoxyribonucleotides or ribonucleotides and polymers thereof in single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The term "autologous" when used herein designates host derived and transplanted re-inserted, re-administered or returned to the host from which the nucleic acid, protein, cell or tissue was derived. Autologous can refer to nucleic acids, proteins, cells, or tissues derived from a host and transplanted, re-inserted, re-administered or returned to the host from which the nucleic acids, proteins or cells were derived.

The term "introducing" when used in the context of "introducing" a physiologically relevant miRNA into a cell refers to any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one miRNA into the host cell.

A variety of different types of cells can be utilized for the methods of the present invention. Cells that may express a microRNAs of the invention can include, e.g., fibroblast cells. The cells can be any of the cells typically utilized in generating cells that harbor recombinant nucleic acid constructs. Exemplary cells include, but are not limited to cells such as COS, CHO, HeLa, 293T and mouse embryonic fibroblasts (MEFs). Cell types utilized for the methods of the present invention can also include cells from tissue samples including but not limited to blood, bone, brain, kidney, muscle, spinal cord, nerve, endocrine system, uterine, ear, foreskin, liver, intestine, bladder or skin. The cells can include neural cells, lymphocytes, epidermal cells, islet cells, intestinal cells or fibroblasts. The cells of the present invention can be autologous or heterologous cells. The cells useful for the methods of the present invention can include animal cells. In some embodiments the cells are mammalian. In some embodiments the cell are from rodents or primates. In some embodiments the cells are mouse cells. In some embodiments the cells are human cells. In some embodiments the cells are diseased human cells, such as cancer cells. Cancer cells can include but are not limited to breast, prostate, liver, bladder, brain, blood or bone cancer cells.

The term "cell reprogramming" refers to altering the natural state of the cell such that the cell becomes pluripotent and is capable of dividing and differentiating into any cell type other than embryonic cells. Cellular reprogramming can include inducing pluripotency in or de-differentiation of the cell. Altering cell reprogramming can also refer to enhancing the level of pluripotency or de-differentiation that has been induced by an agent other than a microRNA. Pluripotent or multipotent cells, also called stem cells, have the ability to divide (self-replicate or self-renew) or differentiate into multiple different phenotypic lineages for indefinite periods; in some cases throughout the life of the organism. Under specific conditions, or in the present of optimal regulatory signals, pluripotent cells can differentiate and transform themselves into many different cell types that make up the organism. Pluripotent or multipotent cells may be distinguishable from progeny daughter cells by such traits as BrdU retention and physical location/orientation in the villus microenvironment, or any other methods well know to those of skill in the art. Multipotential or pluripotential stem cells possess the ability to differentiate into mature cells that have characteristic attributes and specialized functions, such as hair follicle cells, blood cells, heart cells, eye cells, skin cells, or nerve cells. A stem cell population is a population that possesses at least one stem cell. When pluripotent stem cells are derived from a non-pluripotent cell, such as for example a somatic cell, they are termed induced pluripotent stem cells (iPS or iPSCs). Cell reprogramming can further include partial de-differentiation to a closely related cell or cell type. Cell reprogramming can also include trans-differentiation. Trans-differentiation is defined as the conversion of one differentiated cell type into another, such as for example conversion of exocrine cells into beta-islet-like cells. (See, e.g., Blelloch, et al., Short cut to cell replacement, *Nature*, 455:604-605 (2008).)

The term "degenerative disease" refers to any disease wherein an individual would benefit from treatment with a pluripotent cell. Degenerative diseases include disease in which the function or structure of the affected tissue an/or organs progressively deteriorate over time. Examples of degenerative diseases include but are not limited to Parkinson's Disease, Alzheimer's Disease, skin grafts, Muscular Dystrophy, Amyotrophic Lateral Sclerosis (ALS) (e.g., Lou Gehrig's Disease), Multiple system atrophy, Niemann Pick disease, Atherosclerosis, Progressive supranuclear palsy, cancer, metabolic diseases (including for example but not limited to Tay-Sachs Disease), Diabetes, Heart Disease, Inflammatory Bowel Disease (IBD), Norrie disease, Prostatitis, Osteoarthritis, Osteoporosis, Rheumatoid Arthritis, Sickle Cell Anemia, heart disease, spinal and nerve related diseases and disorders, spinal and nerve related injuries, cancers (including for example but not limited to leukemias and lymphomas), other injuries induced by trauma, as well as regeneration of tissue post-resectioning.

In some embodiments, the invention provides a method of inducing pluripotency in an isolated cell by introducing an inhibitor of let-7 or an inhibitor of an miRNA of examples 5 and 6 into the cell, wherein the inhibitor (ii) affects cell reprogramming to induce pluripotency in the cell. In some further embodiments, a physiologically relevant miRNA is further introduced into the cell, wherein the relevant miRNA: (i) contains the seed sequence AAGUGCU (SEQ ID NO:15) or AAAGUGC (SEQ ID NO:16) or AAGUGC and (ii) affects cell reprogramming to induce pluripotency in the cell. For instance, the relevant miRNA can be a member of the embryonic stem cell cycle (ESCC) regulating miR-290 cluster, 302 cluster, 17-92 cluster, 106a, and 370 family of human microRNAs. In some embodiments, the relevant miRNA is a human or mouse or mammalian miRNA. The cell can also be a human cell. The relevant miRNA can also be (i) 80% or more identical to one of miR-291-3p (SEQ ID NO:1), miR-294 (SEQ ID NO:2), miR-295 (SEQ ID NO:3), miR-302d (SEQ ID NO:4), miR-292-3p (SEQ ID NO:5), hsa-miR-302a (SEQ ID NO:8), hsa-miR-302b (SEQ ID NO:9), hsa-miR-302c (SEQ ID NO:10), hsa-miR-302d (SEQ ID NO:11), hsa-miR-372 (SEQ ID NO:13), hsa-miR-373 (SEQ ID NO:14), hsa-miR-17 (SEQ ID NO:17), hsa-miR-20a (SEQ ID NO:18), hsa-miR-20b (SEQ ID NO:19), hsa-miR-93 (SEQ ID NO:20), hsa-miR-106a (SEQ ID NO:21), or hsa-miR-106b (SEQ ID NO:22); and contain the seed sequence AAGUGCU (SEQ ID NO:15) or AAAGUGC (SEQ ID NO:16) or AAGUGC; or be a miR-290 cluster member which is one or more of miR-291-3p (SEQ ID NO:1), miR-294 (SEQ ID NO:2) miR-295 (SEQ ID NO:3), miR-302d (SEQ ID NO:4), miR-292-3p (SEQ ID NO:5), hsa-miR-302a (SEQ ID NO:8), hsa-miR-302b (SEQ ID NO:9), hsa-miR-302c (SEQ ID NO:10), hsa-miR-302d (SEQ ID NO:11), hsa-miR371-5p (SEQ ID NO:12), hsa-miR-372 (SEQ ID NO:13), or hsa-miR-373 (SEQ ID NO:14). In some embodiments, the effect on reprogramming is to enhance reprogramming (e.g., the enhancement of cell reprogramming includes or constitutes enhancement of pluripotency or de-differentiation). The miRNA can also be an miRNA of Example 3 or Example 4 or their human orthologs. In some embodiments of any of the above, the cell was administered Oct4, Sox2, and Klf4 (OSK) or transfected so as to express Oct4, Sox2, and Klf4 (OSK). Isolated cell populations and cell cultures obtained by these methods are also contemplated wherein the cell(s) contain(s) one or more miRNAs containing the seed sequence AAGUGCU (SEQ ID NO:15) or AAAGUGC (SEQ ID NO:16) or AAGUGCU. Methods of treating an individual with a degenerative disease comprising administering to an individual a cell obtained by these methods are also contemplated by the invention. The degenerative disease can be one or more of Parkinson's Disease, Alzheimer's Disease, skin grafts, Muscular Dystrophy, Amyotrophic Lateral Sclerosis (ALS) (e.g., Lou Gehrig's Disease), Multiple system atrophy, Niemann Pick disease, Atherosclerosis, Progressive supranuclear palsy, cancer, metabolic diseases (including for example but not limited to Tay-Sachs Disease), Diabetes, Heart Disease, Inflammatory Bowel Disease (IBD), Norrie disease, Prostatitis, Osteoarthritis, Osteoporosis, Rheumatoid Arthritis, Sickle Cell Anemia, heart disease, spinal and nerve related diseases and disorders, cancers (including for example but not limited to leukemias and lymphomas), other injuries induced by trauma, or regeneration of tissue post-resectioning.

The preferred miRNA of Examples 3 and 4 for use according to the various embodiments and aspects of the invention are those listed in those examples which provide, as set forth in the tables of these examples, an average difference in effect which is at least 2-, 3-, 4-, 5-, 6-fold, or even 10-fold different from the values for mock treated cells. Preferred miRNA of Example 5 for use according to the various embodiments and aspects of the invention are those listed in the Table of Ex. 5 which provide an average difference in effect which is at least ½, ⅓, ¼, ⅕, ⅙ or even ⅒ of the values for mock treated cells.

EXAMPLES

Example 1

Embryonic Stem Cell Specific microRNAs Promote Induced Pluripotency

This work has now been published (see, Judson, R. et al., *Nat Biotech* 27(5):459-461 (2009) which is incorporated herein by reference in its entirety).
miRNAs Promote Induction of Pluripotency The miRNAs miR-291-3p, miR-294, or miR-295 along with retroviruses expressing Oct4, Sox2, and Klf4 (OSK) were introduced into mouse embryonic fibroblasts (MEFs) (See, e.g., Takahashi, K. & Yamanaka, S. *Induction of pluripotent stem cells from mouse embryonic and adult fibroblast cultures by defined factors* Cell 126:663-676 (2006)). The MEFs carried two reporters: an Oct4-GFP reporter that activates GFP with the induction of pluripotency and ubiquitous expression of a J-galactosidase/neo fusion from the Rosa26 locus. (See, e.g., Blelloch, R., Venere, M., Yen, J. & Ramalho-Santos, M. *Generation of induced pluripotent stem cells in the absence of drug selection* Cell Stem Cell 1:245-247 (2007)). MiRNAs were introduced on days 0 and 6 post-infection by transfection of synthesized double-stranded RNAs that mimic their mature endogenous counterparts. This method transiently recapitulates ES-like levels of the miR-290 cluster miRNAs (data not shown).

Figure 4:
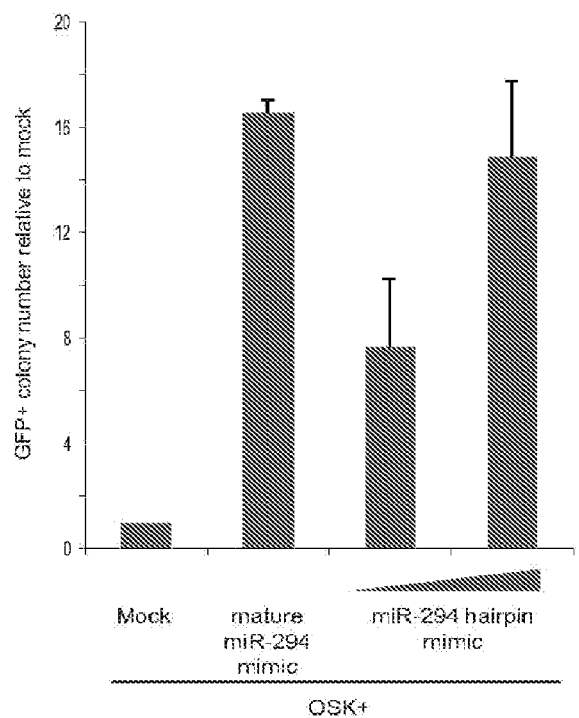
FIG. 4. Generation of GFP+ colonies with retroviruses expressing Oct4, Sox2, and Klf4 together with either duplex miR-294 mimic (16 nM), hairpin miR-294 mimic (16 nM and 160 nM) or transfection reagent only (mock). Error bars indicate standard deviation of N=3.

OSK plus miR-291-3p, miR-294, or miR-295 consistently increased the number of Oct4-GFP+ colonies as compared to controls transduced with OSK plus transfection reagent (FIG. 1a). The miR-294 mimic showed the greatest effects, increasing efficiency from 0.01-0.05% to 0.1-0.3% of transduced MEFs. Introduction of a chemically synthesized miR-294 pre-miRNA similarly enhanced reprogramming (FIG. 4). Two other members of the miR-290 cluster that are not ESCC miRNAs, miR-292-3p and miR-293, did not increase colony number (FIG. 1a). The ESCC miRNAs share a conserved seed sequence, which largely specifies target mRNAs (FIG. 1b). MiR-302d, a member of another miRNA cluster that has the same seed sequence also enhanced reprogramming (FIGS. 1b&c). Mutation of the seed sequence in miR-294 blocked the increase in colony number (FIGS. 1b&c). In summary, together with Oct4, Sox2, and Klf4, the ESCC miRNAs and related miRNAs with a common seed sequence (AAGUGCU; SEQ ID NO:15) promote the de-differentiation of fibroblasts into Oct4-GFP+ES cell-like colonies.

Effect of Mixtures of miRNAs on Induction of Pluripotency

Figure 5:
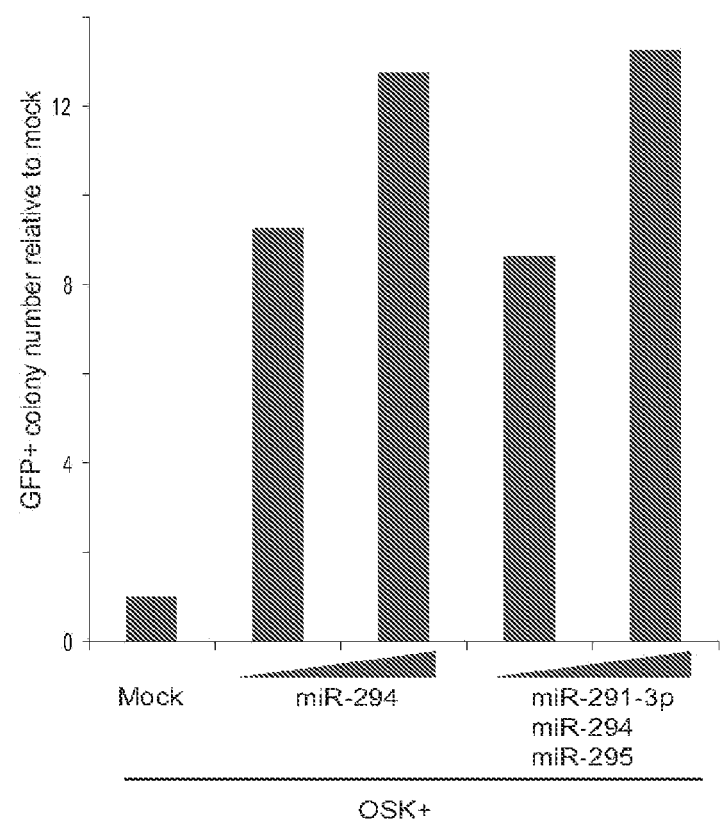
FIG. 5. Effect of combining ESCC miRNAs on reprogramming. Generation of GFP+ colonies with retroviruses expressing Oct4, Sox2, and Klf4 (OSK) together with either miR-294 (16 nM or 48 nM) or a mixture of miR-291-3p, miR-294 and miR-295 (5.3 nM each or 16 nM each) or transfection reagent only (mock).

Consistent with previous observations that ESCC miRNAs act redundantly (Wang, Y. et al. Embryonic stem cell-specific microRNAs regulate the G1-S transition and promote rapid proliferation. *Nat Genet* 40, 1478-1483 (2008)), mixes of the different ESCC miRNAs did not further enhance reprogramming efficiency (FIG. 5).

Studies Regarding miR-294 miRNA

Figure 6:
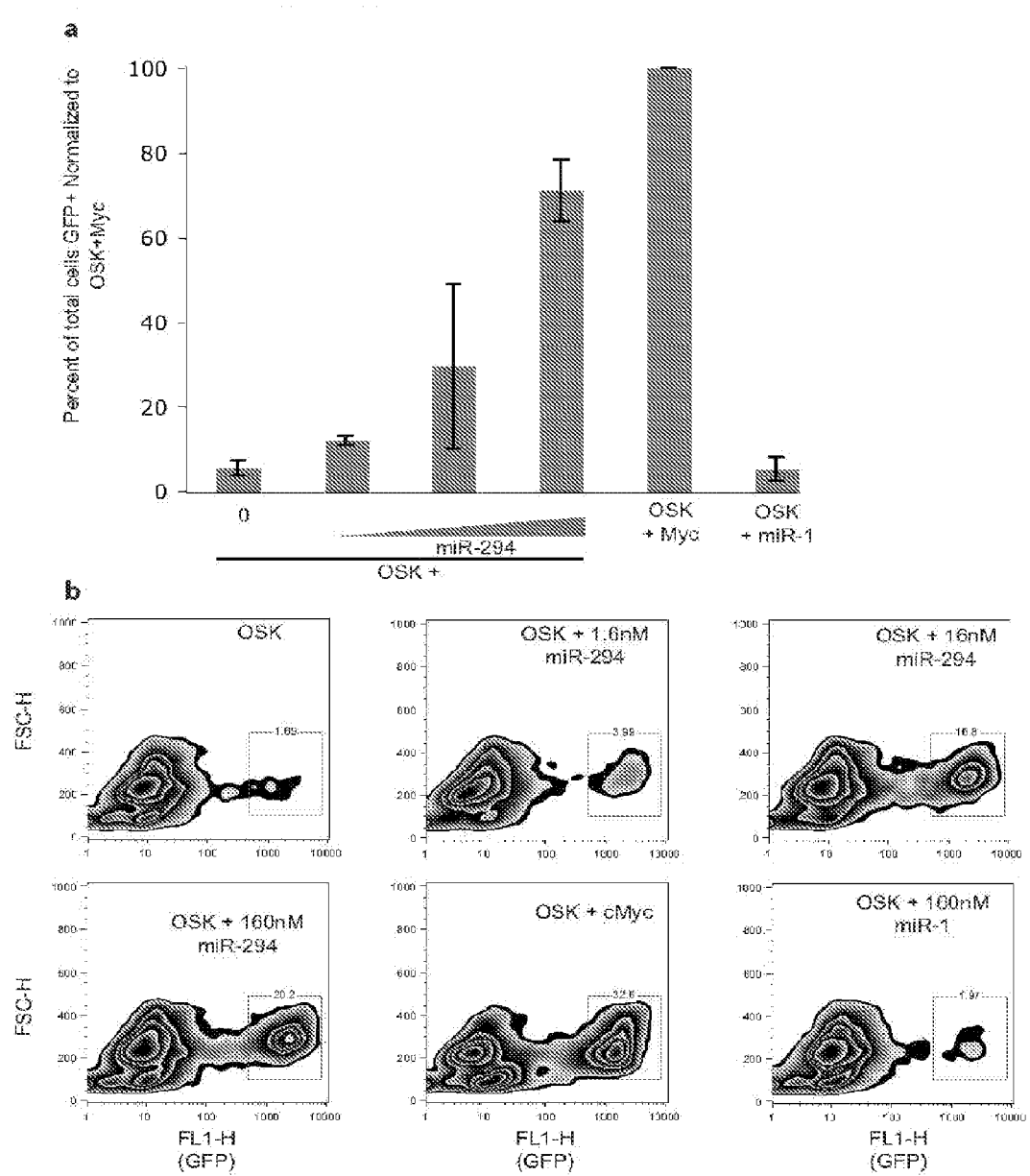
FIG. 6. FACS analysis of GFP+ cells from MEFs infected with Oct4, Sox2, and Klf4 (OSK) and transfected with miRNA mimics. (a) Graphic display of FACS analysis for GFP+ sorted cells on day 12. Wedge indicates increasing concentrations (1.6, 16 and 160 nM) of mimic. N=3. Error bars indicate standard deviation. (b) FACS plots of representative samples.
Figure 7:
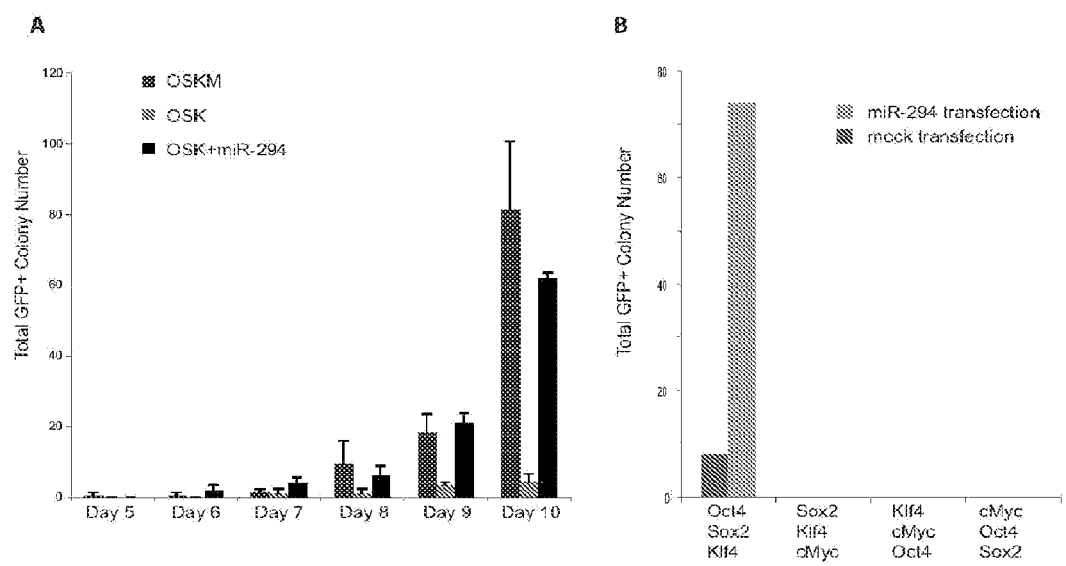
FIG. 7. Kinetics of reprogramming and effects of miR-294 on other combinations of transcription factors. (a) Generation of GFP+ colonies with retroviral expression of Oct4, Sox2, and Klf4 alone (OSK), with the addition of cMyc (OSKM), or with transfection of 16 nM miR-294 mimic (OSK+miR-294). GFP+ colonies were counted on days 5-10. GFP+ microcolonies were reliably first seen in OSKM and OSK+miR-294 by day 7 with identifiable GFP+ES-like colonies seen by day 9. GFP+ microcolonies and ES-like colonies were generally seen in OSK on days 8 and 10, respectively. Error bars represent standard deviation for N=3. (b) Generation of GFP+ colonies with combinations of retroviruses expressing Oct4, Sox2, Klf4 or cMyc with and without transfection of miR-294 (16 nM). Lane 1 depicts a single experiment representative of many (Table 2). Lanes 2, 3 and 4 depict N=1, 1, and 3, respectively.

Therefore, further studies focused on miR-294. Increasing doses of miR-294 further enhanced Oct4-GFP+ colony formation and the Oct4-GFP+ cellular fraction (FIG. 1d & FIG. 6). At the highest doses, miR-294 increased the number of colonies to approximately 75 percent of that achieved with OSK and cMyc (OSKM) (0.4-0.7% of starting MEFs) (FIG. 1d). Addition of miR-294 mimic increased the kinetics of OSK reprogramming to rates comparable to OSKM reprogramming (FIG. 7a). Transfection of miR-294 did not further enhance the reprogramming efficiency of any other three-factor combination or OSKM (FIG. 1c & FIG. 7b). Therefore, miR-294 substituted for, but did not further enhance, cMyc's contribution to reprogramming efficiency.

Figure 8:
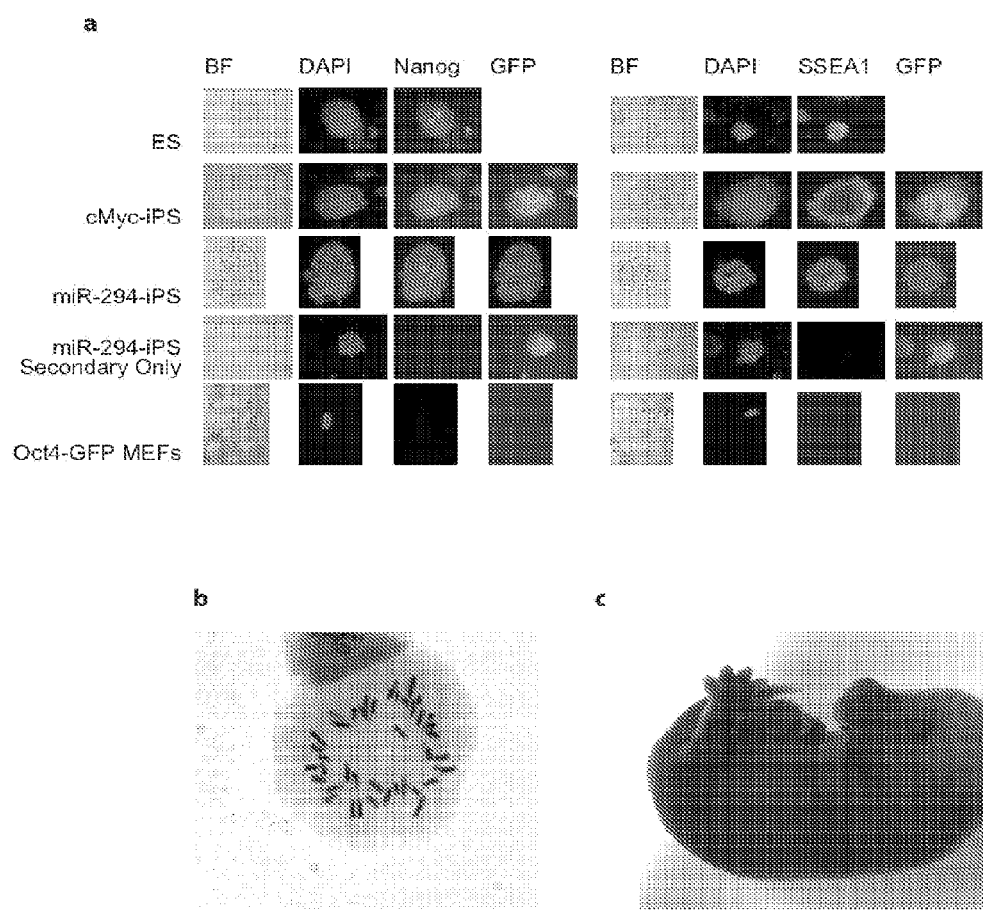
FIG. 8. Verification of miR-294-iPS pluripotency. (a) Brightfield and immunofluorescent photographs of miR-294-iPS colonies. Images are representative of six independent iPS lines. Staining controls include ES (V6.5) cells, cMyc-iPS colonies, miR-294-iPS colonies with secondary antibody only, and MEFs (b) Representative karyotype of iPS cells induced with Oct4, Sox2, Klf4 and miR-294 mimic. (c) An E15 chimera derived from blastocyst injection of miR-294-iPS cells carrying a ubiquitously expressed—galactosidase reporter.

ES-like Oct4-GFP+ colonies induced by OSK and miR-294 (miR-294-iPS) were expanded and verified as induced pluripotent stem (iPS) cells. MiR-294-iPS lines expressed endogenous Oct4, Sox2, and Klf4, while retrovirus expression was silenced (FIGS. 1e & f). Colonies showed an ES-like morphology and stained positively for the ES cell markers, Nanog and SSEA-1 (FIG. 8a). The cell lines had normal karyotypes and efficiently induced teratoma formation with differentiation down all three germ layers (FIG. 8b & FIG. 9a-c). Injection of miR-294-iPS cells into blastocysts resulted in high-grade chimeras, with contribution of donor iPS cells to all three germ layers, and to germ line (FIGS. 1g-h & FIG. 8c).

Mechanisms of miRNA Substitutes for cMyc Reprogramming

Figure 2:
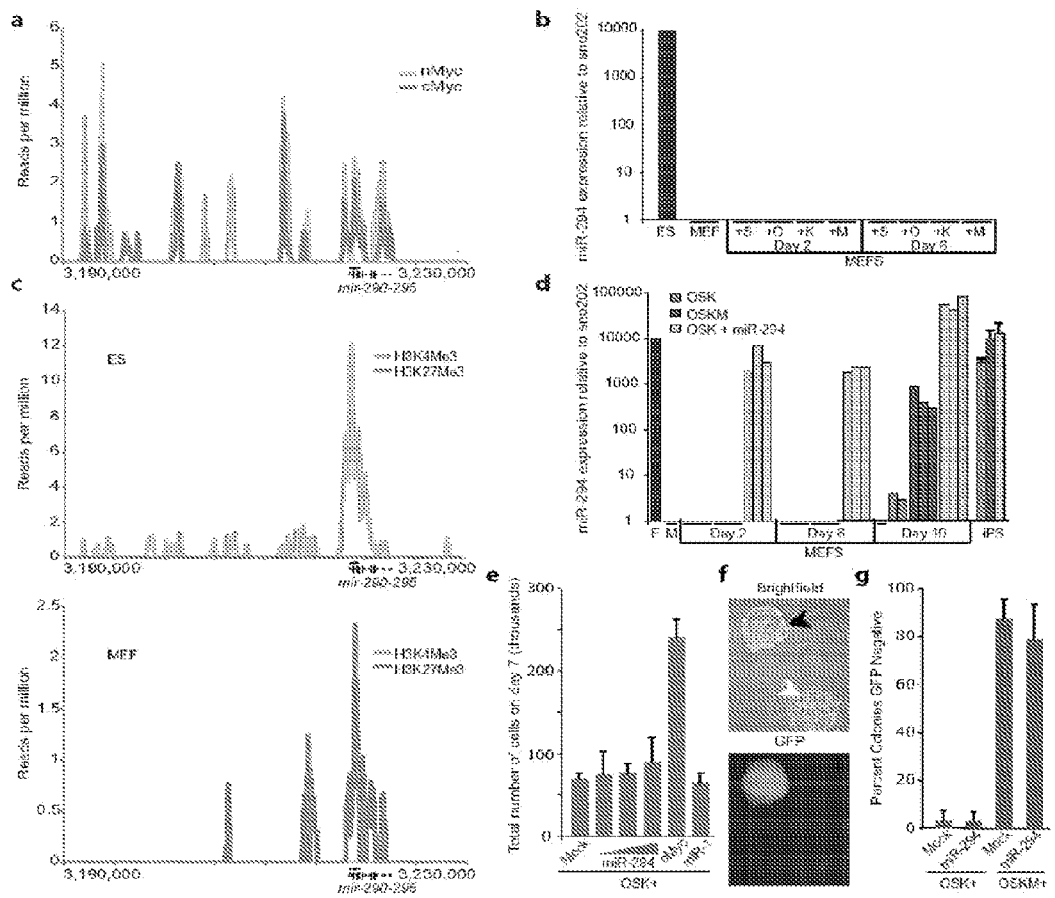
FIG. 2. Characterization of the relationship between Myc and miR-294. (a) cMyc (blue) and nMyc (yellow) bind the miR-290 cluster promoter. ChIP-seq data reads (Chen, X. et al., Integration of external signaling pathways with the core transcriptional network in embryonic stem cells. Cell 133, 1106-1117 (2008)) were aligned to the mm9 assembly of the genome and peaks were generated with Findpeaks (Fejes, A. P. et al. FindPeaks 3.1: a tool for identifying areas of enrichment from massively parallel short-read sequencing technology. *Bioinformatics* 24, 1729-1730 (2008)). Vertical hash marks denote the positions of the miR-290 cluster miRNAs. (b) Quantitative RT-PCR for total mature miR-294 expression in control (V6.5) ES cells, MEFs, and MEFs infected with viruses expressing Sox2 (S), Oct4 (O), Klf4 (K) or cMyc (M). RNA was collected on days 2 and 6. N=3. Horizontal black bars indicate Ct>40. Sno202 was used as input control. Data was normalized to ES cells. (c) H3K4me3 (green) and H3K27me3 (red) surrounding the miR-290 cluster in MEFs. Chip-seq data (Mikkelsen, T. S. et al. Genome-wide maps of chromatin state in pluripotent and lineage-committed cells. *Nature* 448, 553-560 (2007)) were analyzed as described in a. (d) Quantitative RT-PCR for total mature miR-294 expression in control (V6.5) ES cells (E), MEFs (M), MEFs infected with either Oct4, Sox2, Klf4 (OSK); Oct4, Sox2, Klf4, and cMyc (OSKM); or OSK+miR-294, and established iPS lines resulting from these conditions (iPS). RNA was collected on days 2, 6, and 10 of reprogramming. Three independent experiments are shown. Horizontal black bars indicate Ct>40. Sno202 was used as input control. Data was normalized to ES cells. (e) Total cell number during reprogramming. Cells were counted on day 7 after infection with OSKM or OSK+/−miRNA mimic. Concentrations of miR-294 mimic: 1.6, 16 and 160 nM. Concentration of miR-1 mimic: 160 nM. (f) GFP negative colonies in presence of cMyc. Oct4-GFP+, ES-like colonies (black arrow) and GFP-negative, non-ES-like colonies (white arrow). (g) Quantification of number of day 10 GFP-negative colonies after infection with OSKM or OSK+/−miR-294 mimic. All error bars indicate standard deviation of N=3.

The mechanism for how ESCC miRNAs substitutes for cMyc in reprogramming is not entirely clear. However, bioinformatic analysis of ES ChIP-seq data (Chen, X. et al. Integration of external signaling pathways with the core transcriptional network in embryonic stem cells. *Cell* 133, 1106-1117 (2008)) showed that both c-Myc and n-Myc bind to the promoter region of the miR-290 cluster (FIG. 2a). Oct4, Sox2 and Nanog have also been reported to bind the promoter of the miR-290 cluster (Marson, A. et al. Connecting microRNA genes to the core transcriptional regulatory circuitry of embryonic stem cells. *Cell* 134, 521-533 (2008)). Transduction of cMyc, Oct4, Sox2, or Klf4 expressing retrovirus individually failed to induce expression of the miR-290 cluster in fibroblasts (FIG. 2b). Analysis of ChIP-seq data (Mikkelsen, T. S. et al. Genome-wide maps of chromatin state in pluripotent and lineage-committed cells. *Nature* 448, 553-560 (2007)) for different histone modifications (FIG. 2c) showed that the miR-290 promoter is H3K27 methylated in MEFs, a modification associated with transcriptional silencing. In contrast, the promoter is H3K4 methylated in ES cells, a modification associated with transcriptional activity. Therefore, these transcription factors likely can only induce the expression of the miR-290 cluster as cells replace promoter-associated H3K27 with H3K4 methylation during the reprogramming process. Indeed, with OSKM transduction, miR-294 was robustly activated late in the reprogramming process, similar to the reported timing for expression of endogenous Oct4, and other critical members of the core ES machinery (FIG. 2d) (Stadtfeld, M., Maherali, N., Breault, D. T. & Hochedlinger, K. Defining molecular cornerstones during fibroblast to iPS cell reprogramming in mouse. *Cell Stem Cell* 2, 230-240 (2008); Brambrink, T. et al. Sequential expression of pluripotency markers during direct reprogramming of mouse somatic cells. *Cell Stem Cell* 2, 151-159 (2008)). These data suggest that miR-294 is downstream of cMyc, but requires epigenetic remodeling for expression.

Figure 9:
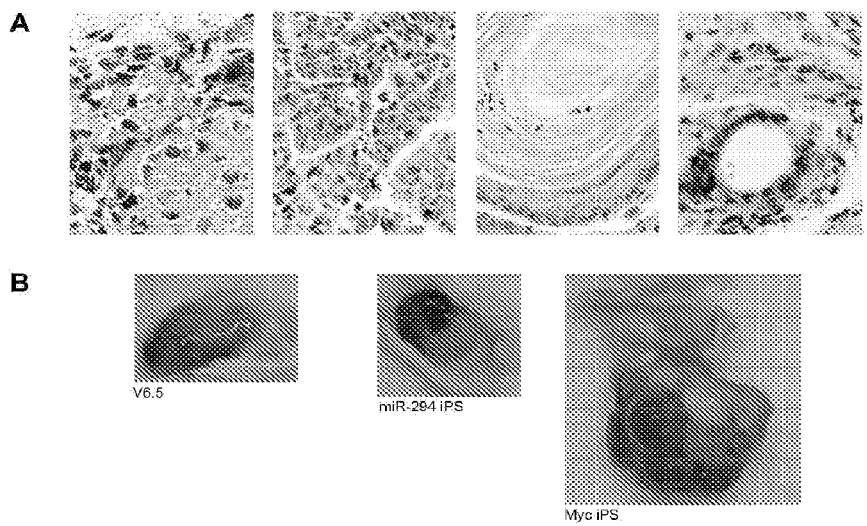
FIG. 9. Teratoma generation from V6.5, miR-294-iPS, and cMyc-iPS cell lines. (A) H&E staining of miR-294-iPS derived teratomas. Images depict, left to right, bone, neural tissue, keratinizing squamous epithelial tissue, and glandular tissue. (B) Left and Middle, images of representative control ES (V6.5) and miR-294-iPS noninvasive teratomas. Right, image of representative cMyc-iPS invasive teratoma. (C) Number of invasive and noninvasive tumors with different cell lines injected. Columns display from left to right, independent cell lines, number of mice injected, number of total teratomas isolated, number of total teratomas found to be invasive, and the number of days after injection teratomas were harvested. Percent teratoma refers to the percentage of cell lines that formed teratomas. Percent invasive refers to the percentage of teratomas found to be invasive, defined as migration through the underlying body wall.

The downstream effects of the ESCC miRNAs versus cMyc on the reprogramming process were not identical. Unlike cMyc, miR-294 did not promote proliferation of MEFs early in the reprogramming process (FIG. 2e). Furthermore, as previously reported, approximately 80% of the OSKM colonies failed to express Oct4-GFP and lacked ES-like morphology (FIGS. 2f & g) (Nakagawa, M. et al. Generation of induced pluripotent stem cells without Myc from mouse and human fibroblasts. *Nat Biotechnol* 26, 101-106 (2008)). In contrast, OSK+miR-294 produced a predominantly uniform population of ES-like GFP+ colonies. The Oct4-GFP-colonies were induced by cMyc, not inhibited by miR-294, as the introduction of both produced a similar number of GFP-, non-ES-like colonies as cMyc alone (FIG. 2g). Finally, when cells were injected into immunodeficient mice to produce teratomas, more than a third of the teratomas resulting from cMyc-iPS cells invaded into the underlying body wall, while none of teratomas resulting from miR-294-iPS cells did so (FIG. 9 b&c). These findings show that while miR-294 can substitute for cMyc to enhance reprogramming, its effects on the cell population are not identical.

In summary, our data show that miRNAs can replace cMyc in promoting the de-differentiation of somatic cells into induced pluripotent stem cells. An exciting possibility is that other small RNAs could replace additional factors, which together with other approaches may eventually substitute for the use of introduced DNA elements. Additionally, further analysis of the targets of these miRNAs may offer valuable insights into the mechanism of reprogramming. The ESCC miRNAs are highly expressed in ES cells where they promote progression through the ES cell cycle, by accelerating the transition through the G1/S restriction point Wang, Y. et al. Embryonic stem cell-specific microRNAs regulate the G1-S transition and promote rapid proliferation. *Nat Genet* 40, 1478-1483 (2008)). Their expression is downregulated with ES cell differentiation as the G1 phase of the cell cycle extends (Houbaviy, H. B., Murray, M. F. & Sharp, P. A. Embryonic stem cell-specific MicroRNAs. *Dev Cell* 5, 351-358 (2003); Orford, K. W. & Scadden, D. T. Deconstructing stem cell self-renewal: genetic insights into cell-cycle regulation. *Nat Rev Genet* 9, 115-128 (2008)). ESCC miRNAs have also been shown to induce the expression of the de novo methyltransferases in ES cells, although how this may promote self-renewal is unclear (Sinkkonen, L. et al. MicroRNAs control de novo DNA methylation through regulation of transcriptional repressors in mouse embryonic stem cells. *Nat Struct Mol Biol* 15, 259-267 (2008); Benetti, R. et. al. A mammalian microRNA cluster controls DNA methylation and telomere recombination via Rbl2-dependent regulation of DNA methyltransferases. *Nat Struct Mol Biol* 15, 998 (2008)). As a target of Myc, the miR-290 cluster likely acts downstream, but only after erasure of silencing histone modifications within its promoter. cMyc certainly has additional targets, reflected in the differences in outcomes between the introduction of cMyc and miR-294.

The ESCC miRNAs share a common seed sequence with a larger family of small RNAs known to promote cellular proliferation (Takahashi, K. & Yamanaka, S. Induction of pluripotent stem cells from mouse embryonic and adult fibroblast cultures by defined factors. *Cell* 126, 663-676 (2006)). This family includes "onco-miRs", such as members of the miR-17 cluster, miR-106, and miR-302 miRNAs (Mendell, J. T. miRiad roles for the miR-17-92 cluster in development and disease. Cell 133, 217-222 (2008); Voorhoeve, P. M. et al. A genetic screen implicates miRNA-372 and miRNA-373 as oncogenes in testicular germ cell tumors. Cell 124, 1169-1181 (2006)). These miRNAs, like the ESCC miRNAs, may be acting by enhancing cell cycle progression and promoting de-differentiation of the cells. Such parallels between induced de-differentiation and cancer will be an exciting area of future pursuit.

Materials and Methods

Cell Culture:

MEF isolation: E13.5 embryos were washed in HBSS. Heads and visceral tissues were removed, washed in fresh HBSS, briefly rinsed with 70% ethanol, then submerged in 0.05 mM trypsin/1 mM EDTA HBSS solution and incubated at 37° C. for 10 minutes. Embryos were pipetted repeatedly to aid in tissue dissociation, then added to MEF media containing 10% FBS and plated (passage 0). iPS lines were maintained in ES media+15% knock-out serum on irradiated MEF feeders or gelatin.

Retrovirus Infection:

The retroviral packaging vector pCL-ECO was transfected into 293T cells simultaneously with pMXs vectors containing either Oct4, Sox2, Klf4, or cMyc cDNA using Fugene 6 (Roche) (Takahashi, K. & Yamanaka, S. Induction of pluripotent stem cells from mouse embryonic and adult fibroblast cultures by defined factors. Cell 126, 663-676 (2006)). At 24 hours, the media was changed, and at 48 hours, the media was collected, filtered (0.45 ⌈M), and frozen in aliquots at −80° C. Retrovirus was never thawed more than once. To induce reprogramming, passage 3 Oct4-GFP MEFs were plated on gelatin at 3,000 cells per cm2. Virus-containing media was added 24 hours later (Day 0). Cells were transfected with 1.6, 16 or 160 nM microRNA mimics (Dharmacon) with Dharmafect (Dharmacon) on days indicated as according to manufacturers' protocol. MiR-294 seed sequence mutant contained mature sequence aaauuucuucccuuuugugugu. Media was changed daily. Media was replaced with ES media+15% FBS on day 2, and ES media+15% knock-out serum replacement (Invitrogen) on day 6. To determine total cell number cells were trypsinized on day 7, counted, and passaged onto irradiated MEF feeders. GFP+ colonies were counted between days 10-12 and FACS sorted (BD FACSCalibur) on day 12. Percent efficiency was calculated as the fraction of colonies relative to total MEFs infected. P-value of colony number was calculated using standard t-test. Individual iPS colonies were picked between days 10 and 15.

Immunohistochemistry:

iPS lines were grown in a 24-well plate, fixed with 4% paraformaldehyde and washed in 1×PBS with 0.1% Triton x-100 (PBT). PBT with 2% BSA and 1% goat-serum was used to block for one hour before addition of primary antibodies against SSEAI (DSHB: MC-480) and Nanog (Abcam: ab21603), which were incubated overnight at 4° C. Cells were washed with PBT, blocked with PBT with 2% BSA and 10% goat-serum for 1 hour before addition of secondary antibodies (Invitrogen: Alexa Fluor 594 goat anti-rabbit IgG and Biolegend: PE anti-mouse IgM).

Quantitative real-time PCR: Total RNA was isolated using TRizol (Invitrogen), polyadenylated (NEB), and DNase treated (Invitrogen), according to manufacturers' protocols. Reverse transcription was performed using the Superscript III kit (Invitrogen). Random hexamers were used for mRNA analysis. Real-time quantitative PCR for mRNA was conducted with SYBR Green PCR master mix (Applied Biosystems) according to the manufacturers' protocol using the following primer sets: Rex1, (gattgtggagccatacattgca (SEQ ID NO:278), tgccgtagcctcgcttgt (SEQ ID NO:279)), Nanog (gctcagcaccagtggagtatcc (SEQ ID NO:280), tccagatgcgttcaccagatag (SEQ ID NO:281)), Endogenous Oct4 (tctttccaccaggcccccggctc (SEQ ID NO:282), tgcgggcggacatggggagatcc (SEQ ID NO:283)) (Takahashi, K. & Yamanaka, S. Induction of pluripotent stem cells from mouse embryonic and adult fibroblast cultures by defined factors. Cell 126, 663-676 (2006)), Endogenous Sox2 (tagagatagactccgggcgatga (SEQ ID NO:284), ttgccttaaacaagaccacgaaa (SEQ ID NO:285)) (Takahashi, K. & Yamanaka, S. Induction of pluripotent stem cells from mouse embryonic and adult fibroblast cultures by defined factors. Cell 126, 663-676 (2006)), Endogenous Klf4 (gaattgtgtttcgatgatgc (SEQ ID NO:286), tcgcttcctcttcctccgacaca (SEQ ID NO:287)), Lin28 (agtctgccaagggtctggaa (SEQ ID NO:288), cgctcactcccaatacagaaca (SEQ ID NO:289)), Exogenous Oct4 (tctcccatgcattcaaactg (SEQ ID NO:290), cttttattttatcgtcgacc (SEQ ID NO:291)), Exogenous Klf4 (cctacacatgaagaggcac (SEQ ID NO:292), cttttattttatcgtcgacc (SEQ ID NO:293)), Exogenous Sox2 (ctgccctgtcgcacatgtg (SEQ ID NO:294), cttttattttatcgtcgacc (SEQ ID NO:295)), cMyc (cagaggaggaacgagctgaagcgc (SEQ ID NO:296), ttatgcaccagagtttcgaagctgttcg (SEQ ID NO:297)) and RPL7 (gattgtggagccatacattgca (SEQ ID NO:298), tgccgtagcctcgcttgt (SEQ ID NO:299)). Real-time quantitative PCR for microRNAs was conducted using the Taqman approach as previously described (Tang, F., Hajkova, P., Barton, S. C., Lao, K. & Surani, M. A. MicroRNA expression profiling of single whole embryonic stem cells. Nucleic Acids Res 34, e9 (2006))

Teratoma Formation:

iPS lines were grown on irradiated MEFs or gelatin, trypsinized, and resuspended in PBS. One million iPS cells were injected subcutaneously per side in severe combined immunodeficient (SCID) mice (NCI-Frederick). Tumors were removed when they reached a size of 1-1.5 cm in long diameter, fixed in 10% formalin, embedded in paraffin, sectioned, and H&E stained.

Blastocyst Injection and Chimera Formation:

Super-ovulation of B6D2F1/Cr females (NCI-Frederick) was induced via PMSG injection (d0) and hCG injection (d2). On d2, females were crossed to B6D2F1/Cr males, oocytes were isolated on d3, washed in M2 media (Specialty Media) and grown in KSOM media (Specialty Media) for three days. IPS cells were first karyotyped as previously described. 8-12 cells were injected into cultured blastocysts, which were then transplanted into the uteri of pseudo-pregnant Swiss-Webster females. Embryos were collected on E15 and stained as previously described.

Mir-290 Promoter Analysis:

Previously published ChIP-seq data for c-Myc, n-Myc, H3K4me3, and H3K27me3 were downloaded as fastq files and aligned to the mm9 (NCBI Build 37.1) assembly of the mouse genome using Eland (GA Pipeline 1.0, Illumina). The mm9 assembly contains the mir-290 locus, which was missing from previous assemblies. Following alignment, peak scores were assigned using the Findpeaks 3.1.9.2 algorithm. The peak scores were normalized to the number of genome-mapping sequence reads.

Example 2

Let-7 and ESCCs Regulate Self-Renewal

Figure 10:
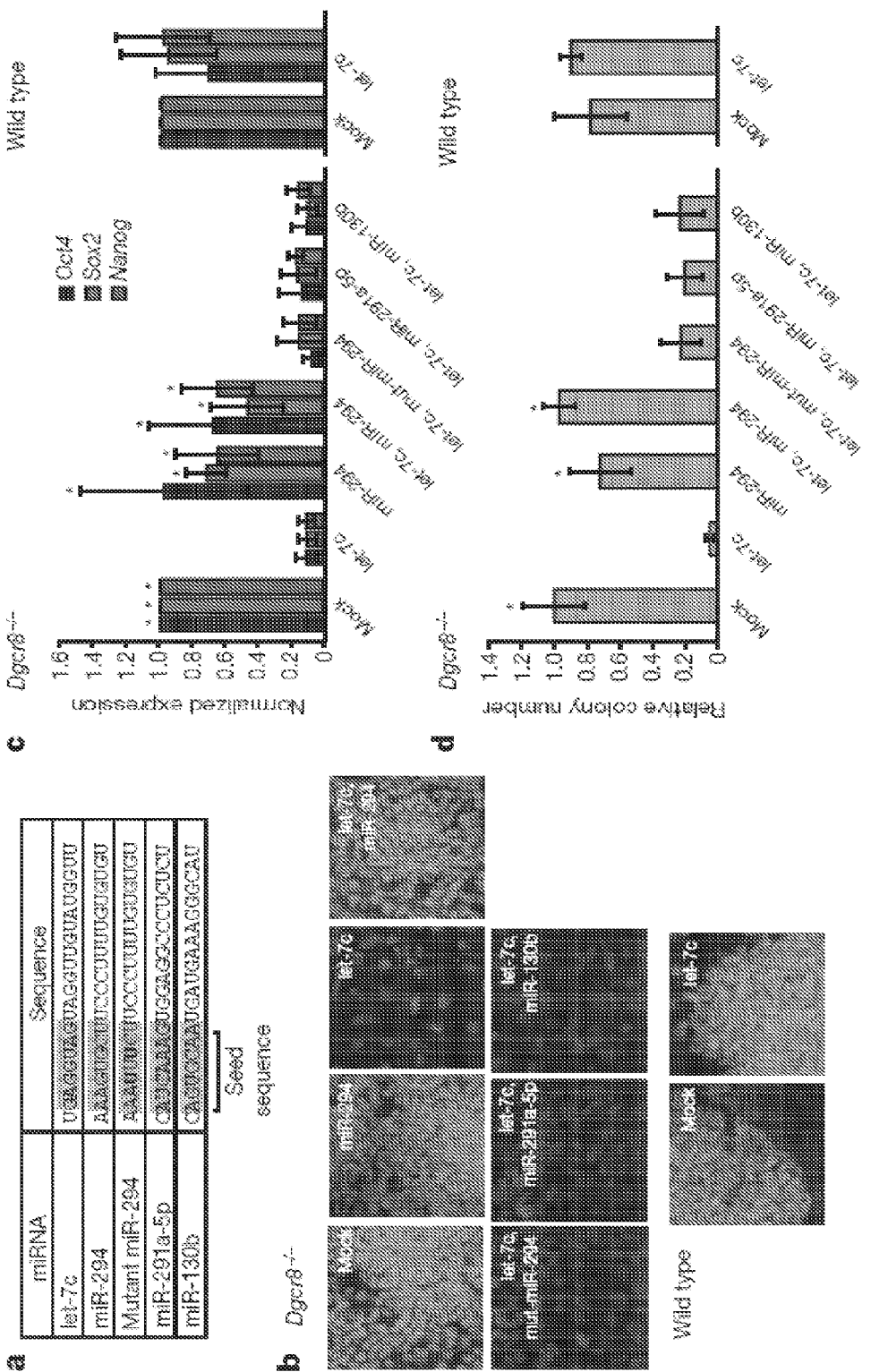
FIG. 10. The let-7 and ESCC miRNA families have opposing roles in regulating ESC self-renewal. (a) Transfected miRNAs (SEQ ID NOS:90, 2, 7, 275 and 276, respectively) with the seed sequence highlighted. (b) Pou5fl/Oct4 immunofluorescence staining after transfection of let-7c, miR-294 and combinations of let-7c with miR-294, mutant-miR-294, miR-291a-5p, or miR-130b in Dgcr8−/− (i) and wild-type (ii) ESCs. Representative images, n=3. (c) qRT-PCR for Pou5fl/Oct4, Sox2, and Nanog normalized to beta-actin after miRNA introduction as in b. n=3-8. * indicates p<0.02. (d) Colony reforming assays after miRNA introduction as in b and c. n=3. * indicates p<0.05. All p-values generated by Bonferroni corrected t-test of comparisons to let-7c treated. Error bars represent standard deviation.
Figure 15:
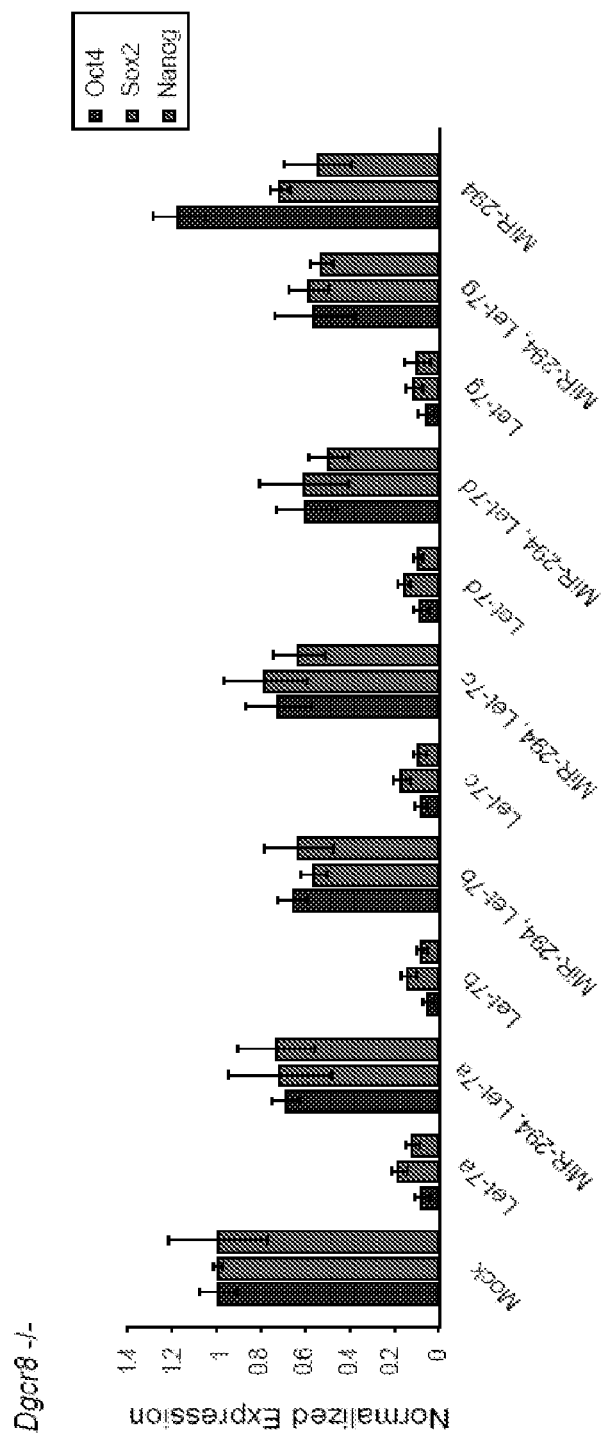
FIG. 15. The let-7 family of miRNAs function to suppress self-renewal in Dgcr8−/− ESCs. qRT-PCR for Oct4, Sox2, and Nanog normalized to beta-actin after transfection with different let-7 family members either alone or in combination with miR-294. n=3, error bars represent standard deviation FIG. 16. miR-290 cluster ESCC family members function to suppress let-7c induced silencing of ESC self-renewal in Dgcr8−/− ESCs. qRT-PCR for Oct4, Sox2, and Nanog normalized to beta-actin after transfection with different ESCC family members either alone or in combination with let-7c. n=3, error bars represent standard deviation.

The let-7 miRNAs are broadly expressed across differentiated tissues (Landgraf, P. et al. Cell 129:1401-1414 (2007);

Chen, C. et al. *Mamm. Genome* 18:316-327 (2007)) and are tightly regulated during ESC differentiation (Rybak, A. et al. *Nat Cell Biol* 10:987-93 (2008); Viswanathan, S. R. et al., *Science* 320:97-100 (2008); Heo, 1. et al. *Mol Cell* 32:276-84 (2008 Newman, M. A. et al., *RNA* 14:1539-49 (2008); Thomson, J. M. et al. *Genes Dev* 20:2202-7 (2006)). To test the hypothesis that let-7 miRNAs could rescue the capacity of Dgcr8−/− ESCs to silence ESC self-renewal when induced to differentiate, we introduced mimics of a representative let-7 family member, let-7c, into the Dgcr8−/− ESCs (FIG. 10a). Let-7c silenced the ESC self-renewal program even when the ESCs were maintained in ESC culture conditions. Three days after treatment with let-7c, Dgcr8−/− cells downregulated ESC associated markers including alkaline phosphatase activity, Pou5fl/Oct4 immunofluorescence staining), and mRNA expression of Pou5fl/Oct4, Sox2, and Nanog (data not shown). Furthermore, the transfected cells showed a diminished capacity to reform ESC colonies in replating assays, a functional test of ESC self-renewal capacity (FIG. 10d, panel i). Similar effects were observed with the introduction of let-7a, let-7b, let-7d, and let-7g (FIG. 15) and these effects were observed over a range of concentrations, including levels normally found in more differentiated cell types (data not shown).

Figure 16:
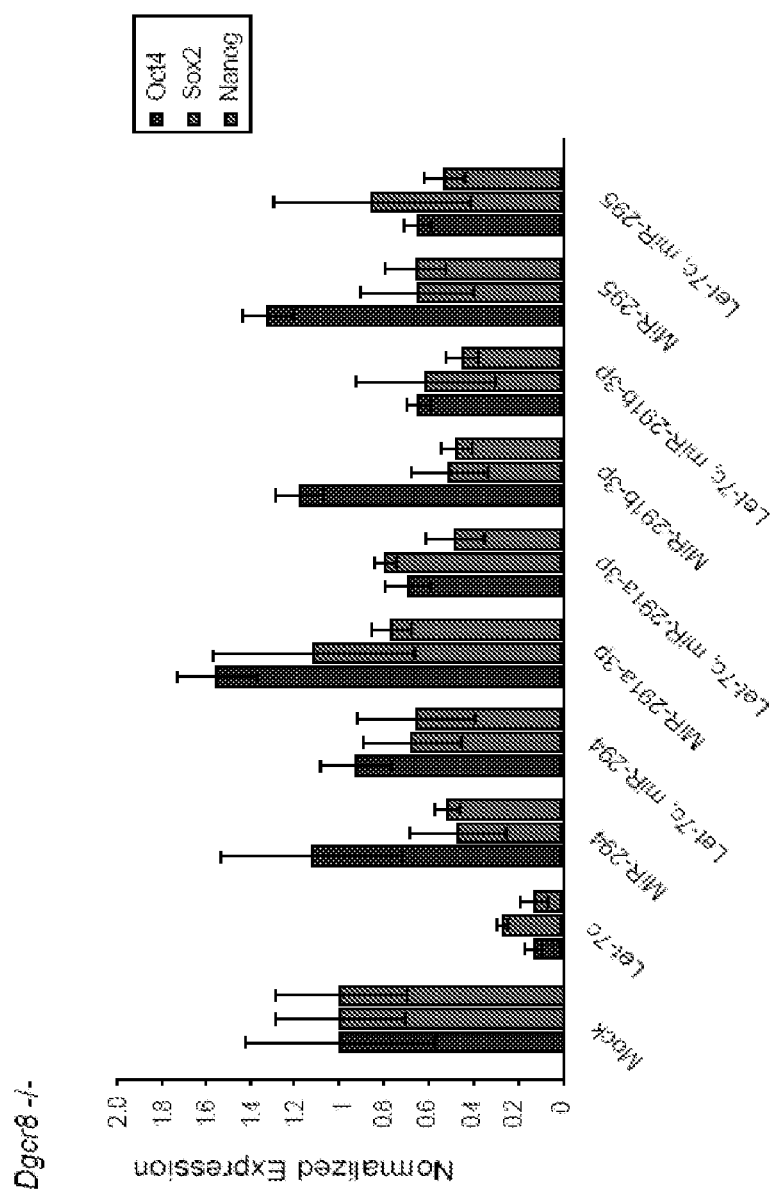

In contrast to the Dgcr8−/− ESCs, wild-type ESCs were resistant to let-7c (FIG. 1b-d, panel ii). This finding suggested that other miRNAs normally expressed in wild-type ESCs inhibit let-7c-induced suppression of self-renewal. The ESCC miRNAs are likely candidates as they make up a majority of miRNA molecules in mouse ESCs (Marson, A. et. al. Cell 134:521-33 (2008); Calabrese, J. M., *Proc. Natl. Acad. Sci. U.S.A* 104:18097-18102 (2007)), they are rapidly downregulated upon differentiation coincident with the upregulation of mature let-7 (data not shown), and they promote the ESC fate (Wang, Y. et al. *Nat Genet* 40:1478-83 (2008); Judson, R. et al., *Nat Biotech* (2009); Benetti, R. et al., *Nat Struct Mol Biol* 15 (3):268-279 (2008); Sinkkonen, L. et al., *Nat Struct Mol Biol* 15 (3):259-267 (2008)). Therefore, we introduced a representative member of this family, miR-294, to test if it could block let-7c-induced suppression of Dgcr8−/− ESC self-renewal. Three days after co-introduction of miR-294 and let-7c, Dgcr8−/− ESCs retained alkaline phosphatase activity (data not shown), Pou5fl/Oct4 immunofluorescence staining (FIG. 10b, panel i), and mRNA expression of Pou5fl/Oct4, Sox2, and Nanog (FIG. 10c, panel i). Furthermore, miR-294 rescued the colony forming capacity of the Dgcr8−/− ESCs (FIG. 10d, panel i). Control miR-NAs (miR-294 with a seed mutation and other ESC expressed miRNAs, miR-291a-5p and miR-130b, that do not contain the ESCC miRNA seed sequence) did not antagonize the effects of let-7c (FIG. 10a-d) showing that miR-294's effect is not simply secondary to competition for RISC complexes. Other members of the ESCC family miR-291a-3p, miR-291b-3p, and miR-295 were similarly able to block the effects of let-7c (FIG. 16). These data indicate that the let-7 and ESCC families of miRNAs have opposing roles in the maintenance of ESC self-renewal.

Targeting Through ORFs and 3'UTRs

Figure 1:
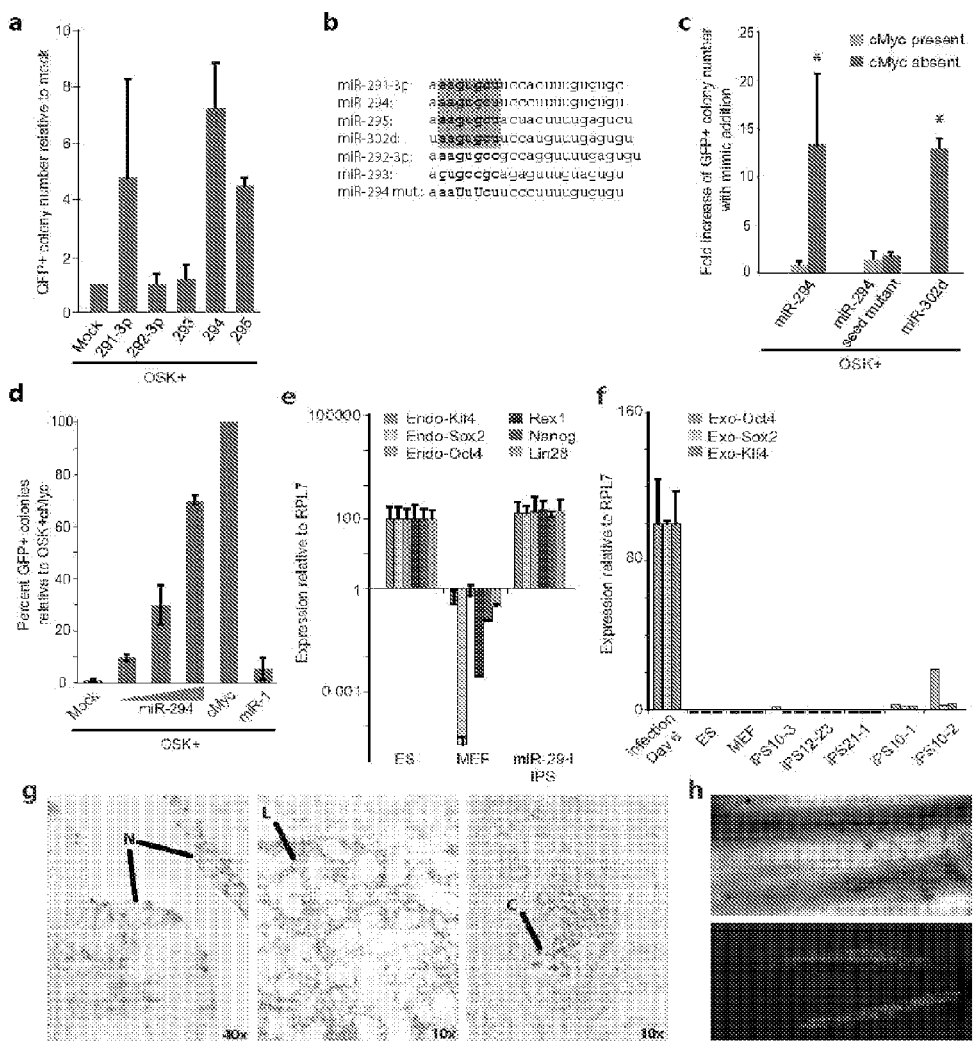
FIG. 1. The ESCC miRNAs promote three-factor, but not four-factor induced pluripotency. (a) Fold increase of day 10 Oct-GFP+ colonies with retroviruses expressing Oct4, Sox2, and Klf4 (OSK) together with 16 nM miRNA mimic relative to transfection reagent only (Mock). N=3. Raw data in Table 1. (b) Sequence of miR-290 cluster (SEQ ID NOS:1-3, 5 and 6, respectively), miR-302d (SEQ ID NO:4), and miR-294 seed sequence mutant (SEQ ID NO:7). Bold indicates seed sequence. Capitals indicate point mutations. Grey box highlights ESCC seed-sequence. (c) Fold increase in day 10 Oct4-GFP+ colonies with addition of mimic to OSK in the presence (light grey) or absence (dark grey) of cMyc retrovirus. Bars represent the number of GFP+ colonies after mimic transfection divided by the number of GFP+ colonies after mock transfection. N=6, 26, 2, 5, & 3 left to right. Asterisk indicates p-value≤0.0001. Raw data for bars 1&2 in Table 2. (d) Percent day 10 Oct4-GFP colonies for OSK plus 1.6, 16 and 160 nM transfected miR-294 mimic or 160 nM miR-1 relative to OSKM. (e) Quantitative RT-PCR for endogenous pluripotency markers in control (V6.5) ES cells, MEFs, and miR-294-iPS lines. N=3, 3, & 5. RPL7 was used as input control. Data was normalized to ES expression. (f) Quantitative RT-PCR for exogenous Oct4, Sox2, and Klf4 in MEFs 6 days after viral infection, control (V6.5) ES cells, and MEFs (each N=3) and 5 individual miR-294-iPS lines. Horizontal black bars indicate Ct>40. RPL7 was used as input control. Data was normalized to MEF expression 6 days after viral infection. (g) X-gal staining demonstrates miR-294-iPS chimeric contribution to ectoderm (neural tissue, N), endoderm (lung, L), and mesoderm (cartilage, C). (h) GFP expression in genital ridges of E12.5 chimera demonstrates Oct4-GFP miR-294-iPS contribution to germline. All error bars indicate standard deviation.
Figure 11:
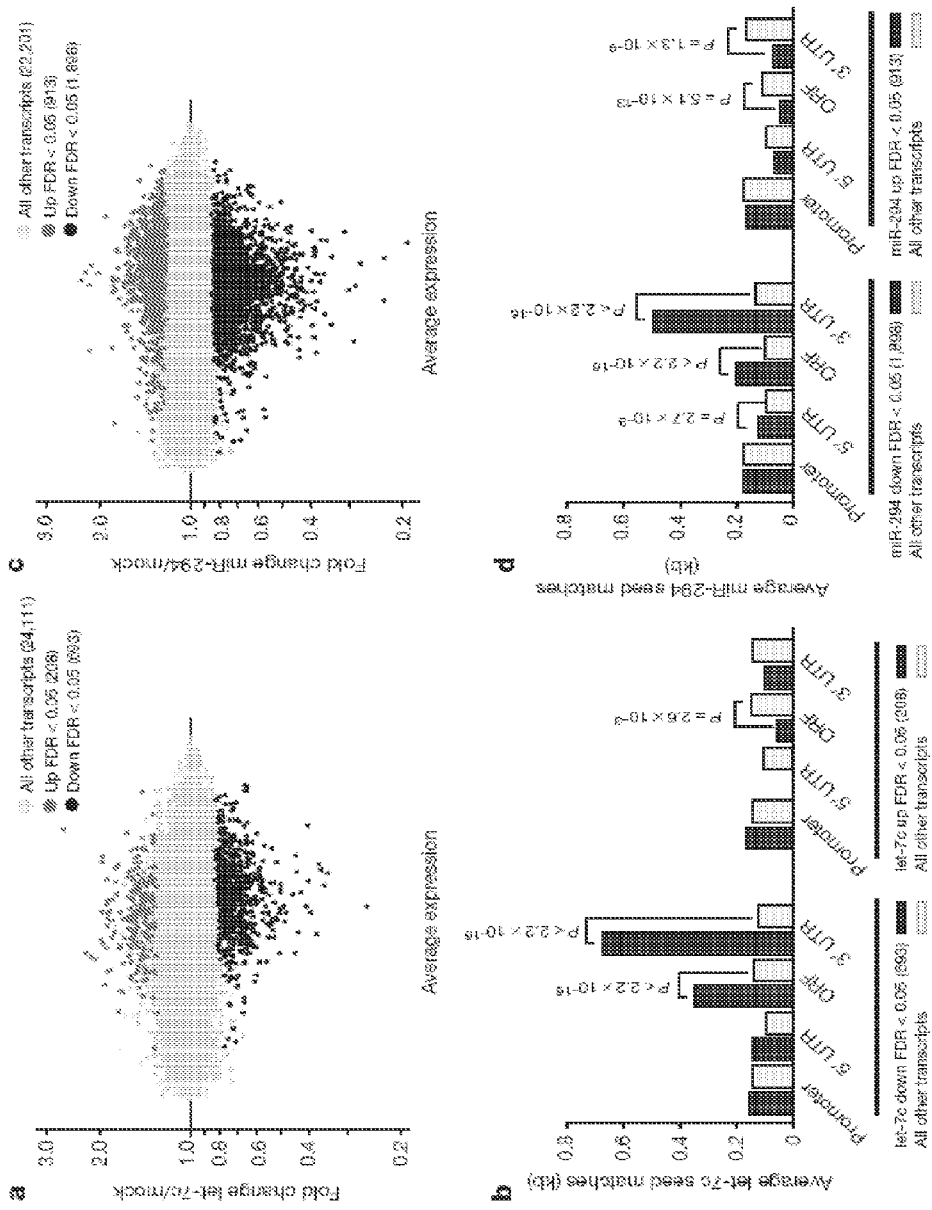
FIG. 11. The let-7 and ESCC miRNAs suppress hundreds of transcripts by binding their ORF and/or 3'UTR. (a) Microarray analysis following introduction of let-7c alone. Upregulated transcripts are shown in dark grey, downregulated transcripts in black (FDR<0.05). (b) Analysis of seed matches in the promoter, 5'UTR, ORF, and 3'UTR of let-7c-downregulated and upregulated transcripts. Presented are the mean number of seeds matches per kb of sequence for the listed groups of altered genes described in a. P-values calculated by the Wilcoxon Rank Sum Test and Bonferroni corrected are shown for p<0.01 (c) Microarray analysis following introduction of miR-294 alone. Color labeling, as in a. (d) Seed analysis as in b for miR-294 up and downregulated transcripts.

The functional antagonism between let-7c and miR-294 on ESC self-renewal suggested opposing roles for these miR-NAs on downstream molecular targets. To test this prediction, we sought to globally identify these targets using mRNA microarrays following the introduction of let-7c or miR-294 into Dgcr8−/− ESCs. The introduction of the let-7c mimic led to downregulation of 693 and upregulation of 208 transcripts relative to mock treated cells with a false discovery rate (FDR) less than 5% (FIG. 11a, Table S1). Of the 693 downregulated transcripts, 294 contained a let-7c 7mer seed match in the 3'UTR, 287 contained a 7mer seed match in the ORF, and 113 contained both 3'UTR and ORF seed matches (Table S1). The presence of these seed matches in the downregulated transcripts was highly enriched compared to the entire gene set (FIG. 11b, FIG. S6a). Similarly, the introduction of miR-294 led to a large number of upregulated and downregulated transcripts (FIG. 1 c, Table S1). Again, downregulated transcripts were enriched for seed matches in the 3'UTR and ORF. In contrast, upregulated transcripts were depleted for seed matches in the 3'UTR and ORF (FIGS. 11b&d). These findings suggest that miR-294 and let-7c functionally act through the down-regulation of many targets by binding their ORF and/or 3'UTR.

Impact on ESC Transcriptional Network

To further investigate the mechanism for the opposing roles of let-7c and miR-294 on ESC self-renewal, we performed pathway analysis on the miRNA regulated transcript sets. Specifically, we searched for overlaps between the miRNA-regulated transcripts and genes identified by chromatin immunoprecipitation (ChIP) of pluripotency associated transcription factors (Marson, A. et al. *Cell* 134:521-33 (2008); Chen, X. et al. *Cell* 133:1106-17 (2008)). This analysis measures whether there is any influence of the let-7 or ESCC miRNAs on the transcription factors themselves (FIG. 12a, i&ii) or the transcripts originating from the genes bound by the transcription factors (FIG. 12a, iii).

In ESCs, two Myc family members—nMyc and cMyc—are highly expressed and have largely overlapping ChIP target genes (Chen, X. et al. *Cell* 133:1106-17 (2008)). cMyc has previously been identified as a let-7 target in cancer cells (Kumar, M. S. et al., *Nat Genet* 39:673-677 (2007)), and we find that nMyc is significantly downregulated by let-7c in our array data (not shown). Consistent with let-7 directly targeting the Myc family, overlapping let-7c-regulated transcripts with Myc-bound genes showed an enrichment of Myc target genes in the let-7c-downregulated transcript set and a depletion in the let-7c-upregulated transcript set (FIG. 12b, Box I). Furthermore, the enrichment was independent of the presence of seed sequence matches within the ORF or 3'UTR. This finding suggests that let-7 is acting directly through Myc (cMyc and/or nMyc) rather than through Myc's downstream target genes (FIG. 12a, i).

Performing a similar analysis overlapping miR-294-regulated transcripts and Myc target genes showed the exact opposite pattern as the analysis with let-7c-regulated transcripts. There was a depletion for Myc targets in the miR-294-downregulated transcript set and an enrichment in the miR-294-upregulated transcript set (FIG. 12b, Box II). This pattern suggests that miR-294 upregulates Myc activity (FIG. 12a, ii). Indeed, microarray data showed that miR-294 dramatically increased cMyc levels (data not shown). As miR-294 itself suppresses its downstream targets (FIG. 11d), the upregulation of cMyc must be indirect, through an unknown intermediate repressor (FIG. 12a, ii). These data show that the let-7 and ESCC families of miRNAs have opposing effects on Myc activity.

Figure 12:
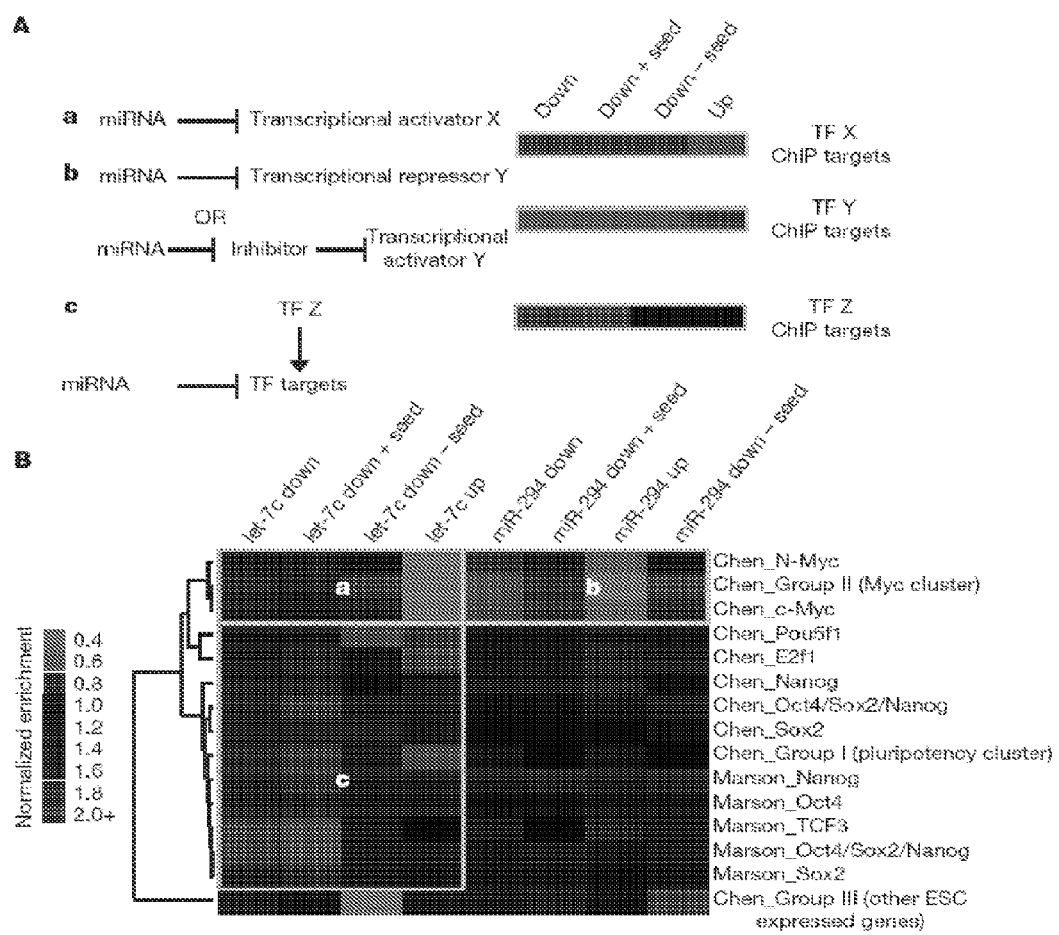
FIG. 12. Enrichment/depletion of transcription factor bound genes among miRNA-regulated transcripts. (a) A schematic of hypothetical miRNA regulation of a transcription factor or its targets. Corresponding expected enrichment/depletion of the transcription factor ChIP targets in miRNA-induced upregulated or downregulated transcript sets are displayed in a heat map. A key of color coding representing relative enrichment is given in b. (b) A heat map showing enrichment of the ChIP targets among the different sets of miRNA-regulated transcripts on the horizontal axis. Vertical axis represents the different ChIP data sets with first author and factor that was immunoprecipitated.

Overlap of the let-7c-regulated transcripts with ChIP target genes for the pluripotency transcription factors, Pou5fl/Oct4, Sox2, Nanog, and Tcf3 once again showed an enrichment among let-7c-downregulated transcript set (FIG. 12b, Box III). However, this enrichment was limited to the downregulated transcripts with seed matches in their ORF or 3'UTR. These data suggest that rather than directly regulating the pluripotency transcription factors, let-7 targets transcripts originating from the genes bound by them (FIG. 12a, iii). This pattern of enrichment is most clear for the ChIP target genes bound by Tcf3, cobound by Pou5fl/Oct4, Sox2, and Nanog, or bound by Chen et al.'s pluripotency cluster (a group of targets bound by Pou5fl/Oct4, Sox2, Nanog, Smad1, and STAT3). The latter results agree with recent reports showing that genes bound by multiple pluripotency transcription factors are more likely to be transcriptionally activated (Chen, X. et al. *Cell* 133:1106-17 (2008); Kim, J. et al., *Cell* 132:1049-61 (2008)). There was no enrichment in the overlap between the miR-294-regulated transcripts and Pou5fl/Oct4, Sox2, Nanog, and Tcf3 bound genes. These data suggest that let-7c inhibits downstream targets of these pluripotency factors while miR-294 has no obvious effects on either the transcription factors themselves or on their downstream targets.

Opposing Regulation of Myc, Lin28, and Sal14

Having discovered that Myc activity was alternatively downregulated and upregulated by let-7c and miR-294, we sought to identify other factors that might be similarly regulated by these miRNAs. Indeed, gene ontology analysis showed an enrichment for ESC enriched genes among the let-7c-downregulated and miR-294-upregulated transcript sets (not Table S2). 88 transcripts were regulated in opposing directions by let-7c and miR-294, of which 44 contained a let-7c seed match (data not shown). Notably, this set of transcripts included the well-known pluripotency genes Lin28 and Sal14. Lin28 is an RNA binding protein that inhibits let-7 processing (Rybak, A. et al. *Nat Cell Biol* 10:987-93 (2008); Viswanathan, S. R. et al., *Science* 320:97-100 (2008); Heo, I. et al. *Mol Cell* 32:276-84 (2008); Newman, M. A. et al., *RNA* 14:1539-49 (2008); Piskounova, E. et al. *J Biol Chem* 283: 21310-4 (2008)), but not transfected let-7 mimic (data not shown). Sal14 is a transcription factor that promotes ESC self-renewal (Lim, C. Y. et al. *Cell Stem Cell* 3:543-54 (2008); Wu, Q. et al. *J Biol Chem* 281:24090-4 (2006); Zhang, J. et al. *Nat Cell Biol* 8:1114-23 (2006)). These findings show that the let-7 and ESCC families antagonistically regulate multiple genes with described roles in ESC self-renewal.

Figure 13:
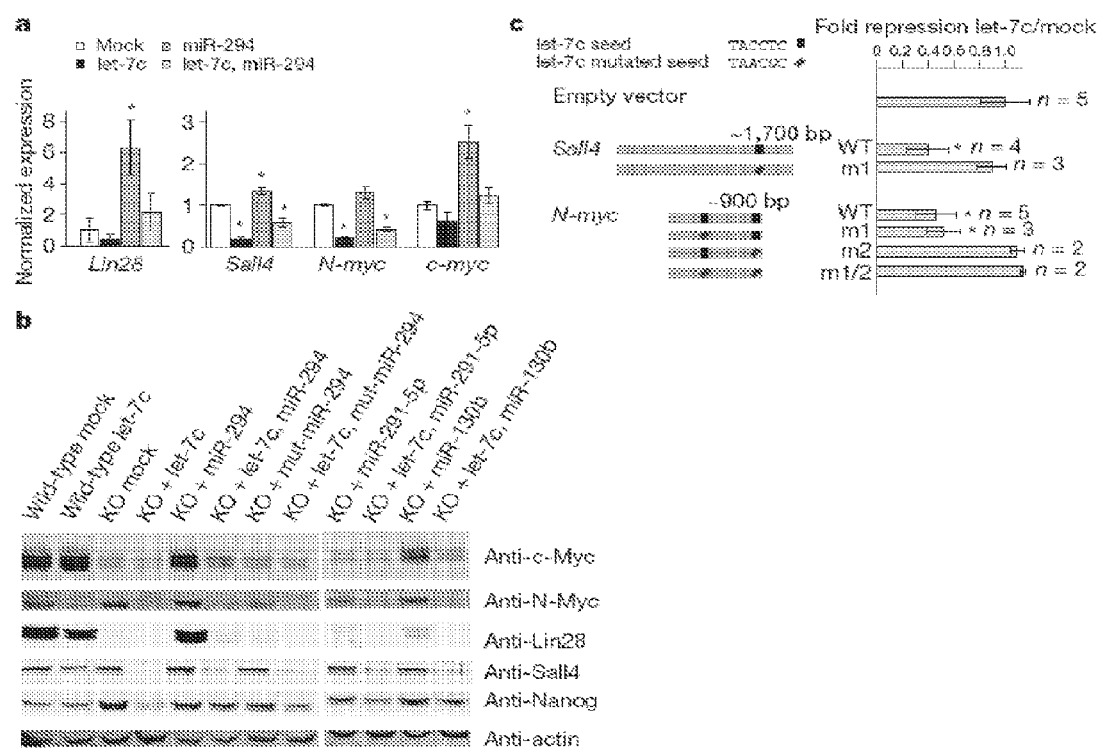
FIG. 13. Let-7c and miR-294 regulate Lin28, Sa114, cMyc, and nMyc. (a) qRT-PCR for Lin28, Sa114, nMyc, and cMyc 12 hours after transfection with let-7c, miR-294, or a combination of the two. n=3. (b) Representative Western blot analysis 48 hours after transfection with miRNAs. (c) Luciferase analysis of Sa114 and nMyc 3'UTRs. Seed matches for let-7c in the 3'UTRs along with different mutant constructs are diagrammatically represented in the left panel. Luciferase results after co-transfection with let-7c mimic relative to mock transfected are shown in the right panel. All data are represented as mean+/− standard deviation. * indicates p<0.05 by Bonferroni corrected t-test.

To verify our genomic analysis, we performed qRT-PCR, Western analysis, and reporter assays for a subset of the genes. qRT-PCR confirmed the opposing effects of let-7c and miR-294 on Lin28, Sal14, nMyc, and cMyc mRNA levels with a combination of the two miRNAs showing intermediate levels (FIG. 13a). Western analysis showed similar results (FIG. 13b). Of note, cMyc protein was dramatically reduced in Dgcr8-/- versus wild-type ESCs and was brought back to wild-type levels with the introduction of miR-294. MiR-294 had little effect on nMyc levels. In contrast, let-7c had little effect on cMyc, yet dramatically reduced nMyc levels. Therefore, the cumulative effect of the miRNAs on total Myc (cMyc+nMyc) protein levels followed a strong pattern of opposing regulation. Similarly, the miRNAs showed significant opposing effects on Lin28 and Sal14 protein levels. Lin28 and cMyc are known targets of let-7 (Rybak, A. et al. *Nat Cell Biol* 10:987-93 (2008); Kumar, M. S. et al., *Nat Genet* 39:673-677 (2007)), and luciferase assays confirmed that nMyc and Sal14 are also direct targets (FIG. 13c).

Considering that cMyc was dramatically reduced in Dgcr8-/- cells and then increased with miR-294, we considered the possibility that the loss of cMyc alone could largely explain the sensitivity of Dgcr8-/- cells to let-7-induced silencing of ESC self-renewal. To test this possibility, we generated and evaluated cMyc-/- ESCs. The loss of cMyc led to decreased expression of Pou5fl/Oct4 relative to the parental cell line (data not shown). Introduction of let-7c into the cMyc-/- cells decreased the expression levels of Sox2 and Nanog (data not shown). However, levels were not reduced to the same degree as seen with the introduction of let-7c into Dgcr8-/- cells. These results indicate that the decrease of cMyc in Dgcr8-/- cells alone cannot explain the sensitivity of these cells to let-7-induced silencing of ESC self-renewal.

Inhibition of Let-7 Promotes De-Differentiation

Figure 17:
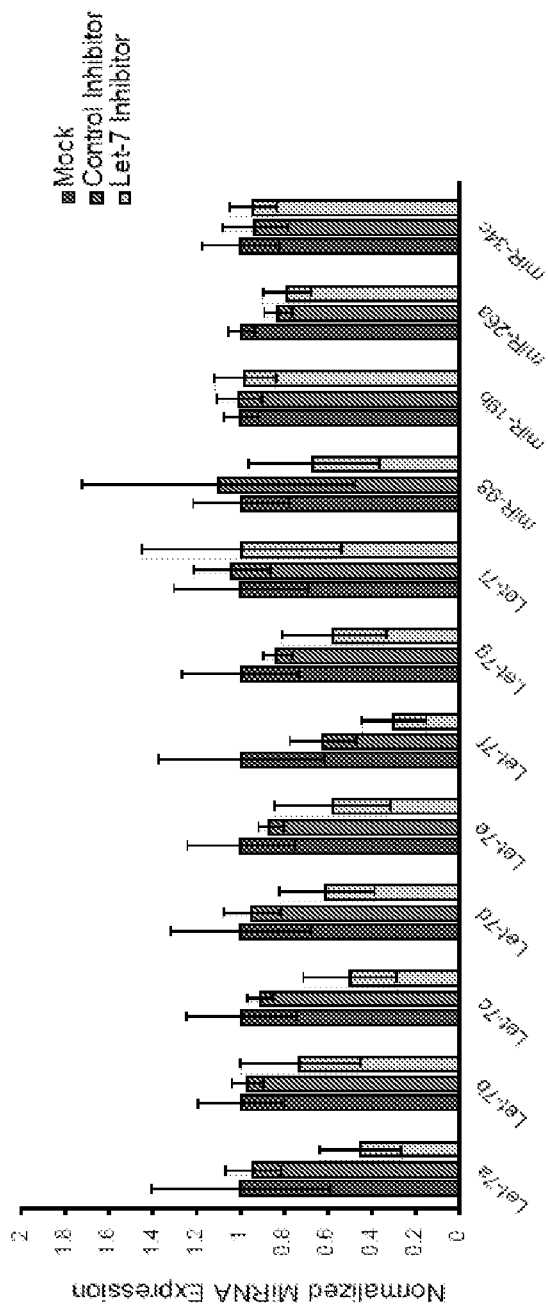
FIG. 17. The let-7 inhibitor reduces levels of the majority of mature let-7 family miRNAs. polyA miRNA qPCR was performed in mock, control inhibitor, and let-7 inhibitor treated MEFs. Let-7 family miRNAs but not other highly expressed miRNAs (miR-19b, miR-26a, and miR-34c) have reduced levels in the presence of the let-7 inhibitor.
Figure 18:
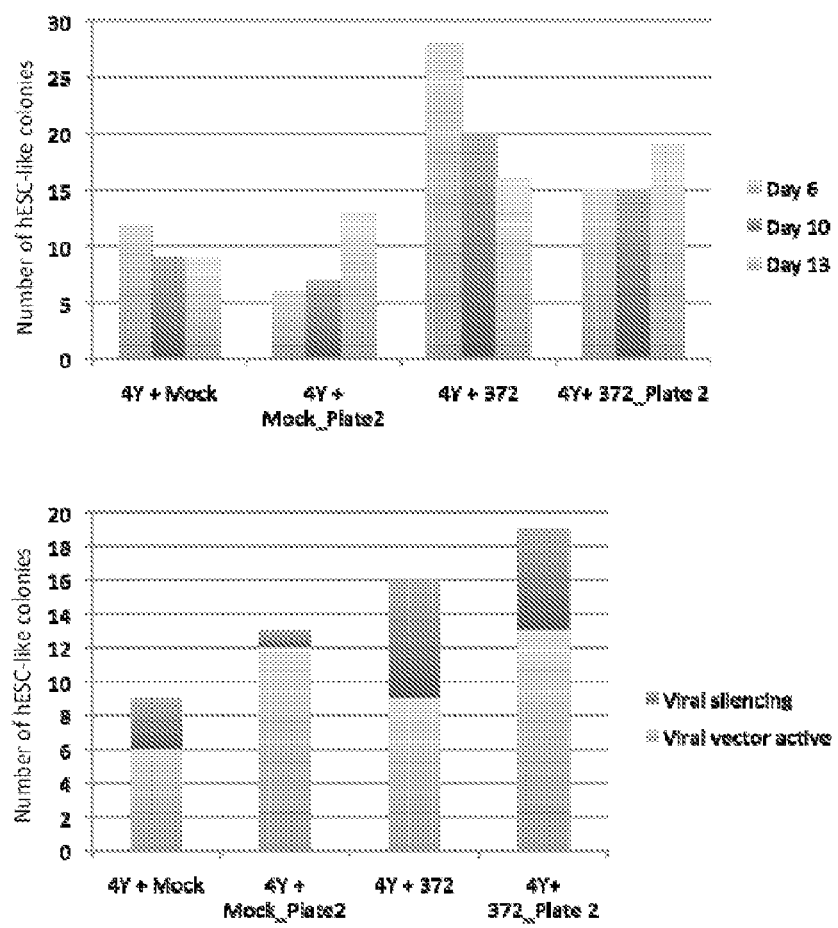
FIG. 18. miR-372 enhances 4 factor reprogramming of human foreskin fibroblasts Human foreskin fibroblasts were infected with retroviruses expressing Oct4, Sox2, Klf4, c-Myc and a fluorescent protein, Venus. MicroRNA 372 was transfected on days 3 and 10 post infection. Introduction of microRNA 372 resulted in an increase in the number of human ES cell-like colonies. Silencing of exogenous factors, which is an indication of complete reprogramming was assessed by the silencing of Venus.
Figure 19:
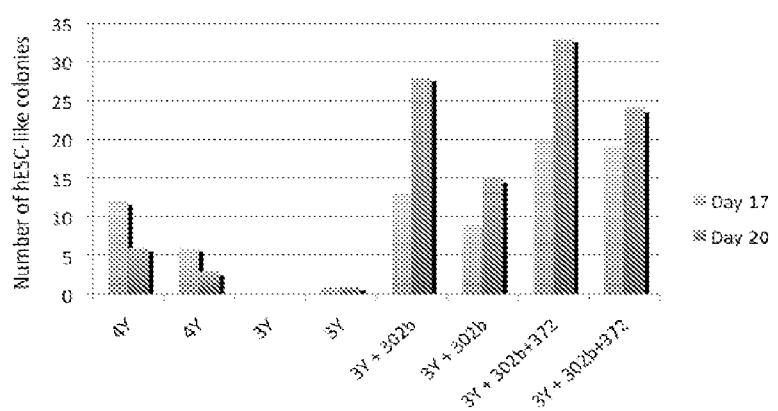
FIG. 19. miR-372 and 302b enhance 3 factor reprogramming of human foreskin fibroblasts. Human foreskin fibroblasts were infected with retroviruses expressing Oct4, Sox2, Klf4 and a fluorescent protein, Venus. MicroRNA 372, 302b or 372 and 302b were transfected on days 3 and 10 post infection. The number of human ES cell-like colonies were counted on days 17 and 20 post infection. Silencing of exogenous factors, which is an indication of complete reprogramming was assessed by the silencing of Venus.
Figure 19:
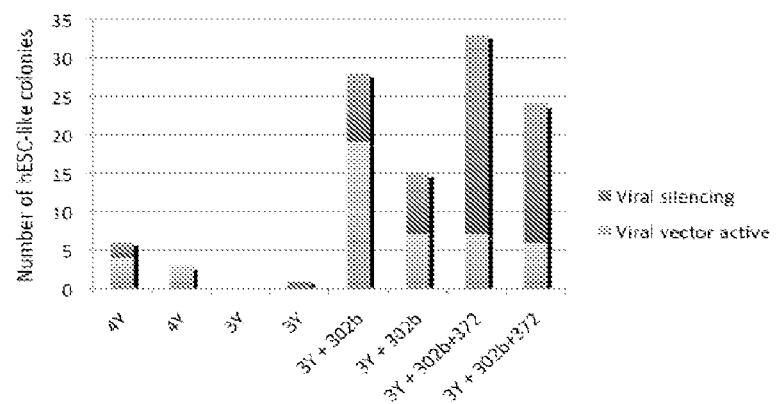

Having identified a pro-differentiation function of the let-7 family of miRNAs, we hypothesized that inhibition of this miRNA family would enhance reprogramming of somatic cells to iPS cells. Indeed, Lin28, among other activities (Heo, I. et al. *Cell* 138:696-708 (2009); Xu, B. et al., *RNA* 15:357-361 (2009); Jones, M. R. et al. *Nat. Cell Biol* 11:1157-1163 (2009); Polesskaya, A. et al. *Genes Dev* 21:1125-1138 (2007)), inhibits let-7 biogenesis (Rybak, A. et al. *Nat Cell Biol* 10:987-93 (2008); Viswanathan, S. R. et al., *Science* 320:97-100 (2008); Heo, I. et al. *Mol Cell* 32:276-84 (2008); Newman, M. A. et al., *RNA* 14:1539-49 (2008)) and promotes de-differentiation of human somatic cells to iPS cells (Yu, J. et al. *Science* 318:1917-1920 (2007)). Reprogramming to iPS cells is typically achieved by the introduction of virally expressed Pou5fl/Oct4, Sox2, and Klf4 with or without Myc into somatic cells such as mouse embryonic fibroblasts (MEFs). While Myc dramatically increases the efficiency of reprogramming, it is not essential (Nakagawa, M. et al. *Nat. Biotechnol* 26:101-106 (2008); Wernig, M. et al., *Cell Stem Cell* 2:10-12 (2008)). To test the impact of let-7 family on reprogramming, we used a let-7 antisense inhibitor. This inhibitor was able to suppress multiple let-7 family members simultaneously (FIG. 17).

MEFs express high levels of mature let-7 (Marson, A. et al. *Cell* 134:521-33 (2008)) and, therefore, these cells should be responsive to any pro-reprogramming effects of let-7 downregulation. We used Oct4::GFP transgenic MEFs in order to quantify changes in reprogramming efficiencies as Oct4::GFP is activated late in the reprogramming process (Stadtfeld, M. et al., *Cell Stem Cell* 2:230-240 (2008); Brambrink, T. et al. *Cell Stem Cell* 2:151-159 (2008)). MEFs were transduced with retroviral vectors expressing Pou5fl/Oct4, Sox2, Klf4, with or without cMyc on day 0 as well as transfected with let-7 or a control inhibitor on days 0 and 6. When 3 transcription factors were used (minus cMyc), let-7 inhibition increased the number of GFP positive colonies on day 10 by 4.3 fold compared to mock whereas a control inhibitor had no significant effect (FIG. 14a, left panel). In the presence of all 4 transcription factors, let-7 inhibition resulted in a 1.75 fold increase (FIG. 14a, right panel). Immunofluorescence confirmed expression of Nanog in reprogrammed cells (data not shown). Furthermore, the resulting iPS cells expressed endogenous pluripotency markers at levels similar to wild-type ESCs and did not express the exogenously introduced factors (data not shown), as expected for fully reprogrammed cells (Hochedlinger, K. et al., *Development* 136 (4):509-523 (2009)). The impact of the let-7 inhibitor is not due to enhanced proliferation of the MEFs as there was actually a subtle decrease in proliferation following transfection of either the let-7 or control inhibitor (data not shown). These findings show that inhibition of let-7 family of miRNAs enhances the reprogramming of somatic cells. The finding that the enhancement was greater in absence of Myc is consistent with Myc activity being one, but not the only important downstream target of let-7 in stabilizing the somatic cell fate.

Methods Summary

Dgcr8-/- and Wild-Type V6.5

ESCs were cultured as previously described (Wang, Y. et al., *Nat Genet* 39:380-5 (2007)). miRNA mimics and inhibitors were obtained from ThermoFisher. mRNA profiling was performed on Affymetrix Mouse Gene 1.0 ST arrays. Bioinformatic analysis was performed using significance analysis of microarrays (SAM), R packages, and custom Python scripts. Reprogramming with Oct4-GFP MEFs was performed as previously described (Judson, R. et. al., Nat Biotech (2009)). See, also Melton et. al., Nature 463:621-626 (2010) which are incorporated herein by reference in their entirety with respect to the methods and results disclosed therein.

Tissue Culture, Transfection and Alkaline Phosphatase Staining.

ESC lines and culture conditions were previously described[3]. ESCs were weaned off MEFs and maintained in MEF conditioned media. For ESC differentiation assays, 40,000 Dgcr8$^{-/-}$ or 12,000 wild-type ESCs were plated in gelatinized 12-well plates (or half the number of cells were plated on 24-well plates) on day 0 in LIF media. On day 1, miRIDIAN miRNA mimics (Dharmacon, ThermoFisher) were transfected at a concentration of 50 nM using Dharmafect1 (Dharmacon, ThermoFishcr) following the manufacturer's protocol. Media was changed daily. On the third day after transfection, cells were either lysed in Trizol (Invitrogen) for qRT-PCR analysis or fixed in 4% paraformaldehyde (PFA) for alkaline phosphatase staining. Alkaline phosphatase staining was performed per the manufacturer's instructions (Vector Labs). iPS cell lines were maintained in ESC media plus 15% knockout serum on irradiated MEF feeders. Colony reformation assays were performed as previously described3. In brief, cells were exposed to miRNA mimics for 3 days then trypsinized and counted. A defined number of cells were replated on MEFs to form colonies for 5-7 days. The efficiency of colony reformation was determined by dividing the number of alkaline-phosphatase-positive colonies by the number of cells plated. Some neural progenitor can be generated by in vitro differentiation of ESCs as described previously (Okabe, S., Forsberg-Nilsson, K., Spiro, A. C., Segal, M. & McKay, R. D. Development of neuronal precursor cells and functional postmitotic neurons from embryonic stem cells in vitro. Mech. Dev. 59, 89-102 (1996)).

ESC Derivation.

Timed matings were set up for c-myc f/f mice (Trumpp et al., Nature 414:768-773 (2001). ESCs were derived from embryos isolated at embryonic day (E)3.5. These embryos were cultured on an irradiated MEF feeder layer in ESC media supplemented with 50 mM PD98059 (Buehr, M. & Smith, A. Genesis of embryonic stem cells. Phil. Trans. R. Soc. Lond. B 358, 1397-1402 (2003)) and disassociated onto fresh feeders. ESCs were PCR genotyped as previously described (Trumpp et al., Nature 414:768-773 (2001). Aflox/flox line was grown out, infected with Ad5 Cre-IRES-GFP virus, sorted by FACS, and plated back onto MEF feeders. c-myc2/2 colonies were grown out and verified by PCR genotyping and western blotting.

mRNAarrays.

qRT-PCR showed that mRNAlevels of a known let-7 target, Lin28, was maximally reduced 12 h after transfection before a large decline in Oct4 and Nanog (data not shown). Therefore, we chose 12 h for all microarray analysis to minimize secondary effects of let-7c-induced differentiation. On day 0, 150,000 cells were plated in a 3.5-cm dish. miRIDIAN miRNA mimics (Dharmacon, ThermoFisher) were transfected at a concentration of 50 nM in media in the absence of LIF. At 12 h after transfection cells were lysed in Trizol (Invitrogen) and RNA was prepared according to the manufacturer's protocol. Affymetrix Mouse Gene 1.0 ST arrays were probed by the Gladstone Genomics Core. Three biological samples were assayed for each treatment. Data were analyzed by Affymetrix Expression Console software. The robust multichip analysis (RMA) algorithm was used to normalize the array signal across chips. SAM was used to determine FDRcutoffs for significantly altered genes.

qRT-PCR Analysis.

RNA for all qRT-PCR analyses was prepared using Trizol (Invitrogen) and quantified on a Nanodrop Spectrophotometer (ThermoFisher). Five-hundred nanograms of RNA was DNase-treated using DNaseI amplification grade (Invitrogen). For qRT-PCR of mRNAs, DNase-treated samples were reverse-transcribed using the Superscript III first-strand synthesis system for RT-PCR (Invitrogen). qPCR reactions on resulting cDNAs were performed on either an ABI Prism 7100 or an ABI 7900HT (Applied Biosystems). For miRNAs, qRT-PCR was performed either by using TaqMan miRNA assays (Applied Biosystems) or by polyadenylating the miRNAs and then using a modified oligodT reverse transcription primer as described previously (Shi, R. & Chiang, V. L. Facile means for quantifying microRNA expression by realtime PCR. Biotechniques 39, 519-525 (2005)).

Lin28 and GFP Expression in 293T Cells.

Lin28 was cloned into an expression vector under the EF1α promoter and upstream of IRES Pac (puromycin resistance). A similarly constructed GFP expression construct was previously generated. 293T cells were transfected with 5 μg of each construct and selected with 0.6 μg/ml puromycin for 12 days.

Luciferase Reporter Assays.

Constructs were produced as follows. The N-myc and Sal14 3'UTRs were amplified from ESC cDNA and cloned into the NotI and XhoI sites in psiCheck-2 vector (Promega). Mutant UTRs were generated by a two-step PCR strategy with overlapping mutated PCR primers. Products of two PCRs with mutations were used in a second PCR reaction to generate full-length mutated inserts that were cut and ligated into a cut empty vector. For transfections, 8,000 Dgcr8$^{-/-}$ ESCs were plated in ESC media in a 96-well plate pretreated with 0.2% gelatin. The next day, miRIDIAN miRNA mimics (Dharmacon, ThermoFisher) were transfected with Dharmafect1 (Dharmacon, ThermoFisher) following the manufacturer's protocol at a concentration of 100 nM. Simultaneously, luciferase constructs were transfected into ESCs at a concentration of 200 ng per well using FUGENE 6 (Roche) transfection reagent following the manufacturers protocol. The next day, 14-18 h later, cells were lysed and luciferase assays were performed using a Dual-Luciferase ReporterAssay System (Promega) on a single automatic injection Mithras (Berthold technologies) luminometer following the manufacturer's protocol. Transfection of each construct was performed in triplicate in each assay. Ratios of Renilla luciferase readings to firefly luciferase readings were averaged for each experiment. Replicates performed on separate days were mean centered with the common readings from the individual days.

Seed Match Analysis.

Promoter (1,000 base pairs from the transcriptional start), 5'UTR, ORF and 3'UTRs for Ensembl Transcripts (mm9) and known genes (mm8) were downloaded separately from the UCSC Genome Browser Table Browser. Seed match analysis was performed on these transcripts using a custom Python script. 7-nucleotide seeds were defined as either 7mer-1A or 7mer-m8 (Lewis, B. P., Burge, C. B. & Bartel, D. P. Conserved seed pairing, often flanked by adenosines, indicates that thousands of human genes are microRNA targets. Cell 120, 15-20 (2005)). Seed match results were mapped to Affymetrix IDs. A Python script was then implemented to eliminate redundant transcripts as transcripts often mapped 0.1:1 with Affymetrix IDs. The transcript with the most 7-nucleotide seed matches was chosen to produce a 1:1 transcript to Affymetrix ID mapping. This mapping was done separately for the promoters, 5'UTRs, ORFs and 3'UTRs. In rare cases, duplicate Affymetrix IDs exist for the same gene. These were retained in our analyses. Microsoft Access (Microsoft) was used to generate list overlaps for analyses. P-values were calculated in FIGS. 11b, d with the number of seed matches per kb of transcript using Wilcoxon's rank sum test in R. P-values were calculated using a binary 0 for no seed matches or 1 for a seed match using the hypergeometric distribution function in R.

ChIP Target Overlap Analysis.

ChIP targets were downloaded as described in Melton et al, Nature 463:621-626 (2010). Scripts were written to convert provided transcript IDs to a non-redundant list of Affymetrix IDs. Microsoft Access (Microsoft) and custom Python scripts were used to perform comparisons between gene lists and ChIP gene target lists. ChIP data described previously was downloaded as an association score between any particular gene and the transcription factor of interest (Chen, X. et al. Cell 133:1106-17 (2008)). These scores were used directly for enrichment. For the Oct4-, Sox2-Nanogbound group per Chen et al., any score above 0 was counted as bound. For all data, enrichment for ChIP gene target sets in miRNA-regulated gene sets was performed relative to all genes analysed to produce the miRNA-regulated gene sets (that is, all genes with Affymetrix IDs mapping to coding transcripts). The enrichments for any given ChIP target set were median normalized with all the miRNA-regulated genes sets in FIG. 12B. We performed this normalization because both the ChIP targets of the transcription factors and the miRNAregulated gene sets in our analysis are enriched for more highly expressed genes. We get a similar pattern of results without this normalization, although all comparisons appear more highly enriched owing to the expression levels (data not shown). Un-normalized enrichment is defined as: (genes in overlap of miRNA-altered group and ChIP group/all genes in miRNA-altered group)/(all genes in ChIP group/all genes used in analysis to generate miRNA altered groups).

Figure 3:
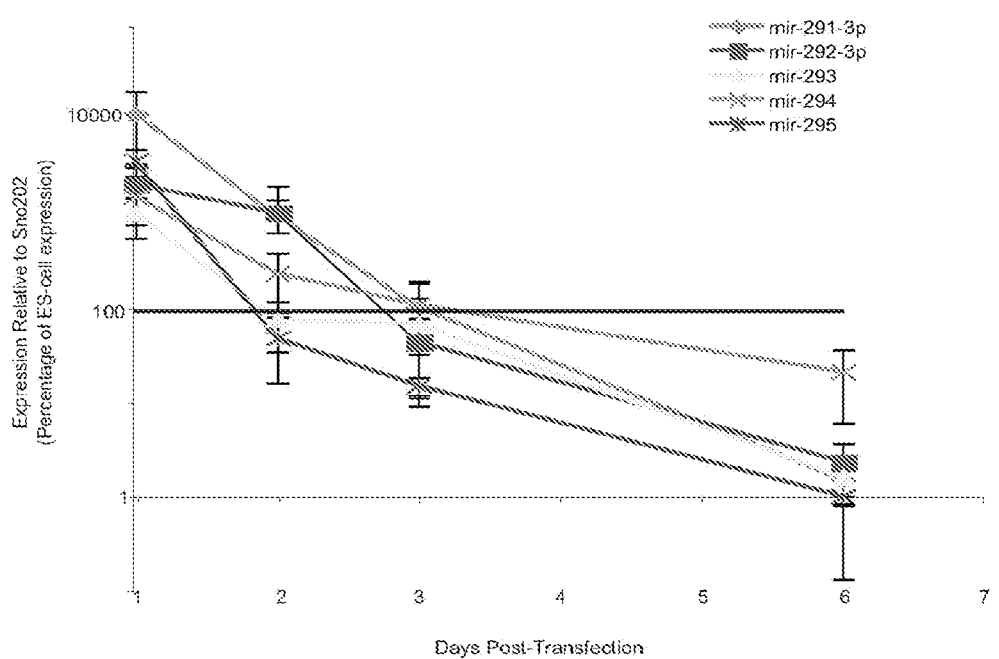
FIG. 3. Characterization and application of miR-290 cluster mimics. (a) miR-290 cluster expression levels in mimic-transfected MEFs. MiRNA mimic (16 nM) was transfected into MEFs, and RNA was collected on days 1, 2, 3, and 6. Relative miRNA levels were compared via RT-qPCR to control (v6.5) ES cells (black horizontal bar). Mimic levels were found to be well above ES expression levels one day after transfection, but close to physiological levels between days 2 and 3. (b) Reprogramming assay timeline. In reprogramming assays, MEFs were transfected on days 0 and 6 in order to retain ES-like levels of the mimics.

Our enrichment analysis could yield several possible outcomes depending on whether the miRNA targeted the transcription factor directly versus targeted transcripts downstream of the transcription factor. The following outcomes are presented in FIG. 12A. (1) If an miRNA directly targets a specific transcriptional activator, this activator will be downregulated, and thus its ChIP target genes will likewise tend to be downregulated. This will result in an enrichment of ChIP target genes within the miRNA's downregulated gene set independent of there being a seed match in these targets. Similarly, the ChIP target genes should be depleted in the miRNA's upregulated gene set (FIG. 12A, a). (2) If an miRNA directly targets a transcriptional repressor, there would be the inverse outcome; that is, the ChIP target genes should be enriched in the miRNA's upregulated gene set and depleted in the miRNA's downregulated gene set regardless of seed match (FIG. 3A, b). If an miRNA targets an activating transcription factor's downstream targets, but not the transcription factor itself, ChIP target genes would be enriched in the downregulated gene set with a seed match but not without a seed match. Furthermore, there should not be enrichment in the upregulated transcripts (FIG. 12A, c).

Gene Ontology.

Stem-cell-associated genes (genes upregulated in ESCs relative to brain and bone marrow) were generated from data described previously (Lewis et al., Cell 120:15-20 (2005) and were downloaded as a list from MySigDB. Enrichment of these stem cell associated genes in miRNA altered gene sets was performed, and P-values were calculated by Fischer's exact test.

Immunohistochemistry.

Cells were fixed with 4% PFA and washed twice in PBS with 0.1% Triton X-100 (PBT). PBT with 2% bovine serum albumin (BSA) and 1% goat-serum was used to block for 1 h before the addition of primary antibody against Oct4 (Santa Cruz, rabbit polyclonal, product sc-9081) or Nanog (Calbiochem, rabbit polyclonal, product sc-1000), which was incubated overnight at 4° C. or at room temperature for approximately 2 h. Cells were washed with PBT, blocked with PBT plus 2% BSA and 10% goat-serumn for 1 h before addition of secondary antibodies (Alexa Fluor 488 goat anti-rabbit IgG, Invitrogen).

Western Blots.

On day 0, approximately 200,000 Dgcr8$^{-/-}$ or 50,000 wild-type ESCs were plated in a 6-well plate. The next day miRIDIAN miRNA mimics (Dharmacon, ThermoFisher) were transfected at a concentration of 50 nM. Lysates were collected 2 days after transfection in EBC buffer (50 mM Tris-HCl, pH 8.0, 120 mM NaCl, 0.5% Nonidet P-40, 1 mM EDTA) containing 1× protcase inhibitor cocktail (Roche). Lysates were incubated at 4° C. for 45 min rocking then spun at 4° C. and approximately 20,000 g in a table-top centrifuge. Protein was quantified using a Bio-Rad protein assay (Bio-Rad). Thirty micrograms of protein was resolved on an 8% SDS-PAGE gel. Proteins were transferred to Immobilon-FL (Millipore) and processed for immunodetection. Blots were scanned on a Licor Odyssey Scanner (Licor). The actin antibody was used at a 1:1,000 dilution (Sigma, mouse monoclonal clone AC-40, A4700), the c-Myc antibody at 1:500 (Epitomics, N-term rabbit monoclonal, 1472-1), the N-Myc antibody at 1:500 (Calbiochem, mouse monoclonal, OP13), the Nanog antibody at 1:1,000 (Abcam, rabbit polyclonal, ab21603), the Sa114 antibody at 1:500 (Abcam, rabbit polyclonal, ab29112), and the Lin28 antibody at 1:1,000 (Abcam, rabbit polyclonal, ab46020). Secondary infrared-dye antibodies from Licor were used at 1:10,000. Data were exported from the Licor Odyssey as jpg and quantified using ImageJ software (NIH).

MEF Isolation.

E13.5 embryos from Oct4-GFP/Rosa-26-β-galactosidase transgenic crosses were isolated by Caesarean section and washed in HBSS. Heads and visceral tissues were removed. Remaining tissue was washed in fresh HBSS, briefly rinsed with 70% ethanol, then submerged in 0.05 mM trypsin/1 mM EDTA HBSS solution and incubated at 37° C. for 10 min. Tissue was pipetted repeatedly to aid in tissue dissociation, then added to MEF media containing 10% FBS and plated (passage 0).

Retrovirus Infection.

The retroviral packaging vector pCL-ECO was transfected into 293T cells simultaneously with pMXs vectors containing Oct4, Sox2, Klf4 or c-myc cDNA(Addgene) using Fugene 6 (Roche) (Takahashi, K. & Yamanaka, S. Induction of pluripotent stem cells from mouse embryonic and adult fibroblast cultures by defined factors. Cell 126, 663-676 (2006)). At 24 h, the media was changed, and at 48 h, the media was collected, filtered (0.45 μM), and frozen in aliquots at −80° C. Retrovirus was never thawed more than once. To induce reprogramming, passage 3 Oct4-GFP, Rosa26-Glb1/neo MEFs49 (Blelloch, R., Venere, M., Yen, J. & Ramalho-Santos, M. Generation of induced pluripotent stem cells in the absence of drug selection. Cell Stem Cell 1, 245-247 (2007)) were plated on gelatin-coated 12-well plates at 12,000 cells per well. Retrovirus-containing media was added 24 h later (day 0). Cells were transfected with 16 nM microRNA inhibitors (Dharmacon, ThermoFisher, I-310106-04 for let-7 inhibitor, IN-001000-01-05 for control inhibitor). Cells in reprogramming assays were transfected on days 0 and 6 after retroviral infection. Media was changed daily. Media was replaced with ESC media+15% FBS+LIF on day 2, and ESC media+15% knockout serum replacement (Invitrogen)+LIF on day 6. GFP colonies were counted on day 10. Individual iPS cell colonies were picked and expanded for analysis between days 10 and 15.

Example 3

Additional Identified Useful ESCC miRNA Mimics. Identified During a Screen of Three Factors (Oct4, Sox2, KLF4+ microRNA Mimic).

GFP+ Colonies, Normalized to Mock

| microRNA mimic | exp. 1 | exp. 2 | average |
|---|---|---|---|
| mmu-miR-302b | 11.8 | 65.3 | 38.6 |
| mmu-miR-302 | 14 | 26.7 | 20.4 |
| mmu-miR-302d | 8.7 | 12.7 | 10.7 |
| mmu-miR-294 | 3.2 | 16 | 9.6 |
| mmu-miR-302c | 2.2 | 14 | 8.1 |
| mmu-miR-295 | 0 | 12.8 | 6.4 |
| mmu-miR-93 | 1.6 | 10.8 | 6.2 |
| mmu-miR-291-3p | 6.4 | 0 | 3.2 |
| mmu-miR-19a | 0 | 5.2 | 2.6 |
| mmu-miR-106a | 0 | 4.5 | 2.3 |
| mmu-miR-223 | 2.9 | 0.7 | 1.8 |
| mmu-miR-291b-3p | 2.1 | 0 | 1.1 |
| mmu-miR-20b | 1.1 | 0 | 0.6 |
| mmu-miR-33 | 0 | 0 | 0 |

Example 4

Enhancers of reprogramming, defined by having GFP+ colony number greater than all the mocks in at least one screen and having at least a 2x fold average increase (52 mimics total). Identified during a screen of three factors (Oct4, Sox2, KLF4+ microRNA mimic).

Generally, the reprogramming factors (in this case Oct4, Sox2, and Klf4 via retrovirus) are added to the somatic cells (in this case Oct4-GFP MEFs) and after waiting 2 weeks, while changing media, two parameters are evaluated. Cells are also transfected with individual miRNA mimics as already described in the patent. First, GFP+ colonies are counted. It has previously been shown that reactivation of the silenced Oct4-GFP transgene in the MEFs is a very late marker of reprogramming, indicative of a full pluripotent state. The cells are also stained and counted for alkaline phosphatase (AP) positive colonies. It has previously been shown that AP activation is a very early step in the reprogramming process, but is not as useful for indicating full reprogramming—ie, it marks that the process has begun but not necessarily finished.

For the screen, which is depicted in Examples 4 and 5, wells treated with no miRNA—that is just Oct4, Sox2 and Klf4 retrovirus and transfection reagent typically yield ~0 to 4 GFP+ colonies. Usually, 16 of these no miRNA mock wells are run per plate which means, per experiment, each miRNA-including well is being compared to the average of 16 no miRNA mock wells. The "fold change" then, is the number of GFP+(or AP+) colonies from the microRNA-containing well divided by the average of the number of GFP+(or AP+) colonies of the 16 mock wells. Although many mock wells gave 0 colonies, the average of the 16 mock wells was always greater than zero and less than two. Thus, if one of the miRNA-containing wells had no GFP+ colonies, the normalized value is going to be 0. Take, for example, mir-291-3p which, over many experiments we have previously established as an enhancer of reprogramming, but in one of the wells of the screen, gave a 0—likely, more of an indicator that that particular well did not work great. Thus the strongest candidates are those that yielded >2-3× average increases in efficiency and indeed, most of the ESCCs fall into this category. As for the rest, they still have promising potential to be enhancers.

| microRNA mimic | exp. 1 | exp. 2 | ave. | Sequence (SEQ ID NO:) |
|---|---|---|---|---|
| mmu-miR-302b | 11.8 | 65.3 | 38.6 | UAAGUGCUUCCAUGUUUUAGUAG (23) |
| mmu-miR-302 | 14 | 26.7 | 20.3 | UAAGUGCUUCCAUGUUUUGGUGA (24) |
| mmu-miR-495 | 27.2 | 0 | 13.6 | AAACAAACAUGGUGCACUUCUU (25) |
| mmu-miR-26a | 1.1 | 23.3 | 12.2 | UUCAAGUAAUCCAGGAUAGGCU (26) |
| mmu-miR-19a* | 6 | 16 | 11 | UAGUUUUGCAUAGUUGCACUAC (27) |
| mmu-miR-302d | 8.7 | 12.7 | 10.7 | UAAGUGCUUCCAUGUUUGAGUGU (28) |
| mmu-miR-10b | 1.1 | 18.7 | 9.9 | UACCCUGUAGAACCGAAUUUGUG (29) |
| mmu-miR-294 | 3.2 | 16 | 9.6 | AAAGUGCUUCCCUUUUGUGUGU (30) |
| mmu-miR-302c | 2.2 | 14 | 8.1 | AAGUGCUUCCAUGUUUCAGUGG (31) |
| mmu-miR-183* | 0 | 16 | 8 | GUGAAUUACCGAAGGGCCAUAA (32) |
| mmu-miR-200a | 0 | 16 | 8 | UAACACUGUCUGGUAACGAUGU (33) |
| mmu-miR-34c* | 4.8 | 9.8 | 7.3 | AAUCACUAACCACACAGCCAGG (34) |
| mmu-miR-293 | 1.6 | 12.8 | 7.2 | AGUGCCGCAGAGUUUGUAGUGU (35) |
| mmu-miR-181b | 0 | 14 | 7 | AACAUUCAUUGCUGUCGGUGGGU (36) |
| mmu-miR-151 | 0 | 13.3 | 6.7 | CUAGACUGAGGCUCCUUGAGG (37) |

-continued

| microRNA mimic | exp. 1 | exp. 2 | ave. | Sequence (SEQ ID NO:) |
|---|---|---|---|---|
| mmu-miR-680 | 0 | 12.8 | 6.4 | GGGCAUCUGCUGACAUGGGGG (38) |
| mmu-miR-295 | 0 | 12.8 | 6.4 | AAAGUGCUACUACUUUUGAGUCU (39) |
| mmu-miR-880 | 2 | 10.7 | 6.3 | UACUCCAUCCUCUCUGAGUAGA (40) |
| mmu-miR-93 | 1.6 | 10.8 | 6.2 | CAAAGUGCUGUUCGUGCAGGUAG (41) |
| mmu-miR-455-5p | 6 | 5.3 | 5.7 | UAUGUGCCUUUGGACUACAUCG (42) |
| mmu-miR-144 | 8.7 | 2.6 | 5.7 | UACAGUAUAGAUGAUGUACU (43) |
| mmu-miR-467d | 5.3 | 5.6 | 5.5 | UAAGUGCGCGCAUGUAUAUGCG (44) |
| mmu-miR-484 | 0 | 10.7 | 5.3 | UCAGGCUCAGUCCCCUCCCGAU (45) |
| mmu-miR-205 | 0 | 10.7 | 5.3 | UCCUUCAUUCCACCGGAGUCUG (46) |
| mmu-miR-582-5p | 10.2 | 0.4 | 5.3 | UACAGUUGUUCAACCAGUUACU (47) |
| mmu-miR-290-3p | 2 | 8 | 5 | AAAGUGCCGCCUAGUUUUAAGCCC (48) |
| mmu-miR-138* | 2 | 8 | 5 | CGGCUACUUCACAACACCAGGG (49) |
| mmu-miR-181d | 8 | 1.9 | 4.9 | AACAUUCAUUGUUGUCGGUGGGU (50) |
| mmu-miR-324-3p | 7.3 | 2.2 | 4.8 | CCACUGCCCCAGGUGCUGCU (51) |
| mmu-miR-877* | 0 | 8 | 4 | UGUCCUCUUCUCCCUCCUCCCA (52) |
| mmu-miR-23a | 8 | 0 | 4 | AUCACAUUGCCAGGGAUUUCC (53) |
| mmu-miR-379 | 0 | 8 | 4 | UGGUAGACUAUGGAACGUAGG (54) |
| mmu-miR-673 | 8 | 0 | 4 | CUCACAGCUCUGGUCCUUGGAG (55) |
| mmu-miR-876-5p | 4.8 | 2.6 | 3.7 | UGGAUUUCUCUGUGAAUCACUA (56) |
| mmu-miR-291-3p | 6.4 | 0 | 3.2 | AAAGUGCUUCCACUUUGUGUGC (57) |
| mmu-miR-30d | 3.2 | 3.1 | 3.1 | UGUAAACAUCCCCGACUGGAAG (58) |
| mmu-miR-421 | 5.8 | 0.4 | 3.1 | AUCAACAGACAUUAAUUGGGCGC (59) |
| mmu-miR-879* | 2.7 | 3.5 | 3.1 | GCUUAUGGCUUCAAGCUUUCGG (60) |
| mmu-miR-542-3p | 6 | 0 | 3 | UGUGACAGAUUGAUAACUGAAA (61) |
| mmu-miR-124* | 1.6 | 4.1 | 2.9 | CGUGUUCACAGCGGACCUUGAU (62) |
| mmu-miR-363 | 1.5 | 4.1 | 2.8 | AAUUGCACGGUAUCCAUCUGUA (63) |
| mmu-miR-871 | 2.7 | 2.5 | 2.6 | UAUUCAGAUUAGUGCCAGUCAUG (64) |
| mmu-miR-19a | 0 | 5.2 | 2.6 | UGUGCAAAUCUAUGCAAAACUGA (65) |
| mmu-miR-16* | 2.7 | 2.2 | 2.4 | CCAGUAUUGACUGUGCUGCUGA (66) |
| mmu-miR-873 | 1.5 | 3.3 | 2.4 | GCAGGAACUUGUGAGUCUCCU (67) |
| mmu-miR-199b | 0 | 4.6 | 2.3 | CCCAGUGUUUAGACUACCUGUUC (68) |
| mmu-miR-106a | 0 | 4.5 | 2.2 | CAAAGUGCUAACAGUGCAGGUAG (69) |
| mmu-miR-181b | 4.3 | 0 | 2.2 | AACAUUCAUUGCUGUCGGUGGGU (70) |
| mmu-miR-200a* | 4.3 | 0 | 2.1 | CAUCUUACCGGACAGUGCUGGA (71) |
| mmu-miR-431* | 4.3 | 0 | 2.1 | CAGGUCGUCUUGCAGGGCUUCU (72) |
| mmu-miR-689 | 1.6 | 2.6 | 2.1 | CGUCCCCGCUCGGCGGGUCC (73) |
| mmu-miR-721 | 1.6 | 2.6 | 2.1 | CAGUGCAAUUAAAAGGGGGAA (74) |

Number of GFP+ colonies divided by the average of the number of GFP+ colonies in the mock group

Example 5

Inhibitors of reprogramming, defined by having AP+ colony number less than all of the mocks in at least one screen and having at least a 40% average reduction (114 mimics total). Identified during a screen of three factors (Oct4, Sox2, KLF4+microRNA mimic).

AP+ Colonies, Normalized to mock:
Number of AP+ colonies divided by the average of the number of AP+ colonies in the mock group

| microRNA mimic | exp. 1 | exp. 2 | Ave. | sequence (SEQ ID NO:) |
|---|---|---|---|---|
| mmu-miR-744* | 0 | 0.14 | 0.07 | CUGUUGCCACUAACCUCAACCU (75) |
| mmu-miR-423-5p | 0 | 0.27 | 0.14 | UGAGGGGCAGAGAGCGAGACUUU (76) |
| mmu-miR-669c | 0 | 0.28 | 0.14 | AUAGUUGUGUGUGGAUGUGUGU (77) |
| mmu-let-7c | 0 | 0.28 | 0.14 | UGAGGUAGUAGGUUGUAUGGUU (78) |
| mmu-miR-466h | 0 | 0.28 | 0.14 | UGUGUGCAUGUGCUUGUGUGUA (79) |
| mmu-miR-654-3p | 0 | 0.35 | 0.18 | UAUGUCUGCUGACCAUCACCUU (80) |
| mmu-miR-470* | 0.22 | 0.15 | 0.19 | AACCAGUACCUUUCUGAGAAGA (81) |
| mmu-miR-24 | 0 | 0.41 | 0.2 | UGGCUCAGUUCAGCAGGAACAG (82) |
| mmu-miR-182 | 0.11 | 0.3 | 0.21 | UUUGGCAAUGGUAGAACUCACACCG (83) |
| mmu-miR-335 | 0 | 0.41 | 0.21 | UCAAGAGCAAUAACGAAAAAUGU (84) |
| mmu-miR-181c | 0 | 0.41 | 0.21 | AACAUUCAACCUGUCGGUGAGU (85) |
| mmu-miR-330 | 0 | 0.41 | 0.21 | GCAAAGCACAGGGCCUGCAGAGA (86) |
| mmu-miR-134 | 0 | 0.41 | 0.21 | UGUGACUGGUUGACCAGAGGGG (87) |
| mmu-miR-675-3p | 0.29 | 0.19 | 0.24 | CUGUAUGCCCUAACCGCUCAGU (88) |
| mmu-miR-218 | 0.29 | 0.19 | 0.24 | UUGUGCUUGAUCUAACCAUGU (89) |
| mmu-let-7f | 0 | 0.49 | 0.25 | UGAGGUAGUAGAUUGUAUAGUU (90) |
| mmu-miR-491 | 0.14 | 0.38 | 0.26 | AGUGGGGAACCCUUCCAUGAGG (91) |
| mmu-miR-466g | 0.26 | 0.27 | 0.26 | AUACAGACACAUGCACACACA (92) |
| mmu-miR-465c-3p | 0.26 | 0.27 | 0.26 | GAUCAGGGCCUUUCUAAGUAGA (93) |
| mmu-miR-202 | 0 | 0.54 | 0.27 | AGAGGUAUAGCGCAUGGGAAGA (94) |
| mmu-miR-681 | 0 | 0.54 | 0.27 | CAGCCUCGCUGGCAGGCAGCU (95) |
| mmu-miR-877 | 0 | 0.54 | 0.27 | GUAGAGGAGAUGGCGCAGGG (96) |
| mmu-miR-875-5p | 0 | 0.54 | 0.27 | UAUACCUCAGUUUUAUCAGGUG (97) |
| mmu-miR-712 | 0 | 0.56 | 0.28 | CUCCUUCACCCGGGCGGUACC (98) |
| mmu-miR-297 | 0.22 | 0.35 | 0.29 | AUGUAUGUGUGCAUGUGCAUGU (99) |
| mmu-let-7d | 0.44 | 0.15 | 0.29 | AGAGGUAGUAGGUUGCAUAGUU (100) |
| mmu-miR-142-3p | 0.11 | 0.49 | 0.3 | UGUAGUGUUUCCUACUUUAUGGA (101) |
| mmu-miR-328 | 0.48 | 0.14 | 0.31 | CUGGCCCUCUCUGCCCUUCCGU (102) |
| mmu-miR-485-5p | 0.48 | 0.14 | 0.31 | AGAGGCUGGCCGUGAUGAAUUC (103) |
| mmu-miR-122a | 0.22 | 0.42 | 0.32 | UGGAGUGUGACAAUGGUGUUUG (104) |
| mmu-miR-877* | 0.26 | 0.41 | 0.33 | UGUCCUCUUCUCCCUCCUCCCA (105) |
| mmu-miR-135a | 0.14 | 0.56 | 0.35 | UAUGGCUUUUUAUUCCUAUGUGA (106) |
| mmu-miR-674-3p | 0.14 | 0.56 | 0.35 | CACAGCUCCCAUCUCAGAACAA (107) |
| mmu-miR-497 | 0.14 | 0.56 | 0.35 | CAGCAGCACACUGUGGUUUGUA (108) |
| mmu-miR-7b | 0.33 | 0.42 | 0.38 | UGGAAGACUUGUGAUUUUGUUGU (109) |

-continued

| microRNA mimic | exp. 1 | exp. 2 | Ave. | sequence (SEQ ID NO:) |
|---|---|---|---|---|
| mmu-miR-30b* | 0.26 | 0.49 | 0.38 | CUGGGAUGUGGAUGUUUACGUC (110) |
| mmu-miR-34b | 0.33 | 0.45 | 0.39 | AGGCAGUGUAAUUAGCUGAUUGU (111) |
| mmu-miR-466e-5p | 0 | 0.79 | 0.4 | GAUGUGUGUGUACAUGUACAUA (112) |
| mmu-miR-193b | 0.26 | 0.54 | 0.4 | AACUGGCCCACAAAGUCCCGCU (113) |
| mmu-miR-883a-5p | 0.26 | 0.54 | 0.4 | UGCUGAGAGAAGUAGCAGUUAC (114) |
| mmu-let-7i* | 0.17 | 0.64 | 0.41 | CUGCGCAAGCUACUGCCUUGCU (115) |
| mmu-miR-342 | 0.11 | 0.71 | 0.41 | UCUCACACAGAAAUCGCACCCGU (116) |
| mmu-miR-140* | 0.11 | 0.71 | 0.41 | UACCACAGGGUAGAACCACGG (117) |
| mmu-miR-24-2* | 0.26 | 0.56 | 0.41 | GUGCCUACUGAGCUGAAACAGU (118) |
| mmu-miR-195 | 0.12 | 0.71 | 0.42 | UAGCAGCACAGAAAUAUUGGC (119) |
| mmu-miR-297a | 0.12 | 0.71 | 0.42 | AUGUAUGUGUGCAUGUGCAUGU (120) |
| mmu-miR-344 | 0.12 | 0.71 | 0.42 | UGAUCUAGCCAAAGCCUGACUGU (121) |
| mmu-miR-18 | 0.77 | 0.07 | 0.42 | UAAGGUGCAUCUAGUGCAGAUAG (122) |
| mmu-miR-93* | 0.35 | 0.5 | 0.42 | ACUGCUGAGCUAGCACUUCCCG (123) |
| mmu-miR-297 | 0.66 | 0.21 | 0.43 | AUGUAUGUGUGCAUGUGCAUGU (124) |
| mmu-miR-16 | 0.24 | 0.63 | 0.44 | UAGCAGCACGUAAAUAUUGGCG (125) |
| mmu-miR-380-5p | 0.52 | 0.36 | 0.44 | AUGGUUGACCAUAGAACAUGCG (126) |
| mmu-miR-672 | 0.17 | 0.71 | 0.44 | UGAGGUUGGUGUACUGUGUGUGA (127) |
| mmu-miR-431 | 0.33 | 0.57 | 0.45 | UGUCUUGCAGGCCGUCAUGCA (128) |
| mmu-miR-715 | 0.14 | 0.75 | 0.45 | CUCCGUGCACACCCCCGCGUG (129) |
| mmu-miR-669a | 0.14 | 0.75 | 0.45 | AGUUGUGUGUGCAUGUUCAUGU (130) |
| mmu-miR-103 | 0.48 | 0.41 | 0.45 | AGCAGCAUUGUACAGGGCUAUGA (131) |
| mmu-miR-124* | 0.12 | 0.79 | 0.46 | CGUGUUCACAGCGGACCUUGAU (132) |
| mmu-miR-15b | 0.12 | 0.79 | 0.46 | UAGCAGCACAUCAUGGUUUACA (133) |
| mmu-miR-450b* | 0.12 | 0.79 | 0.46 | AUUGGGAACAUUUUGCAUGCAU (134) |
| mmu-miR-882 | 0.35 | 0.57 | 0.46 | AGGAGAGAGUUAGCGCAUUAGU (135) |
| mmu-miR-686 | 0.52 | 0.41 | 0.46 | AUUGCUUCCCAGACGGUGAAGA (136) |
| mmu-miR-222 | 0.22 | 0.71 | 0.46 | AGCUACAUCUGGCUACUGGGU (137) |
| mmu-miR-684 | 0 | 0.94 | 0.47 | AGUUUUCCCUUCAAGUCAA (138) |
| mmu-miR-450b | 0.24 | 0.71 | 0.47 | UUUUGCAGUAUGUUCCUGAAUA (139) |
| mmu-miR-582-3p | 0.17 | 0.78 | 0.48 | CCUGUUGAACAACUGAACCCAA (140) |
| mmu-miR-135b | 0.17 | 0.78 | 0.48 | UAUGGCUUUUCAUUCCUAUGUGA (141) |
| mmu-miR-493 | 0.26 | 0.7 | 0.48 | UGAAGGUCCUACUGUGUGCCAGG (142) |
| mmu-miR-546 | 0.97 | 0 | 0.48 | AUGGUGGCACGGAGUC (143) |
| mmu-miR-708 | 0.22 | 0.75 | 0.49 | AAGGAGCUUACAAUCUAGCUGGG (144) |
| mmu-miR-433-3p | 0.12 | 0.87 | 0.49 | AUCAUGAUGGGCUCCUCGGUGU (145) |
| mmu-miR-494 | 0.22 | 0.78 | 0.5 | UGAAACAUACACGGGAAACCUC (146) |
| mmu-miR-203 | 0.52 | 0.5 | 0.51 | GUGAAAUGUUUAGGACCACUAG (147) |

-continued

| microRNA mimic | exp. 1 | exp. 2 | Ave. | sequence (SEQ ID NO:) |
|---|---|---|---|---|
| mmu-miR-9 | 0.52 | 0.5 | 0.51 | UCUUUGGUUAUCUAGCUGUAUGA (148) |
| mmu-miR-574-5p | 0.39 | 0.63 | 0.51 | UGAGUGUGUGUGUGUGAGUGUGU (149) |
| mmu-miR-376c | 0.17 | 0.85 | 0.51 | AACAUAGAGGAAAUUUCACCU (150) |
| mmu-miR-433-5p | 0 | 1.03 | 0.51 | UACGGUGAGCCUGUCAUUAUUC (151) |
| mmu-miR-181a-2* | 0 | 1.03 | 0.51 | ACCGACCGUUGACUGUACCUUG (152) |
| mmu-miR-218-2* | 0.26 | 0.77 | 0.52 | CAUGGUUCUGUCAAGCACCGCG (153) |
| mmu-miR-196a | 0.33 | 0.71 | 0.52 | UAGGUAGUUUCAUGUUGUUGGG (154) |
| mmu-miR-542-5p | 0.33 | 0.71 | 0.52 | CUCGGGGAUCAUCAUGUCACGA (155) |
| mmu-miR-7 | 0.55 | 0.49 | 0.52 | UGGAAGACUAGUGAUUUUGUUGU (156) |
| mmu-miR-743b-5p | 0.13 | 0.91 | 0.52 | UGUUCAGACUGGUGUCCAUCA (157) |
| mmu-miR-377 | 0.77 | 0.27 | 0.52 | AUCACACAAAGGCAACUUUUGU (158) |
| mmu-miR-683 | 0.77 | 0.27 | 0.52 | CCUGCUGUAAGCUGUGUCCUC (159) |
| mmu-miR-675-5p | 0.86 | 0.19 | 0.53 | UGGUGCGGAAAGGGCCCACAGU (160) |
| mmu-miR-598 | 0.52 | 0.54 | 0.53 | UACGUCAUCGUCGUCAUCGUUA (161) |
| mmu-miR-15b* | 0.12 | 0.95 | 0.53 | CGAAUCAUUAUUUGCUGCUCUA (162) |
| mmu-miR-9 | 0.66 | 0.42 | 0.54 | UCUUUGGUUAUCUAGCUGUAUGA (163) |
| mmu-miR-450a-3p | 0.33 | 0.75 | 0.54 | AUUGGGGAUGCUUUGCAUUCAU (164) |
| mmu-miR-449b | 0.33 | 0.75 | 0.54 | AGGCAGUGUUGUUAGCUGGC (165) |
| mmu-miR-707 | 0.14 | 0.94 | 0.54 | CAGUCAUGCCGCUUGCCUACG (166) |
| mmu-miR-335-3p | 0.52 | 0.56 | 0.54 | UUUUUCAUUAUUGCUCCUGACC (167) |
| mmu-miR-147 | 0.39 | 0.7 | 0.55 | GUGUGCGGAAAUGCUUCUGCUA (168) |
| mmu-miR-466c-5p | 0.26 | 0.84 | 0.55 | GAUGUGUGUGUGCAUGUACAUA (169) |
| mmu-miR-16 | 0.24 | 0.87 | 0.55 | UAGCAGCACGUAAAUAUUGGCG (170) |
| mmu-miR-127 | 0.77 | 0.35 | 0.56 | UCGGAUCCGUCUGAGCUUGGCU (171) |
| mmu-miR-673-3p | 0.7 | 0.43 | 0.56 | UCCGGGGCUGAGUUCUGUGCACC (172) |
| mmu-miR-466b-5p | 0.22 | 0.91 | 0.56 | GAUGUGUGUGUACAUGUACAUG (173) |
| mmu-miR-27a* | 0.22 | 0.91 | 0.56 | AGGGCUUAGCUGCUUGUGAGCA (174) |
| mmu-miR-1 | 0.35 | 0.78 | 0.57 | UGGAAUGUAAAGAAGUAUGUAU (175) |
| mmu-miR-201 | 0.22 | 0.92 | 0.57 | UACUCAGUAAGGCAUUGUUCUU (176) |
| mmu-miR-376b | 0.22 | 0.92 | 0.57 | AUCAUAGAGGAACAUCCACUU (177) |
| mmu-miR-187 | 0.12 | 1.03 | 0.57 | UCGUGUCUUGUGUUGCAGCCGG (178) |
| mmu-miR-299 | 0.12 | 1.03 | 0.57 | UGGUUUACCGUCCCACAUACAU (179) |
| mmu-miR-299 | 0.39 | 0.77 | 0.58 | UAUGUGGGACGGUAAACCGCUU (180) |
| mmu-miR-574-3p | 0.39 | 0.77 | 0.58 | CACGCUCAUGCACACACCCACA (181) |
| mmu-miR-193* | 0.39 | 0.77 | 0.58 | UGGGUCUUUGCGGGCAAGAUGA (182) |
| mmu-miR-679 | 0.48 | 0.69 | 0.59 | GGACUGUGAGGUGACUCUUGGU (183) |
| mmu-miR-540-5p | 0.26 | 0.91 | 0.59 | CAAGGGUCACCCUCUGACUCUGU (184) |
| mmu-miR-466a-5p | 0.26 | 0.91 | 0.59 | UAUGUGUGUGUACAUGUACAUA (185) |
| mmu-miR-470 | 0.33 | 0.85 | 0.59 | UUCUUGGACUGGCACUGGUGAGU (186) |

-continued

| microRNA mimic | exp. 1 | exp. 2 | Ave. | sequence (SEQ ID NO:) |
|---|---|---|---|---|
| mmu-miR-1224 | 0.77 | 0.41 | 0.59 | GUGAGGACUGGGGAGGUGGAG (187) |
| mmu-miR-191 | 0.55 | 0.64 | 0.59 | CAACGGAAUCCCAAAAGCAGCUG (188) |

Figure 20:
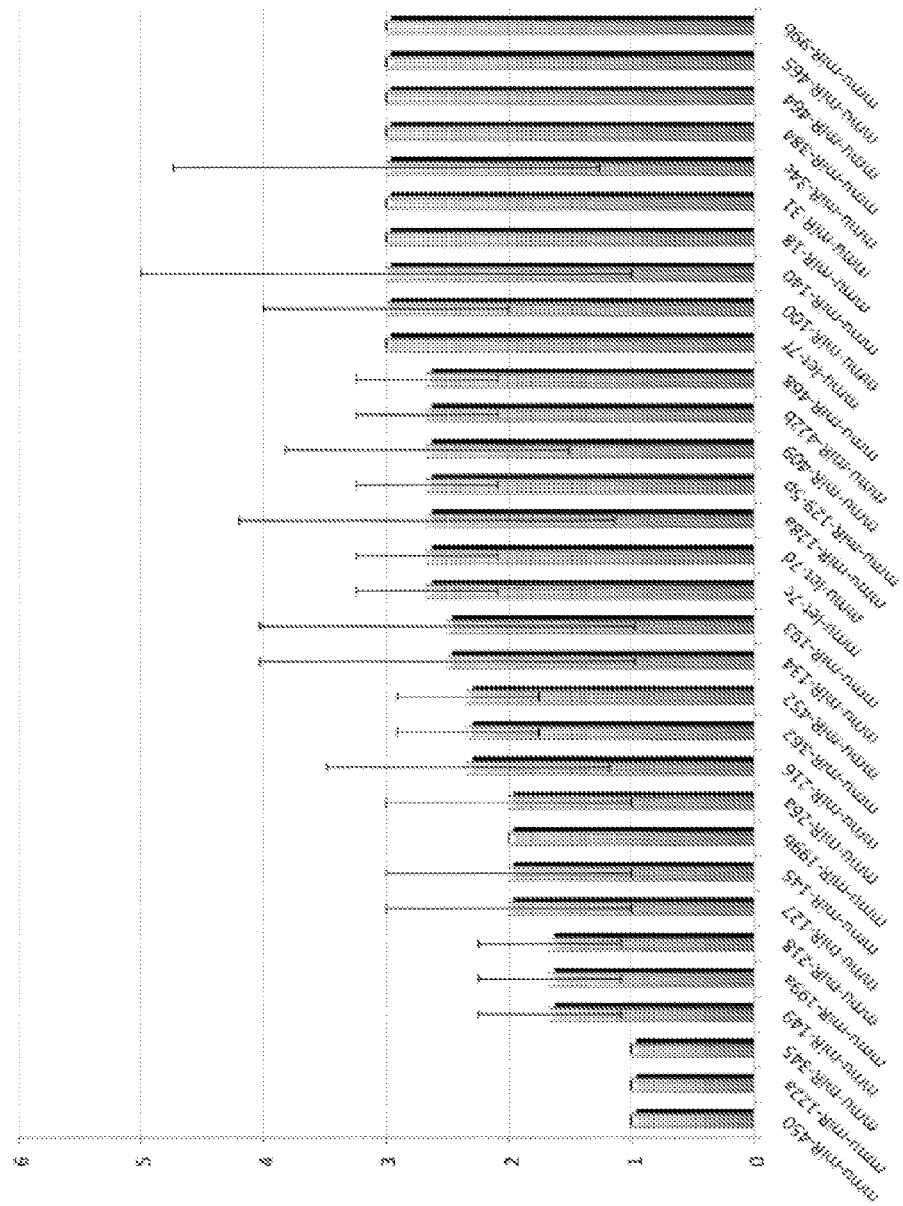
FIG. 20. Results of a screen assay for loss of ESC self-renewal in Dgcr8−/− ES cells after addition of individual miRNA mimics. Impact of miRNAs on ESC self-renewal was assayed by staining for alkaline phosphatase followed by blind scoring of amount of staining from 1-6. A score of 1 indicates the least amount of alkaline phosphatase staining and therefore the most silencing of ESC self-renewal. A score of 6 indicates high alkaline phosphatase staining and no silencing of ESC self-renewal. The screen was repeated in triplicated. Shown here are the mean of the triplicate+−standard deviation. Only miRNAs with a score at or below 3 are included in this figure. MiRNAs shown here are capable of silencing ESC self-renewal in Dgcr8−/− ESCs.
Figure 21:
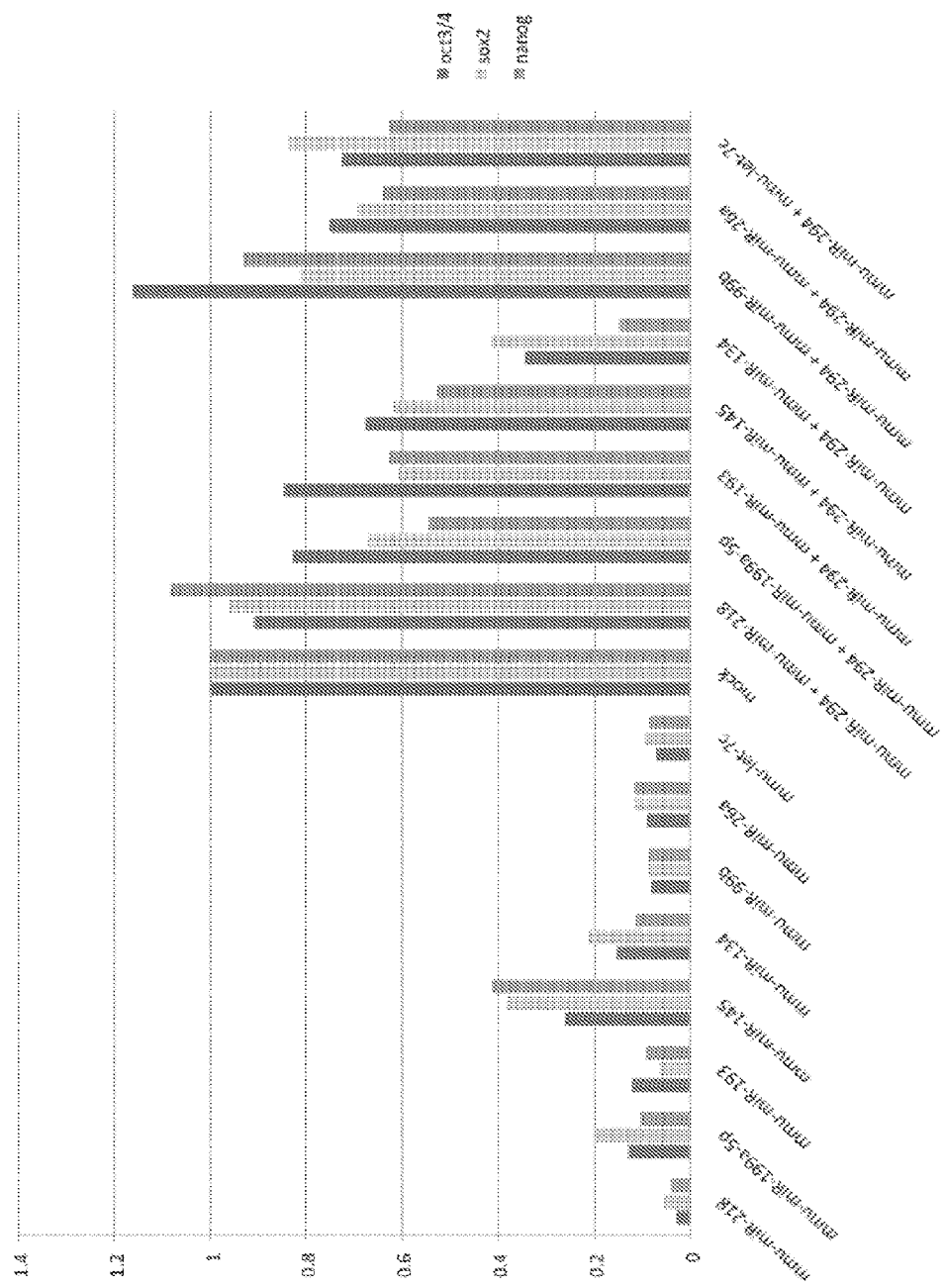
FIG. 21. Results of an experiment introducing select screen positive miRNAs (from FIG. 20) into Dgcr8−/− ESCs either alone or in combination with the ESCC miRNA miR-294. The data are the relative mRNA expression values of oct3/4, sox2, and nanog as measured by qRTPCR 3 days after introduction of the miRNA mimics. These data indicate that the screen positive miRNAs silence ESC self-renewal but only in the absence of ESCC miRNAs. The findings support silencing ESC self-renewal in ES or iPS cells by inhibition of ESCCs in combination with introduction of screen positive miRNAs.

Example 6 miRNA sequences of FIG. 20.

| MicroRNA | Accession No. | Sequence (SEQ ID NO:) |
|---|---|---|
| hsa-miR-199b-5p | MIMAT0000263 | CCCAGUGUUUAGACUAUCUGUUC (189) |
| hsa-let-7a | MIMAT0000062 | UGAGGUAGUAGGUUGUAUAGUU (190) |
| hsa-let-7b | MIMAT0000063 | UGAGGUAGUAGGUUGUGUGGUU (191) |
| hsa-let-7c | MIMAT0000064 | UGAGGUAGUAGGUUGUAUGGUU (192) |
| hsa-let-7d | MIMAT0000065 | AGAGGUAGUAGGUUGCAUAGUU (193) |
| hsa-let-7e | MIMAT0000066 | UGAGGUAGGAGGUUGUAUAGUU (194) |
| hsa-let-7f | MIMAT0000067 | UGAGGUAGUAGAUUGUAUAGUU (195) |
| hsa-let-7g | MIMAT0000414 | UGAGGUAGUAGUUUGUACAGUU (196) |
| hsa-let-7i | MIMAT0000415 | UGAGGUAGUAGUUUGUGCUGUU (197) |
| hsa-miR-100 | MIMAT0000098 | AACCCGUAGAUCCGAACUUGUG (198) |
| hsa-miR-100 | MIMAT0000098 | AACCCGUAGAUCCGAACUUGUG (199) |
| hsa-miR-122 | MIMAT0000421 | UGGAGUGUGACAAUGGUGUUUG (200) |
| hsa-miR-127-3p | MIMAT0000446 | UCGGAUCCGUCUGAGCUUGGCU (201) |
| hsa-miR-128 | MIMAT0000424 | UCACAGUGAACCGGUCUCUUU (202) |
| hsa-miR-129-5p | MIMAT0000242 | CUUUUUGCGGUCUGGGCUUGC (203) |
| hsa-miR-134 | MIMAT0000447 | UGUGACUGGUUGACCAGAGGGG (204) |
| hsa-miR-140-5p | MIMAT0000431 | CAGUGGUUUUACCCUAUGGUAG (205) |
| hsa-miR-145 | MIMAT0000437 | GUCCAGUUUUCCCAGGAAUCCCU (206) |
| hsa-miR-149 | MIMAT0000450 | UCUGGCUCCGUGUCUUCACUCCC (207) |
| hsa-miR-18a | MIMAT0000072 | UAAGGUGCAUCUAGUGCAGAUAG (208) |

-continued

| MicroRNA | Accession No. | Sequence (SEQ ID NO:) |
|---|---|---|
| hsa-miR-18b | MIMAT0001412 | UAAGGUGCAUCUAGUGCAGUUAG (209) |
| hsa-miR-193a-3p | MIMAT0000459 | AACUGGCCUACAAAGUCCCAGU (210) |
| hsa-miR-199a-5p | MIMAT0000231 | CCCAGUGUUCAGACUACCUGUUC (211) |
| hsa-miR-216a | MIMAT0000273 | UAAUCUCAGCUGGCAACUGUGA (212) |
| hsa-miR-216b | MIMAT0004959 | AAAUCUCUGCAGGCAAAUGUGA (213) |
| hsa-miR-218 | MIMAT0000275 | UUGUGCUUGAUCUAACCAUGU (214) |
| hsa-miR-26a | MIMAT0000082 | UUCAAGUAAUCCAGGAUAGGCU (215) |
| hsa-miR-31 | MIMAT0000089 | AGGCAAGAUGCUGGCAUAGCU (216) |
| hsa-miR-345 | MIMAT0000772 | GCUGACUCCUAGUCCAGGGCUC (217) |
| hsa-miR-34c-5p | MIMAT0000686 | AGGCAGUGUAGUUAGCUGAUUGC (218) |
| hsa-miR-362-5p | MIMAT0000705 | AAUCCUUGGAACCUAGGUGUGAGU (219) |
| hsa-miR-378 | MIMAT0000732 | ACUGGACUUGGAGUCAGAAGG (220) |
| hsa-miR-384 | MIMAT0001075 | AUUCCUAGAAAUUGUUCAUA (221) |
| hsa-miR-409-3p | MIMAT0001639 | GAAUGUUGCUCGGUGAACCCCU (222) |
| hsa-miR-450a | MIMAT0001545 | UUUUGCGAUGUGUUCCUAAUAU (223) |
| hsa-miR-450b-5p | MIMAT0004909 | UUUUGCAAUAUGUUCCUGAAUA (224) |
| hsa-miR-452 | MIMAT0001635 | AACUGUUUGCAGAGGAAACUGA (225) |
| hsa-miR-98 | MIMAT0000096 | UGAGGUAGUAAGUUGUAUUGUU (226) |
| hsa-miR-99a | MIMAT0000097 | AACCCGUAGAUCCGAUCUUGUG (227) |
| hsa-miR-99b | MIMAT0000689 | CACCCGUAGAACCGACCUUGCG (228) |
| mmu-let-7a | MIMAT0000521 | UGAGGUAGUAGGUUGUAUAGUU (229) |
| mmu-let-7b | MIMAT0000522 | UGAGGUAGUAGGUUGUGUGGUU (230) |

-continued

| MicroRNA | Accession No. | Sequence (SEQ ID NO:) |
|---|---|---|
| mmu-let-7c | MIMAT0000523 | UGAGGUAGUAGGUUGUAUGGUU (231) |
| mmu-let-7d | MIMAT0000383 | AGAGGUAGUAGGUUGCAUAGUU (232) |
| mmu-let-7e | MIMAT0000524 | UGAGGUAGGAGGUUGUAUAGUU (233) |
| mmu-let-7f | MIMAT0000525 | UGAGGUAGUAGAUUGUAUAGUU (234) |
| mmu-let-7g | MIMAT0000121 | UGAGGUAGUAGUUUGUACAGUU (235) |
| mmu-let-7i | MIMAT0000122 | UGAGGUAGUAGUUUGUGCUGUU (236) |
| mmu-miR-100 | MIMAT0000655 | AACCCGUAGAUCCGAACUUGUG (237) |
| mmu-miR-100 | MIMAT0000655 | AACCCGUAGAUCCGAACUUGUG (238) |
| mmu-miR-122 | MIMAT0000246 | UGGAGUGUGACAAUGGUGUUUG (239) |
| mmu-miR-127 | MIMAT0000139 | UCGGAUCCGUCUGAGCUUGGCU (240) |
| mmu-miR-128 | MIMAT0000140 | UCACAGUGAACCGGUCUCUUU (241) |
| mmu-miR-129-5p | MIMAT0000209 | CUUUUUGCGGUCUGGGCUUGC (242) |
| mmu-miR-134 | MIMAT0000146 | UGUGACUGGUUGACCAGAGGGG (243) |
| mmu-miR-140 | MIMAT0000151 | CAGUGGUUUUACCCUAUGGUAG (244) |
| mmu-miR-145 | MIMAT0000157 | GUCCAGUUUUCCCAGGAAUCCCU (245) |
| mmu-miR-149 | MIMAT0000159 | UCUGGCUCCGUGUCUUCACUCCC (246) |
| mmu-miR-18a | MIMAT0000528 | UAAGGUGCAUCUAGUGCAGAUAG (247) |
| mmu-miR-18b | MIMAT0004858 | UAAGGUGCAUCUAGUGCUGUUAG (248) |
| mmu-miR-193 | MIMAT0000223 | AACUGGCCUACAAAGUCCCAGU (249) |
| mmu-miR-199a-5p | MIMAT0000229 | CCCAGUGUUCAGACUACCUGUUC (250) |
| mmu-miR-199b | MIMAT0004667 | ACAGUAGUCUGCACAUUGGUUA (251) |
| mmu-miR-216a | MIMAT0000662 | UAAUCUCAGCUGGCAACUGUGA (252) |
| mmu-miR-216b | MIMAT0003729 | AAAUCUCUGCAGGCAAAUGUGA (253) |
| mmu-miR-218 | MIMAT0000663 | UUGUGCUUGAUCUAACCAUGU (254) |
| mmu-miR-26a | MIMAT0000533 | UUCAAGUAAUCCAGGAUAGGCU (255) |
| mmu-miR-31 | MIMAT0000538 | AGGCAAGAUGCUGGCAUAGCUG (256) |
| mmu-miR-345 | MIMAT0000595 | GCUGACCCCUAGUCCAGUGCUU (257) |
| mmu-miR-34c | MIMAT0000381 | AGGCAGUGUAGUUAGCUGAUUGC (258) |
| mmu-miR-362-5p | MIMAT0000706 | AAUCCUUGGAACCUAGGUGUGAAU (259) |
| mmu-miR-378 (old mmu-miR-422b) | MIMAT0003151 | ACUGGACUUGGAGUCAGAAGG (260) |
| mmu-miR-384-3p | MIMAT0001076 | AUUCCUAGAAAUUGUUCACAAU (261) |
| mmu-miR-409-3p | MIMAT0001090 | GAAUGUUGCUCGGUGAACCCCU (262) |
| mmu-miR-450a-5p | MIMAT0001546 | UUUUGCGAUGUGUUCCUAAUAU (263) |
| mmu-miR-450b-5p | MIMAT0003511 | UUUUGCAGUAUGUUCCUGAAUA (264) |
| mmu-miR-452 | MIMAT0001637 | UGUUUGCAGAGGAAACUGAGAC (265) |
| mmu-miR-464 | MIMAT0002105 | UACCAAGUUUAUUCUGUGAGAUA (266) |
| mmu-miR-465a-5p | MIMAT0002106 | UAUUUAGAAUGGCACUGAUGUGA (267) |
| mmu-miR-465b-5p | MIMAT0004871 | UAUUUAGAAUGGUGCUGAUCUG (268) |
| mmu-miR-465c-5p | MIMAT0004873 | UAUUUAGAAUGGCGCUGAUCUG (269) |
| mmu-miR-468 | | UAUGACUGAUGUGCGUGUGUCUG (270) |
| mmu-miR-98 | MIMAT0000545 | UGAGGUAGUAAGUUGUAUUGUU (271) |
| mmu-miR-99a | MIMAT0000131 | AACCCGUAGAUCCGAUCUUGUG (272) |
| mmu-miR-99b | MIMAT0000132 | CACCCGUAGAACCGACCUUGCG (273) |
| old mmu-miR-422b | | CUGGACUUGGAGUCAGAAGGC (274) |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including but not limited to those listed below, are hereby incorporated by reference in their entirety for all purposes.

REFERENCES

1. Babiarz, J. E. et al., The Stem Cell Research Community, StemBook, doi/10.3824/stembook. 1.47.1. (2009).
2. Hornstein, E. et al., *Nat. Genet* 38:S20-24 (2006).

3. Wang, Y. et al., *Nat Genet* 39:380-5 (2007).
4. Kanellopoulou, C. et al. *Genes Dev* 19:489-501 (2005).
5. Murchison, E. P. et al., *Proc Natl Acad Sci USA* 102:12135-40 (2005).
6. Wang, Y. et al. *Nat Genet* 40:1478-83 (2008).
7. Judson, R. et al., *Nat Biotech* (2009).
8. Landgraf, P. et al. *Cell* 129:1401-1414 (2007).
9. Chen, C. et al. *Mamm. Genome* 18:316-327 (2007).
10. Rybak, A. et al. *Nat Cell Biol* 10:987-93 (2008).
11. Viswanathan, S. R. et al., *Science* 320:97-100 (2008).
12. Heo, I. et al. *Mol Cell* 32:276-84 (2008).
13. Newman, M. A. et al., *RNA* 14:1539-49 (2008).
14. Thomson, J. M. et al. *Genes Dev* 20:2202-7 (2006).
15. Marson, A. et al. *Cell* 134:521-33 (2008).
16. Calabrese, J. M., *Proc. Natl. Acad. Sci. U.S.A* 104:18097-18102 (2007).
17. Benetti, R. et al., *Nat Struct Mol Biol* 15 (3):268-279 (2008).
18. Sinkkonen, L. et al., *Nat Struct Mol Biol* 15 (3):259-267 (2008).
19. Chen, X. et al. *Cell* 133:1106-17 (2008).
20. Kumar, M. S. et al., *Nat Genet* 39:673-677 (2007).
21. Kim, J. et al., *Cell* 132:1049-61 (2008).
22. Piskounova, E. et al. *J Biol Chem* 283:21310-4 (2008).
23. Lim, C. Y. et al. *Cell Stem Cell* 3:543-54 (2008).
24. Wu, Q. et al. *J Biol Chem* 281:24090-4 (2006).
25. Zhang, J. et al. *Nat Cell Biol* 8:1114-23 (2006).
26. Heo, I. et al. *Cell* 138:696-708 (2009).
27. Xu, B. et al., *RNA* 15:357-361 (2009).
28. Jones, M. R. et al. *Nat. Cell Biol* 11:1157-1163 (2009).
29. Polesskaya, A. et al. *Genes Dev* 21:1125-1138 (2007).
30. Yu, J. et al. *Science* 318:1917-1920 (2007).
31. Nakagawa, M. et al. *Nat. Biotechnol* 26:101-106 (2008).
32. Wernig, M. et al., *Cell Stem Cell* 2:10-12 (2008).
33. Stadtfeld, M. et al., *Cell Stem Cell* 2:230-240 (2008).
34. Brambrink, T. et al. *Cell Stem Cell* 2:151-159 (2008).
35. Hochedlinger, K. et al., *Development* 136 (4):509-523 (2009).
36. Cartwright, P. et al. *Development* 132:885-96 (2005).
37. Tay, Y. M. et al. *Stem Cells* 26:17-29 (2008).
38. Tay, Y. et al., *Nature* 455:1124-8 (2008).
39. Xu, N. et al., *Cell* 137:647-658 (2009).
40. Mendell, J. T. *Cell* 133:217-222 (2008).
41. Bussing, I. et al., *Trends in Molecular Medicine* 14:400-409 (2008).

The invention claimed is:

1. A method of inducing pluripotency in an isolated cell comprising:
   (a) introducing a vector(s) encoding the reprogramming factors Oct-4, Sox2, KLF-4 (OSK) into the cell;
   (b) introducing an inhibitor of a member of the let-7 family, wherein the member of the let-7 family has the seed sequence GAGGUAG and the inhibitor comprises a sequence complementary to the seed sequence GAGGUAG; and
   (c) culturing the cell from step (b) to produce a pluripotent cell, wherein the inhibitor and the expression of the reprogramming factors results in an enhanced production of pluripotent cells when compared to introduction of the reprogramming factors in the absence of the inhibitor.

2. The method of claim 1, wherein the inhibitor inhibits at least two let-7 family members simultaneously.

3. The method of claim 1, further comprising introducing a physiologically relevant miRNA into the cell, wherein the relevant miRNA contains the seed sequence AAGUGCU (SEQ ID NO:15), AAAGUGC (SEQ ID NO:16) or AAGUGC.

4. The method of claim 3, wherein the relevant miRNA is a member of the embryonic stem cell cycle (ESCC) regulating miR-290 cluster.

5. The method of claim 3, wherein the relevant miRNA is a member of the embryonic stem cell cycle (ESCC) regulating 302 cluster, 17-92 cluster, 106a, and 370 family of human miRNAs.

6. The method of claim 3, wherein the relevant miRNA is a human or mouse miRNA.

7. The method of claim 1, wherein the cell is a human cell.

8. The method of claim 7, wherein the human cell is a somatic cell.

9. The method of claim 3, wherein the relevant miRNA is
   (i) 80% or more identical to one of miR-291-3p (SEQ ID NO:1), miR-294 (SEQ ID NO:2), miR-295 (SEQ ID NO:3), miR-302d (SEQ ID NO:4), miR-292-3p (SEQ ID NO:5), hsa-mir-302a (SEQ ID NO:8), hsa-miR-302b (SEQ ID NO:9), hsa-miR-302c (SEQ ID NO:10), hsa-miR-302d (SEQ ID NO:11), hsa-miR-372 (SEQ ID NO:13); hsa-miR-373 (SEQ ID NO:14), hsa-miR-17 (SEQ ID NO:17), hsa-miR-20a (SEQ ID NO:18), hsa-miR-20b (SEQ ID NO:19), hsa-miR-93 (SEQ ID NO:20), hsa-miR-106a (SEQ ID NO:21), or hsa-miR-106b (SEQ ID NO:22); and
   (ii) contains the seed sequence AAGUGCU (SEQ ID NO:15), AAAGUGC (SEQ ID NO:16) or AAGUGC.

10. The method of claim 3, wherein the miR-290 cluster member is one of miR-291-3p (SEQ ID NO:1), miR-294 (SEQ ID NO:2) miR-295 (SEQ ID NO:3), miR-302d (SEQ ID NO:4), miR-292-3p (SEQ ID NO:5), hsa-mir-302a (SEQ ID NO:8), hsa-miR-302b (SEQ ID NO:9), hsa-miR-302c (SEQ ID NO:10), hsa-miR-302d (SEQ ID NO:11), hsa-miR371-5p (SEQ ID NO:12), hsa-miR-372 (SEQ ID NO:13), or hsa-miR-373 (SEQ ID NO:14).

11. The method of claim 3, wherein the miRNA that contains the seed sequence AAGUGCU (SEQ ID NO:15), AAAGUGC (SEQ ID NO:16) or AAGUGC is a miRNA of Example 3 or Example 4 or a human ortholog thereof.

* * * * *

SEQUENCE LISTING

```
<160> NUMBER OF SEQ ID NOS: 299

<210> SEQ ID NO 1
<211> LENGTH: 22
<212> TYPE: RNA
<213> ORGANISM: Artificial Sequence
<220> FEATURE:
<223> OTHER INFORMATION: synthetic miRNA miR-291-3p

<400> SEQUENCE: 1
aaagugcuuc cacuuugugu gc                                                  22

<210> SEQ ID NO 2
<211> LENGTH: 22
<212> TYPE: RNA
<213> ORGANISM: Artificial Sequence
<220> FEATURE:
<223> OTHER INFORMATION: synthetic miRNA miR-294

<400> SEQUENCE: 2
aaagugcuuc ccuuugugu gu                                                   22

<210> SEQ ID NO 3
<211> LENGTH: 23
<212> TYPE: RNA
<213> ORGANISM: Artificial Sequence
<220> FEATURE:
<223> OTHER INFORMATION: synthetic miRNA miR-295

<400> SEQUENCE: 3
aaagugcuac uacuuugag ucu                                                  23

<210> SEQ ID NO 4
<211> LENGTH: 23
<212> TYPE: RNA
<213> ORGANISM: Artificial Sequence
<220> FEATURE:
<223> OTHER INFORMATION: synthetic miRNA miR-302d

<400> SEQUENCE: 4
uaagugcuuc cauguuugag ugu                                                 23
```

```
<210> SEQ ID NO 5
<211> LENGTH: 24
<212> TYPE: RNA
<213> ORGANISM: Artificial Sequence
<220> FEATURE:
<223> OTHER INFORMATION: synthetic miRNA miR-292-3p

<400> SEQUENCE: 5
aaagugccgc cagguuuuga gugu                                           24

<210> SEQ ID NO 6
<211> LENGTH: 22
<212> TYPE: RNA
<213> ORGANISM: Artificial Sequence
<220> FEATURE:
<223> OTHER INFORMATION: synthetic miRNA miR-293

<400> SEQUENCE: 6
agugccgcag aguuuguagu gu                                             22

<210> SEQ ID NO 7
<211> LENGTH: 22
<212> TYPE: RNA
<213> ORGANISM: Artificial Sequence
<220> FEATURE:
<223> OTHER INFORMATION: synthetic miRNA miR-294 mut, mutant miR-294,
      miR-294 seed sequence mutant

<400> SEQUENCE: 7
aaauuucuuc ccuuuugugu gu                                             22

<210> SEQ ID NO 8
<211> LENGTH: 23
<212> TYPE: RNA
<213> ORGANISM: Artificial Sequence
<220> FEATURE:
<223> OTHER INFORMATION: synthetic miRNA hsa-miR-302a

<400> SEQUENCE: 8
uaagugcuuc cauguuuugg uga                                            23

<210> SEQ ID NO 9
<211> LENGTH: 23
<212> TYPE: RNA
<213> ORGANISM: Artificial Sequence
<220> FEATURE:
<223> OTHER INFORMATION: synthetic miRNA hsa-miR-302b

<400> SEQUENCE: 9
uaagugcuuc cauguuuuag uag                                            23

<210> SEQ ID NO 10
<211> LENGTH: 23
<212> TYPE: RNA
<213> ORGANISM: Artificial Sequence
<220> FEATURE:
<223> OTHER INFORMATION: synthetic miRNA hsa-miR-302c

<400> SEQUENCE: 10
uaagugcuuc cauguuucag ugg                                            23

<210> SEQ ID NO 11
<211> LENGTH: 23
<212> TYPE: RNA
<213> ORGANISM: Artificial Sequence
<220> FEATURE:
```

<223> OTHER INFORMATION: synthetic miRNA hsa-miR-302d

<400> SEQUENCE: 11
uaagugcuuc cauguuugag ugu                                                    23

<210> SEQ ID NO 12
<211> LENGTH: 20
<212> TYPE: RNA
<213> ORGANISM: Artificial Sequence
<220> FEATURE:
<223> OTHER INFORMATION: synthetic miRNA hsa-miR-371-5p

<400> SEQUENCE: 12
acucaaacug uggggggcacu                                                       20

<210> SEQ ID NO 13
<211> LENGTH: 23
<212> TYPE: RNA
<213> ORGANISM: Artificial Sequence
<220> FEATURE:
<223> OTHER INFORMATION: synthetic miRNA hsa-miR-372

<400> SEQUENCE: 13
aaagugcugc gacauuugag cgu                                                    23

<210> SEQ ID NO 14
<211> LENGTH: 23
<212> TYPE: RNA
<213> ORGANISM: Artificial Sequence
<220> FEATURE:
<223> OTHER INFORMATION: synthetic miRNA hsa-miR-373

<400> SEQUENCE: 14
gaagugcuuc gauuuugggg ugu                                                    23

<210> SEQ ID NO 15
<211> LENGTH: 7
<212> TYPE: RNA
<213> ORGANISM: Artificial Sequence
<220> FEATURE:
<223> OTHER INFORMATION: synthetic embryonic stem cell cycle (ESCC)
    miRNA seed-sequence, miRNA seed sequence

<400> SEQUENCE: 15 aagugcu                                                                       7

<210> SEQ ID NO 16
<211> LENGTH: 7
<212> TYPE: RNA
<213> ORGANISM: Artificial Sequence
<220> FEATURE:
<223> OTHER INFORMATION: synthetic embryonic stem cell cycle (ESCC)
    miRNA seed-sequence, miRNA seed sequence

<400> SEQUENCE: 16 aaagugc                                                                       7

<210> SEQ ID NO 17
<211> LENGTH: 23
<212> TYPE: RNA
<213> ORGANISM: Artificial Sequence
<220> FEATURE:
<223> OTHER INFORMATION: synthetic miRNA hsa-miR-17

<400> SEQUENCE: 17
caaagugcuu acagugcagg uag                                                    23

<210> SEQ ID NO 18
<211> LENGTH: 23
<212> TYPE: RNA
<213> ORGANISM: Artificial Sequence
<220> FEATURE:
<223> OTHER INFORMATION: synthetic miRNA hsa-miR-20a

<400> SEQUENCE: 18
uaaagugcuu auagugcagg uag                                           23

<210> SEQ ID NO 19
<211> LENGTH: 23
<212> TYPE: RNA
<213> ORGANISM: Artificial Sequence
<220> FEATURE:
<223> OTHER INFORMATION: synthetic miRNA hsa-miR-20b

<400> SEQUENCE: 19
caaagugcuc auagugcagg uag                                           23

<210> SEQ ID NO 20
<211> LENGTH: 23
<212> TYPE: RNA
<213> ORGANISM: Artificial Sequence
<220> FEATURE:
<223> OTHER INFORMATION: synthetic miRNA hsa-miR-93

<400> SEQUENCE: 20
caaagugcug uucgugcagg uag                                           23

<210> SEQ ID NO 21
<211> LENGTH: 23
<212> TYPE: RNA
<213> ORGANISM: Artificial Sequence
<220> FEATURE:
<223> OTHER INFORMATION: synthetic miRNA hsa-miR-106a

<400> SEQUENCE: 21
aaaagugcuu acagugcagg uag                                           23

<210> SEQ ID NO 22
<211> LENGTH: 21
<212> TYPE: RNA
<213> ORGANISM: Artificial Sequence
<220> FEATURE:
<223> OTHER INFORMATION: synthetic miRNA hsa-miR-106b

<400> SEQUENCE: 22
uaaagugcug acagugcaga u                                             21

<210> SEQ ID NO 23
<211> LENGTH: 23
<212> TYPE: RNA
<213> ORGANISM: Artificial Sequence
<220> FEATURE:
<223> OTHER INFORMATION: synthetic microRNA mimic mmu-miR-302b

<400> SEQUENCE: 23
uaagugcuuc cauguuuuag uag                                           23

<210> SEQ ID NO 24
<211> LENGTH: 23
<212> TYPE: RNA
<213> ORGANISM: Artificial Sequence
<220> FEATURE:

```
<223> OTHER INFORMATION: synthetic microRNA mimic mmu-miR-302

<400> SEQUENCE: 24
uaagugcuuc cauguuuugg uga                                              23

<210> SEQ ID NO 25
<211> LENGTH: 22
<212> TYPE: RNA
<213> ORGANISM: Artificial Sequence
<220> FEATURE:
<223> OTHER INFORMATION: synthetic microRNA mimic mmu-miR-495

<400> SEQUENCE: 25
aaacaaacau ggugcacuuc uu                                               22

<210> SEQ ID NO 26
<211> LENGTH: 22
<212> TYPE: RNA
<213> ORGANISM: Artificial Sequence
<220> FEATURE:
<223> OTHER INFORMATION: synthetic microRNA mimic mmu-miR-26a

<400> SEQUENCE: 26
uucaaguaau ccaggauagg cu                                               22

<210> SEQ ID NO 27
<211> LENGTH: 22
<212> TYPE: RNA
<213> ORGANISM: Artificial Sequence
<220> FEATURE:
<223> OTHER INFORMATION: synthetic microRNA mimic mmu-miR-19a*

<400> SEQUENCE: 27
uaguuuugca uaguugcacu ac                                               22

<210> SEQ ID NO 28
<211> LENGTH: 23
<212> TYPE: RNA
<213> ORGANISM: Artificial Sequence
<220> FEATURE:
<223> OTHER INFORMATION: synthetic microRNA mimic mmu-miR-302d

<400> SEQUENCE: 28
uaagugcuuc cauguuugag ugu                                              23

<210> SEQ ID NO 29
<211> LENGTH: 23
<212> TYPE: RNA
<213> ORGANISM: Artificial Sequence
<220> FEATURE:
<223> OTHER INFORMATION: synthetic microRNA mimic mmu-miR-10b

<400> SEQUENCE: 29
uacccuguag aaccgaauuu gug                                              23

<210> SEQ ID NO 30
<211> LENGTH: 22
<212> TYPE: RNA
<213> ORGANISM: Artificial Sequence
<220> FEATURE:
<223> OTHER INFORMATION: synthetic microRNA mimic mmu-miR-294

<400> SEQUENCE: 30
aaagugcuuc ccuuuugugu gu                                               22
```

```
<210> SEQ ID NO 31
<211> LENGTH: 22
<212> TYPE: RNA
<213> ORGANISM: Artificial Sequence
<220> FEATURE:
<223> OTHER INFORMATION: synthetic microRNA mimic mmu-miR-302c

<400> SEQUENCE: 31
aagugcuucc auguuucagu gg                                              22

<210> SEQ ID NO 32
<211> LENGTH: 22
<212> TYPE: RNA
<213> ORGANISM: Artificial Sequence
<220> FEATURE:
<223> OTHER INFORMATION: synthetic microRNA mimic mmu-miR-183*

<400> SEQUENCE: 32
gugaauuacc gaagggccau aa                                              22

<210> SEQ ID NO 33
<211> LENGTH: 22
<212> TYPE: RNA
<213> ORGANISM: Artificial Sequence
<220> FEATURE:
<223> OTHER INFORMATION: synthetic microRNA mimic mmu-miR-200a

<400> SEQUENCE: 33
uaacacuguc ugguaacgau gu                                              22

<210> SEQ ID NO 34
<211> LENGTH: 22
<212> TYPE: RNA
<213> ORGANISM: Artificial Sequence
<220> FEATURE:
<223> OTHER INFORMATION: synthetic microRNA mimic mmu-miR-34c

<400> SEQUENCE: 34
aaucacuaac cacacagcca gg                                              22

<210> SEQ ID NO 35
<211> LENGTH: 22
<212> TYPE: RNA
<213> ORGANISM: Artificial Sequence
<220> FEATURE:
<223> OTHER INFORMATION: synthetic microRNA mimic mmu-miR-293

<400> SEQUENCE: 35
agugccgcag aguuuguagu gu                                              22

<210> SEQ ID NO 36
<211> LENGTH: 23
<212> TYPE: RNA
<213> ORGANISM: Artificial Sequence
<220> FEATURE:
<223> OTHER INFORMATION: synthetic microRNA mimic mmu-miR-181b

<400> SEQUENCE: 36
aacauucauu gcugucggug ggu                                             23

<210> SEQ ID NO 37
<211> LENGTH: 21
<212> TYPE: RNA
<213> ORGANISM: Artificial Sequence
<220> FEATURE:
<223> OTHER INFORMATION: synthetic microRNA mimic mmu-miR-151
```

```
<400> SEQUENCE: 37
cuagacugag gcuccuugag g                                              21

<210> SEQ ID NO 38
<211> LENGTH: 21
<212> TYPE: RNA
<213> ORGANISM: Artificial Sequence
<220> FEATURE:
<223> OTHER INFORMATION: synthetic microRNA mimic mmu-miR-680

<400> SEQUENCE: 38
gggcaucugc ugacaugggg g                                              21

<210> SEQ ID NO 39
<211> LENGTH: 23
<212> TYPE: RNA
<213> ORGANISM: Artificial Sequence
<220> FEATURE:
<223> OTHER INFORMATION: synthetic microRNA mimic mmu-miR-295

<400> SEQUENCE: 39
aaagugcuac uacuuuugag ucu                                            23

<210> SEQ ID NO 40
<211> LENGTH: 22
<212> TYPE: RNA
<213> ORGANISM: Artificial Sequence
<220> FEATURE:
<223> OTHER INFORMATION: synthetic microRNA mimic mmu-miR-880

<400> SEQUENCE: 40
uacuccaucc ucucugagua ga                                             22

<210> SEQ ID NO 41
<211> LENGTH: 23
<212> TYPE: RNA
<213> ORGANISM: Artificial Sequence
<220> FEATURE:
<223> OTHER INFORMATION: synthetic microRNA mimic mmu-miR-93

<400> SEQUENCE: 41
caaagugcug uucgugcagg uag                                            23

<210> SEQ ID NO 42
<211> LENGTH: 22
<212> TYPE: RNA
<213> ORGANISM: Artificial Sequence
<220> FEATURE:
<223> OTHER INFORMATION: synthetic microRNA mimic mmu-miR-455-5p

<400> SEQUENCE: 42
uaugugccuu uggacuacau cg                                             22

<210> SEQ ID NO 43
<211> LENGTH: 20
<212> TYPE: RNA
<213> ORGANISM: Artificial Sequence
<220> FEATURE:
<223> OTHER INFORMATION: synthetic microRNA mimic mmu-miR-144

<400> SEQUENCE: 43
uacaguauag augauguacu                                                20

<210> SEQ ID NO 44
<211> LENGTH: 22
```

```
<212> TYPE: RNA
<213> ORGANISM: Artificial Sequence
<220> FEATURE:
<223> OTHER INFORMATION: synthetic microRNA mimic mmu-miR-467d

<400> SEQUENCE: 44
uaagugcgcg cauguauaug cg                                              22

<210> SEQ ID NO 45
<211> LENGTH: 22
<212> TYPE: RNA
<213> ORGANISM: Artificial Sequence
<220> FEATURE:
<223> OTHER INFORMATION: synthetic microRNA mimic mmu-miR-484

<400> SEQUENCE: 45
ucaggcucag uccccucccg au                                              22

<210> SEQ ID NO 46
<211> LENGTH: 22
<212> TYPE: RNA
<213> ORGANISM: Artificial Sequence
<220> FEATURE:
<223> OTHER INFORMATION: synthetic microRNA mimic mmu-miR-205

<400> SEQUENCE: 46
uccuucauuc caccggaguc ug                                              22

<210> SEQ ID NO 47
<211> LENGTH: 22
<212> TYPE: RNA
<213> ORGANISM: Artificial Sequence
<220> FEATURE:
<223> OTHER INFORMATION: synthetic microRNA mimic mmu-miR-582-5p

<400> SEQUENCE: 47
uacaguuguu caaccaguua cu                                              22

<210> SEQ ID NO 48
<211> LENGTH: 24
<212> TYPE: RNA
<213> ORGANISM: Artificial Sequence
<220> FEATURE:
<223> OTHER INFORMATION: synthetic microRNA mimic mmu-miR-290-3p

<400> SEQUENCE: 48
aaagugccgc cuaguuuuaa gccc                                            24

<210> SEQ ID NO 49
<211> LENGTH: 22
<212> TYPE: RNA
<213> ORGANISM: Artificial Sequence
<220> FEATURE:
<223> OTHER INFORMATION: synthetic microRNA mimic mmu-miR-138*

<400> SEQUENCE: 49
cggcuacuuc acaacaccag gg                                              22

<210> SEQ ID NO 50
<211> LENGTH: 23
<212> TYPE: RNA
<213> ORGANISM: Artificial Sequence
<220> FEATURE:
<223> OTHER INFORMATION: synthetic microRNA mimic mmu-miR-181d

<400> SEQUENCE: 50
```
aacauucauu guugucggug ggu                                              23

<210> SEQ ID NO 51
<211> LENGTH: 20
<212> TYPE: RNA
<213> ORGANISM: Artificial Sequence
<220> FEATURE:
<223> OTHER INFORMATION: synthetic microRNA mimic mmu-miR-324-3p

<400> SEQUENCE: 51
ccacugcccc aggugcugcu                                                  20

<210> SEQ ID NO 52
<211> LENGTH: 22
<212> TYPE: RNA
<213> ORGANISM: Artificial Sequence
<220> FEATURE:
<223> OTHER INFORMATION: synthetic microRNA mimic mmu-miR-877*

<400> SEQUENCE: 52
uguccucuuc ucccuccucc ca                                               22

<210> SEQ ID NO 53
<211> LENGTH: 21
<212> TYPE: RNA
<213> ORGANISM: Artificial Sequence
<220> FEATURE:
<223> OTHER INFORMATION: synthetic microRNA mimic mmu-miR-23a

<400> SEQUENCE: 53
aucacauugc cagggauuuc c                                                21

<210> SEQ ID NO 54
<211> LENGTH: 21
<212> TYPE: RNA
<213> ORGANISM: Artificial Sequence
<220> FEATURE:
<223> OTHER INFORMATION: synthetic microRNA mimic mmu-miR-379

<400> SEQUENCE: 54
ugguagacua uggaacguag g                                                21

<210> SEQ ID NO 55
<211> LENGTH: 22
<212> TYPE: RNA
<213> ORGANISM: Artificial Sequence
<220> FEATURE:
<223> OTHER INFORMATION: synthetic microRNA mimic mmu-miR-673

<400> SEQUENCE: 55
cucacagcuc ugguccuugg ag                                               22

<210> SEQ ID NO 56
<211> LENGTH: 22
<212> TYPE: RNA
<213> ORGANISM: Artificial Sequence
<220> FEATURE:
<223> OTHER INFORMATION: synthetic microRNA mimic mmu-miR-876-5p

<400> SEQUENCE: 56
uggauuucuc ugugaaucac ua                                               22

<210> SEQ ID NO 57
<211> LENGTH: 22
<212> TYPE: RNA
<213> ORGANISM: Artificial Sequence

```
<220> FEATURE:
<223> OTHER INFORMATION: synthetic microRNA mimic mmu-miR-291-3p

<400> SEQUENCE: 57
aaagugcuuc cacuugugu gc                                              22

<210> SEQ ID NO 58
<211> LENGTH: 22
<212> TYPE: RNA
<213> ORGANISM: Artificial Sequence
<220> FEATURE:
<223> OTHER INFORMATION: synthetic microRNA mimic mmu-miR-30d

<400> SEQUENCE: 58
uguaaacauc cccgacugga ag                                             22

<210> SEQ ID NO 59
<211> LENGTH: 23
<212> TYPE: RNA
<213> ORGANISM: Artificial Sequence
<220> FEATURE:
<223> OTHER INFORMATION: synthetic microRNA mimic mmu-miR-421

<400> SEQUENCE: 59
aucaacagac auuaauuggg cgc                                            23

<210> SEQ ID NO 60
<211> LENGTH: 22
<212> TYPE: RNA
<213> ORGANISM: Artificial Sequence
<220> FEATURE:
<223> OTHER INFORMATION: synthetic microRNA mimic mmu-miR-879*

<400> SEQUENCE: 60
gcuuauggcu ucaagcuuuc gg                                             22

<210> SEQ ID NO 61
<211> LENGTH: 22
<212> TYPE: RNA
<213> ORGANISM: Artificial Sequence
<220> FEATURE:
<223> OTHER INFORMATION: synthetic microRNA mimic mmu-miR-542-3p

<400> SEQUENCE: 61
ugugacagau ugauaacuga aa                                             22

<210> SEQ ID NO 62
<211> LENGTH: 22
<212> TYPE: RNA
<213> ORGANISM: Artificial Sequence
<220> FEATURE:
<223> OTHER INFORMATION: synthetic microRNA mimic mmu-miR-124*

<400> SEQUENCE: 62
cguguucaca gcggaccuug au                                             22

<210> SEQ ID NO 63
<211> LENGTH: 22
<212> TYPE: RNA
<213> ORGANISM: Artificial Sequence
<220> FEATURE:
<223> OTHER INFORMATION: synthetic microRNA mimic mmu-miR-363

<400> SEQUENCE: 63
aauugcacgg uauccaucug ua                                             22
```

```
<210> SEQ ID NO 64
<211> LENGTH: 23
<212> TYPE: RNA
<213> ORGANISM: Artificial Sequence
<220> FEATURE:
<223> OTHER INFORMATION: synthetic microRNA mimic mmu-miR-871

<400> SEQUENCE: 64
uauucagauu agugccaguc aug                                              23

<210> SEQ ID NO 65
<211> LENGTH: 23
<212> TYPE: RNA
<213> ORGANISM: Artificial Sequence
<220> FEATURE:
<223> OTHER INFORMATION: synthetic microRNA mimic mmu-miR-19a

<400> SEQUENCE: 65
ugugcaaauc uaugcaaaac uga                                              23

<210> SEQ ID NO 66
<211> LENGTH: 22
<212> TYPE: RNA
<213> ORGANISM: Artificial Sequence
<220> FEATURE:
<223> OTHER INFORMATION: synthetic microRNA mimic mmu-miR-16*

<400> SEQUENCE: 66
ccaguauuga cugugcugcu ga                                               22

<210> SEQ ID NO 67
<211> LENGTH: 21
<212> TYPE: RNA
<213> ORGANISM: Artificial Sequence
<220> FEATURE:
<223> OTHER INFORMATION: synthetic microRNA mimic mmu-miR-873

<400> SEQUENCE: 67
gcaggaacuu gugagucucc u                                                21

<210> SEQ ID NO 68
<211> LENGTH: 23
<212> TYPE: RNA
<213> ORGANISM: Artificial Sequence
<220> FEATURE:
<223> OTHER INFORMATION: synthetic microRNA mimic mmu-miR-199b

<400> SEQUENCE: 68
cccaguguuu agacuaccug uuc                                              23

<210> SEQ ID NO 69
<211> LENGTH: 23
<212> TYPE: RNA
<213> ORGANISM: Artificial Sequence
<220> FEATURE:
<223> OTHER INFORMATION: synthetic microRNA mimic mmu-miR-106a

<400> SEQUENCE: 69
caaagugcua acagugcagg uag                                              23

<210> SEQ ID NO 70
<211> LENGTH: 23
<212> TYPE: RNA
<213> ORGANISM: Artificial Sequence
<220> FEATURE:
<223> OTHER INFORMATION: synthetic microRNA mimic mmu-miR-181b
```

```
<400> SEQUENCE: 70
aacauucauu gcugucggug ggu                                            23

<210> SEQ ID NO 71
<211> LENGTH: 22
<212> TYPE: RNA
<213> ORGANISM: Artificial Sequence
<220> FEATURE:
<223> OTHER INFORMATION: synthetic microRNA mimic mmu-miR-200a*

<400> SEQUENCE: 71
caucuuaccg gacagugcug ga                                             22

<210> SEQ ID NO 72
<211> LENGTH: 22
<212> TYPE: RNA
<213> ORGANISM: Artificial Sequence
<220> FEATURE:
<223> OTHER INFORMATION: synthetic microRNA mimic mmu-miR-431*

<400> SEQUENCE: 72
caggucgucu ugcagggcuu cu                                             22

<210> SEQ ID NO 73
<211> LENGTH: 21
<212> TYPE: RNA
<213> ORGANISM: Artificial Sequence
<220> FEATURE:
<223> OTHER INFORMATION: synthetic microRNA mimic mmu-miR-689

<400> SEQUENCE: 73 cgucccgcu cggcgggguc c                                               21

<210> SEQ ID NO 74
<211> LENGTH: 21
<212> TYPE: RNA
<213> ORGANISM: Artificial Sequence
<220> FEATURE:
<223> OTHER INFORMATION: synthetic microRNA mimic mmu-miR-721

<400> SEQUENCE: 74
cagugcaauu aaaaggggga a                                              21

<210> SEQ ID NO 75
<211> LENGTH: 22
<212> TYPE: RNA
<213> ORGANISM: Artificial Sequence
<220> FEATURE:
<223> OTHER INFORMATION: synthetic microRNA mimic mmu-miR-744*

<400> SEQUENCE: 75
cuguugccac uaaccucaac cu                                             22

<210> SEQ ID NO 76
<211> LENGTH: 23
<212> TYPE: RNA
<213> ORGANISM: Artificial Sequence
<220> FEATURE:
<223> OTHER INFORMATION: synthetic microRNA mimic mmu-miR-423-5p

<400> SEQUENCE: 76
ugaggggcag agagcgagac uuu                                            23

<210> SEQ ID NO 77
```

```
<211> LENGTH: 22
<212> TYPE: RNA
<213> ORGANISM: Artificial Sequence
<220> FEATURE:
<223> OTHER INFORMATION: synthetic microRNA mimic mmu-miR-669c

<400> SEQUENCE: 77
auaguugugu guggaugugu gu                                            22

<210> SEQ ID NO 78
<211> LENGTH: 22
<212> TYPE: RNA
<213> ORGANISM: Artificial Sequence
<220> FEATURE:
<223> OTHER INFORMATION: synthetic microRNA mimic mmu-let-7c

<400> SEQUENCE: 78
ugagguagua gguuguaugg uu                                            22

<210> SEQ ID NO 79
<211> LENGTH: 22
<212> TYPE: RNA
<213> ORGANISM: Artificial Sequence
<220> FEATURE:
<223> OTHER INFORMATION: synthetic microRNA mimic mmu-miR-466h

<400> SEQUENCE: 79
ugugugcaug ugcuugugug ua                                            22

<210> SEQ ID NO 80
<211> LENGTH: 22
<212> TYPE: RNA
<213> ORGANISM: Artificial Sequence
<220> FEATURE:
<223> OTHER INFORMATION: synthetic microRNA mimic mmu-miR-654-3p

<400> SEQUENCE: 80
uaugucugcu gaccaucacc uu                                            22

<210> SEQ ID NO 81
<211> LENGTH: 22
<212> TYPE: RNA
<213> ORGANISM: Artificial Sequence
<220> FEATURE:
<223> OTHER INFORMATION: synthetic microRNA mimic mmu-miR-470*

<400> SEQUENCE: 81
aaccaguacc uuucugagaa ga                                            22

<210> SEQ ID NO 82
<211> LENGTH: 22
<212> TYPE: RNA
<213> ORGANISM: Artificial Sequence
<220> FEATURE:
<223> OTHER INFORMATION: synthetic microRNA mimic mmu-miR-24

<400> SEQUENCE: 82
uggcucaguu cagcaggaac ag                                            22

<210> SEQ ID NO 83
<211> LENGTH: 25
<212> TYPE: RNA
<213> ORGANISM: Artificial Sequence
<220> FEATURE:
<223> OTHER INFORMATION: synthetic microRNA mimic mmu-miR-182

<400> SEQUENCE: 83
```
uuuggcaaug guagaacuca caccg                                              25

<210> SEQ ID NO 84
<211> LENGTH: 23
<212> TYPE: RNA
<213> ORGANISM: Artificial Sequence
<220> FEATURE:
<223> OTHER INFORMATION: synthetic microRNA mimic mmu-miR-335

<400> SEQUENCE: 84
ucaagagcaa uaacgaaaaa ugu                                                23

<210> SEQ ID NO 85
<211> LENGTH: 22
<212> TYPE: RNA
<213> ORGANISM: Artificial Sequence
<220> FEATURE:
<223> OTHER INFORMATION: synthetic microRNA mimic mmu-miR-181c

<400> SEQUENCE: 85
aacauucaac cugucgguga gu                                                 22

<210> SEQ ID NO 86
<211> LENGTH: 23
<212> TYPE: RNA
<213> ORGANISM: Artificial Sequence
<220> FEATURE:
<223> OTHER INFORMATION: synthetic microRNA mimic mmu-miR-330

<400> SEQUENCE: 86
gcaaagcaca gggccugcag aga                                                23

<210> SEQ ID NO 87
<211> LENGTH: 22
<212> TYPE: RNA
<213> ORGANISM: Artificial Sequence
<220> FEATURE:
<223> OTHER INFORMATION: synthetic microRNA mimic mmu-miR-134

<400> SEQUENCE: 87
ugugacuggu ugaccagagg gg                                                 22

<210> SEQ ID NO 88
<211> LENGTH: 22
<212> TYPE: RNA
<213> ORGANISM: Artificial Sequence
<220> FEATURE:
<223> OTHER INFORMATION: synthetic microRNA mimic mmu-miR-675-3p

<400> SEQUENCE: 88
cuguaugccc uaaccgcuca gu                                                 22

<210> SEQ ID NO 89
<211> LENGTH: 21
<212> TYPE: RNA
<213> ORGANISM: Artificial Sequence
<220> FEATURE:
<223> OTHER INFORMATION: synthetic microRNA mimic mmu-miR-218

<400> SEQUENCE: 89
uugugcuuga ucuaaccaug u                                                  21

<210> SEQ ID NO 90
<211> LENGTH: 22
<212> TYPE: RNA

<213> ORGANISM: Artificial Sequence
<220> FEATURE:
<223> OTHER INFORMATION: synthetic microRNA mimic mmu-let-7f

<400> SEQUENCE: 90
ugagguagua gauuguauag uu                                              22

<210> SEQ ID NO 91
<211> LENGTH: 22
<212> TYPE: RNA
<213> ORGANISM: Artificial Sequence
<220> FEATURE:
<223> OTHER INFORMATION: synthetic microRNA mimic mmu-miR-491

<400> SEQUENCE: 91 agugggaac ccuuccauga gg                                               22

<210> SEQ ID NO 92
<211> LENGTH: 21
<212> TYPE: RNA
<213> ORGANISM: Artificial Sequence
<220> FEATURE:
<223> OTHER INFORMATION: synthetic microRNA mimic mmu-miR-466g

<400> SEQUENCE: 92
auacagacac augcacacac a                                               21

<210> SEQ ID NO 93
<211> LENGTH: 22
<212> TYPE: RNA
<213> ORGANISM: Artificial Sequence
<220> FEATURE:
<223> OTHER INFORMATION: synthetic microRNA mimic mmu-miR-465c-3p

<400> SEQUENCE: 93
gaucagggcc uuucuaagua ga                                              22

<210> SEQ ID NO 94
<211> LENGTH: 22
<212> TYPE: RNA
<213> ORGANISM: Artificial Sequence
<220> FEATURE:
<223> OTHER INFORMATION: synthetic microRNA mimic mmu-miR-202

<400> SEQUENCE: 94
agagguauag cgcaugggaa ga                                              22

<210> SEQ ID NO 95
<211> LENGTH: 21
<212> TYPE: RNA
<213> ORGANISM: Artificial Sequence
<220> FEATURE:
<223> OTHER INFORMATION: synthetic microRNA mimic mmu-miR-681

<400> SEQUENCE: 95
cagccucgcu ggcaggcagc u                                               21

<210> SEQ ID NO 96
<211> LENGTH: 20
<212> TYPE: RNA
<213> ORGANISM: Artificial Sequence
<220> FEATURE:
<223> OTHER INFORMATION: synthetic microRNA mimic mmu-miR-877

<400> SEQUENCE: 96
guagaggaga uggcgcaggg                                                 20

```
<210> SEQ ID NO 97
<211> LENGTH: 22
<212> TYPE: RNA
<213> ORGANISM: Artificial Sequence
<220> FEATURE:
<223> OTHER INFORMATION: synthetic microRNA mimic mmu-miR-875-5p

<400> SEQUENCE: 97
uauaccucag uuuuaucagg ug                                              22

<210> SEQ ID NO 98
<211> LENGTH: 21
<212> TYPE: RNA
<213> ORGANISM: Artificial Sequence
<220> FEATURE:
<223> OTHER INFORMATION: synthetic microRNA mimic mmu-miR-712

<400> SEQUENCE: 98
cuccuucacc cgggcgguac c                                               21

<210> SEQ ID NO 99
<211> LENGTH: 22
<212> TYPE: RNA
<213> ORGANISM: Artificial Sequence
<220> FEATURE:
<223> OTHER INFORMATION: synthetic microRNA mimic mmu-miR-297

<400> SEQUENCE: 99
auguaugugu gcaugugcau gu                                              22

<210> SEQ ID NO 100
<211> LENGTH: 22
<212> TYPE: RNA
<213> ORGANISM: Artificial Sequence
<220> FEATURE:
<223> OTHER INFORMATION: synthetic microRNA mimic mmu-let-7d

<400> SEQUENCE: 100
agagguagua gguugcauag uu                                              22

<210> SEQ ID NO 101
<211> LENGTH: 23
<212> TYPE: RNA
<213> ORGANISM: Artificial Sequence
<220> FEATURE:
<223> OTHER INFORMATION: synthetic microRNA mimic mmu-miR-142-3p

<400> SEQUENCE: 101
uguaguguuu ccuacuuuau gga                                             23

<210> SEQ ID NO 102
<211> LENGTH: 22
<212> TYPE: RNA
<213> ORGANISM: Artificial Sequence
<220> FEATURE:
<223> OTHER INFORMATION: synthetic microRNA mimic mmu-miR-328

<400> SEQUENCE: 102
cuggcccucu cugcccuucc gu                                              22

<210> SEQ ID NO 103
<211> LENGTH: 22
<212> TYPE: RNA
<213> ORGANISM: Artificial Sequence
<220> FEATURE:
```

<223> OTHER INFORMATION: synthetic microRNA mimic mmu-miR-485-5p

<400> SEQUENCE: 103
agaggcuggc cgugaugaau uc                                           22

<210> SEQ ID NO 104
<211> LENGTH: 22
<212> TYPE: RNA
<213> ORGANISM: Artificial Sequence
<220> FEATURE:
<223> OTHER INFORMATION: synthetic microRNA mimic mmu-miR-122a

<400> SEQUENCE: 104
uggaguguga caauguguu ug                                            22

<210> SEQ ID NO 105
<211> LENGTH: 22
<212> TYPE: RNA
<213> ORGANISM: Artificial Sequence
<220> FEATURE:
<223> OTHER INFORMATION: synthetic microRNA mimic mmu-miR-877*

<400> SEQUENCE: 105
uguccucuuc ucccuccucc ca                                           22

<210> SEQ ID NO 106
<211> LENGTH: 23
<212> TYPE: RNA
<213> ORGANISM: Artificial Sequence
<220> FEATURE:
<223> OTHER INFORMATION: synthetic microRNA mimic mmu-miR-135a

<400> SEQUENCE: 106
uauggcuuuu uauuccuaug uga                                          23

<210> SEQ ID NO 107
<211> LENGTH: 22
<212> TYPE: RNA
<213> ORGANISM: Artificial Sequence
<220> FEATURE:
<223> OTHER INFORMATION: synthetic microRNA mimic mmu-miR-674-3p

<400> SEQUENCE: 107
cacagcuccc aucucagaac aa                                           22

<210> SEQ ID NO 108
<211> LENGTH: 22
<212> TYPE: RNA
<213> ORGANISM: Artificial Sequence
<220> FEATURE:
<223> OTHER INFORMATION: synthetic microRNA mimic mmu-miR-497

<400> SEQUENCE: 108
cagcagcaca cugugguuug ua                                           22

<210> SEQ ID NO 109
<211> LENGTH: 23
<212> TYPE: RNA
<213> ORGANISM: Artificial Sequence
<220> FEATURE:
<223> OTHER INFORMATION: synthetic microRNA mimic mmu-miR-7b

<400> SEQUENCE: 109
uggaagacuu gugauuuugu ugu                                          23

```
<210> SEQ ID NO 110
<211> LENGTH: 22
<212> TYPE: RNA
<213> ORGANISM: Artificial Sequence
<220> FEATURE:
<223> OTHER INFORMATION: synthetic microRNA mimic mmu-miR-30b*

<400> SEQUENCE: 110
cugggaugug gauguuuacg uc                                              22

<210> SEQ ID NO 111
<211> LENGTH: 23
<212> TYPE: RNA
<213> ORGANISM: Artificial Sequence
<220> FEATURE:
<223> OTHER INFORMATION: synthetic microRNA mimic mmu-miR-34b

<400> SEQUENCE: 111
aggcagugua auuagcugau ugu                                             23

<210> SEQ ID NO 112
<211> LENGTH: 22
<212> TYPE: RNA
<213> ORGANISM: Artificial Sequence
<220> FEATURE:
<223> OTHER INFORMATION: synthetic microRNA mimic mmu-miR-466e-5p

<400> SEQUENCE: 112
gaugugugug uacauguaca ua                                              22

<210> SEQ ID NO 113
<211> LENGTH: 22
<212> TYPE: RNA
<213> ORGANISM: Artificial Sequence
<220> FEATURE:
<223> OTHER INFORMATION: synthetic microRNA mimic mmu-miR-193b

<400> SEQUENCE: 113
aacuggccca caaagucccg cu                                              22

<210> SEQ ID NO 114
<211> LENGTH: 22
<212> TYPE: RNA
<213> ORGANISM: Artificial Sequence
<220> FEATURE:
<223> OTHER INFORMATION: synthetic microRNA mimic mmu-miR-883a-5p

<400> SEQUENCE: 114
ugcugagaga aguagcaguu ac                                              22

<210> SEQ ID NO 115
<211> LENGTH: 22
<212> TYPE: RNA
<213> ORGANISM: Artificial Sequence
<220> FEATURE:
<223> OTHER INFORMATION: synthetic microRNA mimic mmu-let-7i*

<400> SEQUENCE: 115
cugcgcaagc uacugccuug cu                                              22

<210> SEQ ID NO 116
<211> LENGTH: 23
<212> TYPE: RNA
<213> ORGANISM: Artificial Sequence
<220> FEATURE:
<223> OTHER INFORMATION: synthetic microRNA mimic mmu-miR-342
```

```
<400> SEQUENCE: 116
ucucacacag aaaucgcacc cgu                                              23

<210> SEQ ID NO 117
<211> LENGTH: 21
<212> TYPE: RNA
<213> ORGANISM: Artificial Sequence
<220> FEATURE:
<223> OTHER INFORMATION: synthetic microRNA mimic mmu-miR-140*

<400> SEQUENCE: 117
uaccacaggg uagaaccacg g                                                21

<210> SEQ ID NO 118
<211> LENGTH: 22
<212> TYPE: RNA
<213> ORGANISM: Artificial Sequence
<220> FEATURE:
<223> OTHER INFORMATION: synthetic microRNA mimic mmu-miR-24-2*

<400> SEQUENCE: 118
gugccuacug agcugaaaca gu                                               22

<210> SEQ ID NO 119
<211> LENGTH: 21
<212> TYPE: RNA
<213> ORGANISM: Artificial Sequence
<220> FEATURE:
<223> OTHER INFORMATION: synthetic microRNA mimic mmu-miR-195

<400> SEQUENCE: 119
uagcagcaca gaaauauugg c                                                21

<210> SEQ ID NO 120
<211> LENGTH: 22
<212> TYPE: RNA
<213> ORGANISM: Artificial Sequence
<220> FEATURE:
<223> OTHER INFORMATION: synthetic microRNA mimic mmu-miR-297a

<400> SEQUENCE: 120
auguaugugu gcaugugcau gu                                               22

<210> SEQ ID NO 121
<211> LENGTH: 23
<212> TYPE: RNA
<213> ORGANISM: Artificial Sequence
<220> FEATURE:
<223> OTHER INFORMATION: synthetic microRNA mimic mmu-miR-344

<400> SEQUENCE: 121
ugaucuagcc aaagccugac ugu                                              23

<210> SEQ ID NO 122
<211> LENGTH: 23
<212> TYPE: RNA
<213> ORGANISM: Artificial Sequence
<220> FEATURE:
<223> OTHER INFORMATION: synthetic microRNA mimic mmu-miR-18

<400> SEQUENCE: 122
uaaggugcau cuagugcaga uag                                              23

<210> SEQ ID NO 123
<211> LENGTH: 22
```

```
<212> TYPE: RNA
<213> ORGANISM: Artificial Sequence
<220> FEATURE:
<223> OTHER INFORMATION: synthetic microRNA mimic mmu-miR-93*

<400> SEQUENCE: 123
acugcugagc uagcacuucc cg                                                22

<210> SEQ ID NO 124
<211> LENGTH: 22
<212> TYPE: RNA
<213> ORGANISM: Artificial Sequence
<220> FEATURE:
<223> OTHER INFORMATION: synthetic microRNA mimic mmu-miR-297

<400> SEQUENCE: 124
auguaugugu gcaugugcau gu                                                22

<210> SEQ ID NO 125
<211> LENGTH: 22
<212> TYPE: RNA
<213> ORGANISM: Artificial Sequence
<220> FEATURE:
<223> OTHER INFORMATION: synthetic microRNA mimic mmu-miR-16

<400> SEQUENCE: 125
uagcagcacg uaaauauugg cg                                                22

<210> SEQ ID NO 126
<211> LENGTH: 22
<212> TYPE: RNA
<213> ORGANISM: Artificial Sequence
<220> FEATURE:
<223> OTHER INFORMATION: synthetic microRNA mimic mmu-miR-380-5p

<400> SEQUENCE: 126
augguugacc auagaacaug cg                                                22

<210> SEQ ID NO 127
<211> LENGTH: 23
<212> TYPE: RNA
<213> ORGANISM: Artificial Sequence
<220> FEATURE:
<223> OTHER INFORMATION: synthetic microRNA mimic mmu-miR-672

<400> SEQUENCE: 127
ugagguuggu guacugugug uga                                               23

<210> SEQ ID NO 128
<211> LENGTH: 21
<212> TYPE: RNA
<213> ORGANISM: Artificial Sequence
<220> FEATURE:
<223> OTHER INFORMATION: synthetic microRNA mimic mmu-miR-431

<400> SEQUENCE: 128
ugucuugcag gccgucaugc a                                                 21

<210> SEQ ID NO 129
<211> LENGTH: 21
<212> TYPE: RNA
<213> ORGANISM: Artificial Sequence
<220> FEATURE:
<223> OTHER INFORMATION: synthetic microRNA mimic mmu-miR-715

<400> SEQUENCE: 129
```

```
cuccgugcac accccccgcgu g                                          21

<210> SEQ ID NO 130
<211> LENGTH: 22
<212> TYPE: RNA
<213> ORGANISM: Artificial Sequence
<220> FEATURE:
<223> OTHER INFORMATION: synthetic microRNA mimic mmu-miR-669a

<400> SEQUENCE: 130
aguugugugu gcauguucau gu                                          22

<210> SEQ ID NO 131
<211> LENGTH: 23
<212> TYPE: RNA
<213> ORGANISM: Artificial Sequence
<220> FEATURE:
<223> OTHER INFORMATION: synthetic microRNA mimic mmu-miR-103

<400> SEQUENCE: 131
agcagcauug uacagggcua uga                                         23

<210> SEQ ID NO 132
<211> LENGTH: 22
<212> TYPE: RNA
<213> ORGANISM: Artificial Sequence
<220> FEATURE:
<223> OTHER INFORMATION: synthetic microRNA mimic mmu-miR-124*

<400> SEQUENCE: 132
cguguucaca gcggaccuug au                                          22

<210> SEQ ID NO 133
<211> LENGTH: 22
<212> TYPE: RNA
<213> ORGANISM: Artificial Sequence
<220> FEATURE:
<223> OTHER INFORMATION: synthetic microRNA mimic mmu-miR-15b

<400> SEQUENCE: 133
uagcagcaca ucaugguuua ca                                          22

<210> SEQ ID NO 134
<211> LENGTH: 22
<212> TYPE: RNA
<213> ORGANISM: Artificial Sequence
<220> FEATURE:
<223> OTHER INFORMATION: synthetic microRNA mimic mmu-miR-450b*

<400> SEQUENCE: 134
auugggaaca uuuugcaugc au                                          22

<210> SEQ ID NO 135
<211> LENGTH: 22
<212> TYPE: RNA
<213> ORGANISM: Artificial Sequence
<220> FEATURE:
<223> OTHER INFORMATION: synthetic microRNA mimic mmu-miR-882

<400> SEQUENCE: 135
aggagagagu uagcgcauua gu                                          22

<210> SEQ ID NO 136
<211> LENGTH: 22
<212> TYPE: RNA
<213> ORGANISM: Artificial Sequence
```

```
<220> FEATURE:
<223> OTHER INFORMATION: synthetic microRNA mimic mmu-miR-686

<400> SEQUENCE: 136
auugcuuccc agacggugaa ga                                              22

<210> SEQ ID NO 137
<211> LENGTH: 21
<212> TYPE: RNA
<213> ORGANISM: Artificial Sequence
<220> FEATURE:
<223> OTHER INFORMATION: synthetic microRNA mimic mmu-miR-222

<400> SEQUENCE: 137
agcuacaucu ggcuacuggg u                                               21

<210> SEQ ID NO 138
<211> LENGTH: 19
<212> TYPE: RNA
<213> ORGANISM: Artificial Sequence
<220> FEATURE:
<223> OTHER INFORMATION: synthetic microRNA mimic mmu-miR-684

<400> SEQUENCE: 138
aguuuucccu ucaagucaa                                                  19

<210> SEQ ID NO 139
<211> LENGTH: 22
<212> TYPE: RNA
<213> ORGANISM: Artificial Sequence
<220> FEATURE:
<223> OTHER INFORMATION: synthetic microRNA mimic mmu-miR-450b

<400> SEQUENCE: 139
uuuugcagua uguuccugaa ua                                              22

<210> SEQ ID NO 140
<211> LENGTH: 22
<212> TYPE: RNA
<213> ORGANISM: Artificial Sequence
<220> FEATURE:
<223> OTHER INFORMATION: synthetic microRNA mimic mmu-miR-582-3p

<400> SEQUENCE: 140
ccuguugaac aacugaaccc aa                                              22

<210> SEQ ID NO 141
<211> LENGTH: 23
<212> TYPE: RNA
<213> ORGANISM: Artificial Sequence
<220> FEATURE:
<223> OTHER INFORMATION: synthetic microRNA mimic mmu-miR-135b

<400> SEQUENCE: 141
uauggcuuuu cauuccuaug uga                                             23

<210> SEQ ID NO 142
<211> LENGTH: 23
<212> TYPE: RNA
<213> ORGANISM: Artificial Sequence
<220> FEATURE:
<223> OTHER INFORMATION: synthetic microRNA mimic mmu-miR-493

<400> SEQUENCE: 142
ugaagguccu acugugugcc agg                                             23
```

```
<210> SEQ ID NO 143
<211> LENGTH: 16
<212> TYPE: RNA
<213> ORGANISM: Artificial Sequence
<220> FEATURE:
<223> OTHER INFORMATION: synthetic microRNA mimic mmu-miR-546

<400> SEQUENCE: 143
augguggcac ggaguc                                                     16

<210> SEQ ID NO 144
<211> LENGTH: 23
<212> TYPE: RNA
<213> ORGANISM: Artificial Sequence
<220> FEATURE:
<223> OTHER INFORMATION: synthetic microRNA mimic mmu-miR-708

<400> SEQUENCE: 144
aaggagcuua caaucuagcu ggg                                             23

<210> SEQ ID NO 145
<211> LENGTH: 22
<212> TYPE: RNA
<213> ORGANISM: Artificial Sequence
<220> FEATURE:
<223> OTHER INFORMATION: synthetic microRNA mimic mmu-miR-433-3p

<400> SEQUENCE: 145
aucaugaugg gcuccucggu gu                                              22

<210> SEQ ID NO 146
<211> LENGTH: 22
<212> TYPE: RNA
<213> ORGANISM: Artificial Sequence
<220> FEATURE:
<223> OTHER INFORMATION: synthetic microRNA mimic mmu-miR-494

<400> SEQUENCE: 146
ugaaacauac acgggaaacc uc                                              22

<210> SEQ ID NO 147
<211> LENGTH: 22
<212> TYPE: RNA
<213> ORGANISM: Artificial Sequence
<220> FEATURE:
<223> OTHER INFORMATION: synthetic microRNA mimic mmu-miR-203

<400> SEQUENCE: 147
gugaaauguu uaggaccacu ag                                              22

<210> SEQ ID NO 148
<211> LENGTH: 23
<212> TYPE: RNA
<213> ORGANISM: Artificial Sequence
<220> FEATURE:
<223> OTHER INFORMATION: synthetic microRNA mimic mmu-miR-9

<400> SEQUENCE: 148
ucuuugguua ucuagcugua uga                                             23

<210> SEQ ID NO 149
<211> LENGTH: 23
<212> TYPE: RNA
<213> ORGANISM: Artificial Sequence
<220> FEATURE:
<223> OTHER INFORMATION: synthetic microRNA mimic mmu-miR-574-5p
```

```
<400> SEQUENCE: 149
ugagugugug ugugugagug ugu                                        23

<210> SEQ ID NO 150
<211> LENGTH: 21
<212> TYPE: RNA
<213> ORGANISM: Artificial Sequence
<220> FEATURE:
<223> OTHER INFORMATION: synthetic microRNA mimic mmu-miR-376c

<400> SEQUENCE: 150
aacauagagg aaauuucacg u                                          21

<210> SEQ ID NO 151
<211> LENGTH: 22
<212> TYPE: RNA
<213> ORGANISM: Artificial Sequence
<220> FEATURE:
<223> OTHER INFORMATION: synthetic microRNA mimic mmu-miR-433-5p

<400> SEQUENCE: 151
uacggugagc cugucauuau uc                                         22

<210> SEQ ID NO 152
<211> LENGTH: 22
<212> TYPE: RNA
<213> ORGANISM: Artificial Sequence
<220> FEATURE:
<223> OTHER INFORMATION: synthetic microRNA mimic mmu-miR-181a-2*

<400> SEQUENCE: 152
accgaccguu gacuguaccu ug                                         22

<210> SEQ ID NO 153
<211> LENGTH: 22
<212> TYPE: RNA
<213> ORGANISM: Artificial Sequence
<220> FEATURE:
<223> OTHER INFORMATION: synthetic microRNA mimic mmu-miR-218-2*

<400> SEQUENCE: 153 cagguucug ucaagcaccg cg                                          22

<210> SEQ ID NO 154
<211> LENGTH: 22
<212> TYPE: RNA
<213> ORGANISM: Artificial Sequence
<220> FEATURE:
<223> OTHER INFORMATION: synthetic microRNA mimic mmu-miR-196a

<400> SEQUENCE: 154
uagguaguuu caguuguug gg                                          22

<210> SEQ ID NO 155
<211> LENGTH: 22
<212> TYPE: RNA
<213> ORGANISM: Artificial Sequence
<220> FEATURE:
<223> OTHER INFORMATION: synthetic microRNA mimic mmu-miR-542-5p

<400> SEQUENCE: 155
cucggggauc aucaugucac ga                                         22

<210> SEQ ID NO 156
```

```
<211> LENGTH: 23
<212> TYPE: RNA
<213> ORGANISM: Artificial Sequence
<220> FEATURE:
<223> OTHER INFORMATION: synthetic microRNA mimic mmu-miR-7

<400> SEQUENCE: 156
uggaagacua gugauuugu ugu                                               23

<210> SEQ ID NO 157
<211> LENGTH: 21
<212> TYPE: RNA
<213> ORGANISM: Artificial Sequence
<220> FEATURE:
<223> OTHER INFORMATION: synthetic microRNA mimic mmu-miR-743b-5p

<400> SEQUENCE: 157
uguucagacu ggguguccauc a                                               21

<210> SEQ ID NO 158
<211> LENGTH: 22
<212> TYPE: RNA
<213> ORGANISM: Artificial Sequence
<220> FEATURE:
<223> OTHER INFORMATION: synthetic microRNA mimic mmu-miR-377

<400> SEQUENCE: 158
aucacacaaa ggcaacuuuu gu                                               22

<210> SEQ ID NO 159
<211> LENGTH: 21
<212> TYPE: RNA
<213> ORGANISM: Artificial Sequence
<220> FEATURE:
<223> OTHER INFORMATION: synthetic microRNA mimic mmu-miR-683

<400> SEQUENCE: 159
ccugcuguaa gcuguguccu c                                                21

<210> SEQ ID NO 160
<211> LENGTH: 22
<212> TYPE: RNA
<213> ORGANISM: Artificial Sequence
<220> FEATURE:
<223> OTHER INFORMATION: synthetic microRNA mimic mmu-miR-675-5p

<400> SEQUENCE: 160
uggugcggaa agggcccaca gu                                               22

<210> SEQ ID NO 161
<211> LENGTH: 22
<212> TYPE: RNA
<213> ORGANISM: Artificial Sequence
<220> FEATURE:
<223> OTHER INFORMATION: synthetic microRNA mimic mmu-miR-598

<400> SEQUENCE: 161
uacgucaucg ucgucaucgu ua                                               22

<210> SEQ ID NO 162
<211> LENGTH: 22
<212> TYPE: RNA
<213> ORGANISM: Artificial Sequence
<220> FEATURE:
<223> OTHER INFORMATION: synthetic microRNA mimic mmu-miR-15b*

<400> SEQUENCE: 162
```
cgaaucauua uuugcugcuc ua                                          22

<210> SEQ ID NO 163
<211> LENGTH: 23
<212> TYPE: RNA
<213> ORGANISM: Artificial Sequence
<220> FEATURE:
<223> OTHER INFORMATION: synthetic microRNA mimic mmu-miR-9

<400> SEQUENCE: 163
ucuuugguua ucuagcugua uga                                         23

<210> SEQ ID NO 164
<211> LENGTH: 22
<212> TYPE: RNA
<213> ORGANISM: Artificial Sequence
<220> FEATURE:
<223> OTHER INFORMATION: synthetic microRNA mimic mmu-miR-450a-3p

<400> SEQUENCE: 164
auuggggaug cuuugcauuc au                                          22

<210> SEQ ID NO 165
<211> LENGTH: 20
<212> TYPE: RNA
<213> ORGANISM: Artificial Sequence
<220> FEATURE:
<223> OTHER INFORMATION: synthetic microRNA mimic mmu-miR-449b

<400> SEQUENCE: 165
aggcaguguu guuagcuggc                                             20

<210> SEQ ID NO 166
<211> LENGTH: 21
<212> TYPE: RNA
<213> ORGANISM: Artificial Sequence
<220> FEATURE:
<223> OTHER INFORMATION: synthetic microRNA mimic mmu-miR-707

<400> SEQUENCE: 166
cagucaugcc gcuugccuac g                                           21

<210> SEQ ID NO 167
<211> LENGTH: 22
<212> TYPE: RNA
<213> ORGANISM: Artificial Sequence
<220> FEATURE:
<223> OTHER INFORMATION: synthetic microRNA mimic mmu-miR-335-3p

<400> SEQUENCE: 167
uuuuucauua uugcuccuga cc                                          22

<210> SEQ ID NO 168
<211> LENGTH: 22
<212> TYPE: RNA
<213> ORGANISM: Artificial Sequence
<220> FEATURE:
<223> OTHER INFORMATION: synthetic microRNA mimic mmu-miR-147

<400> SEQUENCE: 168
gugugcggaa augcuucugc ua                                          22

<210> SEQ ID NO 169
<211> LENGTH: 22
<212> TYPE: RNA

```
<213> ORGANISM: Artificial Sequence
<220> FEATURE:
<223> OTHER INFORMATION: synthetic microRNA mimic mmu-miR-466c-5p

<400> SEQUENCE: 169
gaugugugug ugcauguaca ua                                              22

<210> SEQ ID NO 170
<211> LENGTH: 22
<212> TYPE: RNA
<213> ORGANISM: Artificial Sequence
<220> FEATURE:
<223> OTHER INFORMATION: synthetic microRNA mimic mmu-miR-16

<400> SEQUENCE: 170
uagcagcacg uaaauauugg cg                                              22

<210> SEQ ID NO 171
<211> LENGTH: 22
<212> TYPE: RNA
<213> ORGANISM: Artificial Sequence
<220> FEATURE:
<223> OTHER INFORMATION: synthetic microRNA mimic mmu-miR-127

<400> SEQUENCE: 171
ucggauccgu cugagcuugg cu                                              22

<210> SEQ ID NO 172
<211> LENGTH: 23
<212> TYPE: RNA
<213> ORGANISM: Artificial Sequence
<220> FEATURE:
<223> OTHER INFORMATION: synthetic microRNA mimic mmu-miR-673-3p

<400> SEQUENCE: 172
uccggggcug aguucugugc acc                                             23

<210> SEQ ID NO 173
<211> LENGTH: 22
<212> TYPE: RNA
<213> ORGANISM: Artificial Sequence
<220> FEATURE:
<223> OTHER INFORMATION: synthetic microRNA mimic mmu-miR-466b-5p

<400> SEQUENCE: 173
gaugugugug uacauguaca ug                                              22

<210> SEQ ID NO 174
<211> LENGTH: 22
<212> TYPE: RNA
<213> ORGANISM: Artificial Sequence
<220> FEATURE:
<223> OTHER INFORMATION: synthetic microRNA mimic mmu-miR-27a*

<400> SEQUENCE: 174
agggcuuagc ugcuugugag ca                                              22

<210> SEQ ID NO 175
<211> LENGTH: 22
<212> TYPE: RNA
<213> ORGANISM: Artificial Sequence
<220> FEATURE:
<223> OTHER INFORMATION: synthetic microRNA mimic mmu-miR-1

<400> SEQUENCE: 175
uggaauguaa agaaguaugu au                                              22
```

-continued

<210> SEQ ID NO 176
<211> LENGTH: 22
<212> TYPE: RNA
<213> ORGANISM: Artificial Sequence
<220> FEATURE:
<223> OTHER INFORMATION: synthetic microRNA mimic mmu-miR-201

<400> SEQUENCE: 176
uacucaguaa ggcauuguuc uu                                              22

<210> SEQ ID NO 177
<211> LENGTH: 21
<212> TYPE: RNA
<213> ORGANISM: Artificial Sequence
<220> FEATURE:
<223> OTHER INFORMATION: synthetic microRNA mimic mmu-miR-376b

<400> SEQUENCE: 177
aucauagagg aacauccacu u                                               21

<210> SEQ ID NO 178
<211> LENGTH: 22
<212> TYPE: RNA
<213> ORGANISM: Artificial Sequence
<220> FEATURE:
<223> OTHER INFORMATION: synthetic microRNA mimic mmu-miR-187

<400> SEQUENCE: 178
ucgugucuug uguugcagcc gg                                              22

<210> SEQ ID NO 179
<211> LENGTH: 22
<212> TYPE: RNA
<213> ORGANISM: Artificial Sequence
<220> FEATURE:
<223> OTHER INFORMATION: synthetic microRNA mimic mmu-miR-299

<400> SEQUENCE: 179
ugguuuaccg ucccacauac au                                              22

<210> SEQ ID NO 180
<211> LENGTH: 22
<212> TYPE: RNA
<213> ORGANISM: Artificial Sequence
<220> FEATURE:
<223> OTHER INFORMATION: synthetic microRNA mimic mmu-miR-299

<400> SEQUENCE: 180
uaugugggac gguaaaccgc uu                                              22

<210> SEQ ID NO 181
<211> LENGTH: 22
<212> TYPE: RNA
<213> ORGANISM: Artificial Sequence
<220> FEATURE:
<223> OTHER INFORMATION: synthetic microRNA mimic mmu-miR-574-3p

<400> SEQUENCE: 181
cacgcucaug cacacaccca ca                                              22

<210> SEQ ID NO 182
<211> LENGTH: 22
<212> TYPE: RNA
<213> ORGANISM: Artificial Sequence
<220> FEATURE:

<223> OTHER INFORMATION: synthetic microRNA mimic mmu-miR-193*

<400> SEQUENCE: 182
ugggucuuug cgggcaagau ga                                    22

<210> SEQ ID NO 183
<211> LENGTH: 22
<212> TYPE: RNA
<213> ORGANISM: Artificial Sequence
<220> FEATURE:
<223> OTHER INFORMATION: synthetic microRNA mimic mmu-miR-679

<400> SEQUENCE: 183
ggacugugag gugacucuug gu                                    22

<210> SEQ ID NO 184
<211> LENGTH: 23
<212> TYPE: RNA
<213> ORGANISM: Artificial Sequence
<220> FEATURE:
<223> OTHER INFORMATION: synthetic microRNA mimic mmu-miR-540-5p

<400> SEQUENCE: 184
caagggucac ccucugacuc ugu                                   23

<210> SEQ ID NO 185
<211> LENGTH: 22
<212> TYPE: RNA
<213> ORGANISM: Artificial Sequence
<220> FEATURE:
<223> OTHER INFORMATION: synthetic microRNA mimic mmu-miR-466a-5p

<400> SEQUENCE: 185
uaugugugug uacauguaca ua                                    22

<210> SEQ ID NO 186
<211> LENGTH: 23
<212> TYPE: RNA
<213> ORGANISM: Artificial Sequence
<220> FEATURE:
<223> OTHER INFORMATION: synthetic microRNA mimic mmu-miR-470

<400> SEQUENCE: 186
uucuuggacu ggcacuggug agu                                   23

<210> SEQ ID NO 187
<211> LENGTH: 21
<212> TYPE: RNA
<213> ORGANISM: Artificial Sequence
<220> FEATURE:
<223> OTHER INFORMATION: synthetic microRNA mimic mmu-miR-1224

<400> SEQUENCE: 187
gugaggacug gggaggugga g                                     21

<210> SEQ ID NO 188
<211> LENGTH: 23
<212> TYPE: RNA
<213> ORGANISM: Artificial Sequence
<220> FEATURE:
<223> OTHER INFORMATION: synthetic microRNA mimic mmu-miR-191

<400> SEQUENCE: 188
caacggaauc ccaaaagcag cug                                   23

```
<210> SEQ ID NO 189
<211> LENGTH: 23
<212> TYPE: RNA
<213> ORGANISM: Artificial Sequence
<220> FEATURE:
<223> OTHER INFORMATION: synthetic miRNA hsa-miR-199b-5p

<400> SEQUENCE: 189
cccaguguuu agacuaucug uuc                                               23

<210> SEQ ID NO 190
<211> LENGTH: 22
<212> TYPE: RNA
<213> ORGANISM: Artificial Sequence
<220> FEATURE:
<223> OTHER INFORMATION: synthetic miRNA hsa-let-7a

<400> SEQUENCE: 190
ugagguagua gguuguauag uu                                                22

<210> SEQ ID NO 191
<211> LENGTH: 22
<212> TYPE: RNA
<213> ORGANISM: Artificial Sequence
<220> FEATURE:
<223> OTHER INFORMATION: synthetic miRNA hsa-let-7b

<400> SEQUENCE: 191
ugagguagua gguugugugg uu                                                22

<210> SEQ ID NO 192
<211> LENGTH: 22
<212> TYPE: RNA
<213> ORGANISM: Artificial Sequence
<220> FEATURE:
<223> OTHER INFORMATION: synthetic miRNA hsa-let-7c

<400> SEQUENCE: 192
ugagguagua gguuguaugg uu                                                22

<210> SEQ ID NO 193
<211> LENGTH: 22
<212> TYPE: RNA
<213> ORGANISM: Artificial Sequence
<220> FEATURE:
<223> OTHER INFORMATION: synthetic miRNA hsa-let-7d

<400> SEQUENCE: 193
agagguagua gguugcauag uu                                                22

<210> SEQ ID NO 194
<211> LENGTH: 22
<212> TYPE: RNA
<213> ORGANISM: Artificial Sequence
<220> FEATURE:
<223> OTHER INFORMATION: synthetic miRNA hsa-let-7e

<400> SEQUENCE: 194
ugagguagga gguuguauag uu                                                22

<210> SEQ ID NO 195
<211> LENGTH: 22
<212> TYPE: RNA
<213> ORGANISM: Artificial Sequence
<220> FEATURE:
<223> OTHER INFORMATION: synthetic miRNA hsa-let-7f
```

<400> SEQUENCE: 195
ugagguagua gauuguauag uu					22

<210> SEQ ID NO 196
<211> LENGTH: 22
<212> TYPE: RNA
<213> ORGANISM: Artificial Sequence
<220> FEATURE:
<223> OTHER INFORMATION: synthetic miRNA hsa-let-7g

<400> SEQUENCE: 196
ugagguagua guuuguacag uu					22

<210> SEQ ID NO 197
<211> LENGTH: 22
<212> TYPE: RNA
<213> ORGANISM: Artificial Sequence
<220> FEATURE:
<223> OTHER INFORMATION: synthetic miRNA hsa-let-7i

<400> SEQUENCE: 197
ugagguagua guuugugcug uu					22

<210> SEQ ID NO 198
<211> LENGTH: 22
<212> TYPE: RNA
<213> ORGANISM: Artificial Sequence
<220> FEATURE:
<223> OTHER INFORMATION: synthetic miRNA hsa-miR-100

<400> SEQUENCE: 198
aacccguaga uccgaacuug ug					22

<210> SEQ ID NO 199
<211> LENGTH: 22
<212> TYPE: RNA
<213> ORGANISM: Artificial Sequence
<220> FEATURE:
<223> OTHER INFORMATION: synthetic miRNA hsa-miR-100

<400> SEQUENCE: 199
aacccguaga uccgaacuug ug					22

<210> SEQ ID NO 200
<211> LENGTH: 22
<212> TYPE: RNA
<213> ORGANISM: Artificial Sequence
<220> FEATURE:
<223> OTHER INFORMATION: synthetic miRNA hsa-miR-122

<400> SEQUENCE: 200
uggaguguga caaugguguu ug					22

<210> SEQ ID NO 201
<211> LENGTH: 22
<212> TYPE: RNA
<213> ORGANISM: Artificial Sequence
<220> FEATURE:
<223> OTHER INFORMATION: synthetic miRNA hsa-miR-127-3p

<400> SEQUENCE: 201
ucggauccgu cugagcuugg cu					22

<210> SEQ ID NO 202
<211> LENGTH: 21

```
<212> TYPE: RNA
<213> ORGANISM: Artificial Sequence
<220> FEATURE:
<223> OTHER INFORMATION: synthetic miRNA hsa-miR-128

<400> SEQUENCE: 202
ucacagugaa ccggucucuu u                                              21

<210> SEQ ID NO 203
<211> LENGTH: 21
<212> TYPE: RNA
<213> ORGANISM: Artificial Sequence
<220> FEATURE:
<223> OTHER INFORMATION: synthetic miRNA hsa-miR-129-5p

<400> SEQUENCE: 203
cuuuuugcgg ucugggcuug c                                              21

<210> SEQ ID NO 204
<211> LENGTH: 22
<212> TYPE: RNA
<213> ORGANISM: Artificial Sequence
<220> FEATURE:
<223> OTHER INFORMATION: synthetic miRNA hsa-miR-134

<400> SEQUENCE: 204
ugugacuggu ugaccagagg gg                                             22

<210> SEQ ID NO 205
<211> LENGTH: 22
<212> TYPE: RNA
<213> ORGANISM: Artificial Sequence
<220> FEATURE:
<223> OTHER INFORMATION: synthetic miRNA hsa-miR-140-5p

<400> SEQUENCE: 205
cagugguuuu acccuauggu ag                                             22

<210> SEQ ID NO 206
<211> LENGTH: 23
<212> TYPE: RNA
<213> ORGANISM: Artificial Sequence
<220> FEATURE:
<223> OTHER INFORMATION: synthetic miRNA hsa-miR-145

<400> SEQUENCE: 206
guccaguuuu cccaggaauc ccu                                            23

<210> SEQ ID NO 207
<211> LENGTH: 23
<212> TYPE: RNA
<213> ORGANISM: Artificial Sequence
<220> FEATURE:
<223> OTHER INFORMATION: synthetic miRNA hsa-miR-149

<400> SEQUENCE: 207
ucuggcuccg ugucuucacu ccc                                            23

<210> SEQ ID NO 208
<211> LENGTH: 23
<212> TYPE: RNA
<213> ORGANISM: Artificial Sequence
<220> FEATURE:
<223> OTHER INFORMATION: synthetic miRNA hsa-miR-18a

<400> SEQUENCE: 208
```
uaaggugcau cuagugcaga uag                                          23

<210> SEQ ID NO 209
<211> LENGTH: 23
<212> TYPE: RNA
<213> ORGANISM: Artificial Sequence
<220> FEATURE:
<223> OTHER INFORMATION: synthetic miRNA hsa-miR-18b

<400> SEQUENCE: 209
uaaggugcau cuagugcagu uag                                          23

<210> SEQ ID NO 210
<211> LENGTH: 22
<212> TYPE: RNA
<213> ORGANISM: Artificial Sequence
<220> FEATURE:
<223> OTHER INFORMATION: synthetic miRNA hsa-miR-193a-3p

<400> SEQUENCE: 210
aacuggccua caaaguccca gu                                           22

<210> SEQ ID NO 211
<211> LENGTH: 23
<212> TYPE: RNA
<213> ORGANISM: Artificial Sequence
<220> FEATURE:
<223> OTHER INFORMATION: synthetic miRNA hsa-miR-199a-5p

<400> SEQUENCE: 211
cccaguguuc agacuaccug uuc                                          23

<210> SEQ ID NO 212
<211> LENGTH: 22
<212> TYPE: RNA
<213> ORGANISM: Artificial Sequence
<220> FEATURE:
<223> OTHER INFORMATION: synthetic miRNA hsa-miR-216a

<400> SEQUENCE: 212
uaaucucagc uggcaacugu ga                                           22

<210> SEQ ID NO 213
<211> LENGTH: 22
<212> TYPE: RNA
<213> ORGANISM: Artificial Sequence
<220> FEATURE:
<223> OTHER INFORMATION: synthetic miRNA hsa-miR-216b

<400> SEQUENCE: 213
aaaucucugc aggcaaaugu ga                                           22

<210> SEQ ID NO 214
<211> LENGTH: 21
<212> TYPE: RNA
<213> ORGANISM: Artificial Sequence
<220> FEATURE:
<223> OTHER INFORMATION: synthetic miRNA hsa-miR-218

<400> SEQUENCE: 214
uugugcuuga ucuaaccaug u                                            21

<210> SEQ ID NO 215
<211> LENGTH: 22
<212> TYPE: RNA
<213> ORGANISM: Artificial Sequence

```
<220> FEATURE:
<223> OTHER INFORMATION: synthetic miRNA hsa-miR-26a

<400> SEQUENCE: 215
uucaaguaau ccaggauagg cu                                              22

<210> SEQ ID NO 216
<211> LENGTH: 21
<212> TYPE: RNA
<213> ORGANISM: Artificial Sequence
<220> FEATURE:
<223> OTHER INFORMATION: synthetic miRNA hsa-miR-31

<400> SEQUENCE: 216
aggcaagaug cuggcauagc u                                               21

<210> SEQ ID NO 217
<211> LENGTH: 22
<212> TYPE: RNA
<213> ORGANISM: Artificial Sequence
<220> FEATURE:
<223> OTHER INFORMATION: synthetic miRNA hsa-miR-345

<400> SEQUENCE: 217
gcugacuccu aguccagggc uc                                              22

<210> SEQ ID NO 218
<211> LENGTH: 23
<212> TYPE: RNA
<213> ORGANISM: Artificial Sequence
<220> FEATURE:
<223> OTHER INFORMATION: synthetic miRNA hsa-miR-34c-5p

<400> SEQUENCE: 218
aggcagugua guuagcugau ugc                                             23

<210> SEQ ID NO 219
<211> LENGTH: 24
<212> TYPE: RNA
<213> ORGANISM: Artificial Sequence
<220> FEATURE:
<223> OTHER INFORMATION: synthetic miRNA hsa-miR-362-5p

<400> SEQUENCE: 219
aauccuugga accaggugu gagu                                             24

<210> SEQ ID NO 220
<211> LENGTH: 21
<212> TYPE: RNA
<213> ORGANISM: Artificial Sequence
<220> FEATURE:
<223> OTHER INFORMATION: synthetic miRNA hsa-miR-378

<400> SEQUENCE: 220
acuggacuug gagucagaag g                                               21

<210> SEQ ID NO 221
<211> LENGTH: 20
<212> TYPE: RNA
<213> ORGANISM: Artificial Sequence
<220> FEATURE:
<223> OTHER INFORMATION: synthetic miRNA hsa-miR-384

<400> SEQUENCE: 221
auuccuagaa auuguucaua                                                 20
```

```
<210> SEQ ID NO 222
<211> LENGTH: 22
<212> TYPE: RNA
<213> ORGANISM: Artificial Sequence
<220> FEATURE:
<223> OTHER INFORMATION: synthetic miRNA hsa-miR-409-3p

<400> SEQUENCE: 222
gaauguugcu cggugaaccc cu                                              22

<210> SEQ ID NO 223
<211> LENGTH: 22
<212> TYPE: RNA
<213> ORGANISM: Artificial Sequence
<220> FEATURE:
<223> OTHER INFORMATION: synthetic miRNA hsa-miR-450a

<400> SEQUENCE: 223
uuuugcgaug uguccuaau au                                               22

<210> SEQ ID NO 224
<211> LENGTH: 22
<212> TYPE: RNA
<213> ORGANISM: Artificial Sequence
<220> FEATURE:
<223> OTHER INFORMATION: synthetic miRNA hsa-miR-450b-5p

<400> SEQUENCE: 224
uuuugcaaua uguccugaa ua                                               22

<210> SEQ ID NO 225
<211> LENGTH: 22
<212> TYPE: RNA
<213> ORGANISM: Artificial Sequence
<220> FEATURE:
<223> OTHER INFORMATION: synthetic miRNA hsa-miR-452

<400> SEQUENCE: 225
aacuguuugc agaggaaacu ga                                              22

<210> SEQ ID NO 226
<211> LENGTH: 22
<212> TYPE: RNA
<213> ORGANISM: Artificial Sequence
<220> FEATURE:
<223> OTHER INFORMATION: synthetic miRNA hsa-miR-98

<400> SEQUENCE: 226
ugagguagua aguuguauug uu                                              22

<210> SEQ ID NO 227
<211> LENGTH: 22
<212> TYPE: RNA
<213> ORGANISM: Artificial Sequence
<220> FEATURE:
<223> OTHER INFORMATION: synthetic miRNA hsa-miR-99a

<400> SEQUENCE: 227
aacccguaga uccgaucuug ug                                              22

<210> SEQ ID NO 228
<211> LENGTH: 22
<212> TYPE: RNA
<213> ORGANISM: Artificial Sequence
<220> FEATURE:
<223> OTHER INFORMATION: synthetic miRNA hsa-miR-99b
```

```
<400> SEQUENCE: 228
cacccguaga accgaccuug cg                                                    22

<210> SEQ ID NO 229
<211> LENGTH: 22
<212> TYPE: RNA
<213> ORGANISM: Artificial Sequence
<220> FEATURE:
<223> OTHER INFORMATION: synthetic miRNA mmu-let-7a

<400> SEQUENCE: 229
ugagguagua gguuguauag uu                                                    22

<210> SEQ ID NO 230
<211> LENGTH: 22
<212> TYPE: RNA
<213> ORGANISM: Artificial Sequence
<220> FEATURE:
<223> OTHER INFORMATION: synthetic miRNA mmu-let-7b

<400> SEQUENCE: 230
ugagguagua gguugugugg uu                                                    22

<210> SEQ ID NO 231
<211> LENGTH: 22
<212> TYPE: RNA
<213> ORGANISM: Artificial Sequence
<220> FEATURE:
<223> OTHER INFORMATION: synthetic miRNA mmu-let-7c

<400> SEQUENCE: 231
ugagguagua gguuguaugg uu                                                    22

<210> SEQ ID NO 232
<211> LENGTH: 22
<212> TYPE: RNA
<213> ORGANISM: Artificial Sequence
<220> FEATURE:
<223> OTHER INFORMATION: synthetic miRNA mmu-let-7d

<400> SEQUENCE: 232
agagguagua gguugcauag uu                                                    22

<210> SEQ ID NO 233
<211> LENGTH: 22
<212> TYPE: RNA
<213> ORGANISM: Artificial Sequence
<220> FEATURE:
<223> OTHER INFORMATION: synthetic miRNA mmu-let-7e

<400> SEQUENCE: 233
ugagguagga gguuguauag uu                                                    22

<210> SEQ ID NO 234
<211> LENGTH: 22
<212> TYPE: RNA
<213> ORGANISM: Artificial Sequence
<220> FEATURE:
<223> OTHER INFORMATION: synthetic miRNA mmu-let-7f

<400> SEQUENCE: 234
ugagguagua gauuguauag uu                                                    22

<210> SEQ ID NO 235
```

```
<211> LENGTH: 22
<212> TYPE: RNA
<213> ORGANISM: Artificial Sequence
<220> FEATURE:
<223> OTHER INFORMATION: synthetic miRNA mmu-let-7g

<400> SEQUENCE: 235
ugagguagua guuuguacag uu                                              22

<210> SEQ ID NO 236
<211> LENGTH: 22
<212> TYPE: RNA
<213> ORGANISM: Artificial Sequence
<220> FEATURE:
<223> OTHER INFORMATION: synthetic miRNA mmu-let-7i

<400> SEQUENCE: 236
ugagguagua guuugugcug uu                                              22

<210> SEQ ID NO 237
<211> LENGTH: 22
<212> TYPE: RNA
<213> ORGANISM: Artificial Sequence
<220> FEATURE:
<223> OTHER INFORMATION: synthetic miRNA mmu-miR-100

<400> SEQUENCE: 237
aacccguaga uccgaacuug ug                                              22

<210> SEQ ID NO 238
<211> LENGTH: 22
<212> TYPE: RNA
<213> ORGANISM: Artificial Sequence
<220> FEATURE:
<223> OTHER INFORMATION: synthetic miRNA mmu-miR-100

<400> SEQUENCE: 238
aacccguaga uccgaacuug ug                                              22

<210> SEQ ID NO 239
<211> LENGTH: 22
<212> TYPE: RNA
<213> ORGANISM: Artificial Sequence
<220> FEATURE:
<223> OTHER INFORMATION: synthetic miRNA mmu-miR-122

<400> SEQUENCE: 239
uggaguguga caaugguguu ug                                              22

<210> SEQ ID NO 240
<211> LENGTH: 22
<212> TYPE: RNA
<213> ORGANISM: Artificial Sequence
<220> FEATURE:
<223> OTHER INFORMATION: synthetic miRNA mmu-miR-127

<400> SEQUENCE: 240
ucggauccgu cugagcuugg cu                                              22

<210> SEQ ID NO 241
<211> LENGTH: 21
<212> TYPE: RNA
<213> ORGANISM: Artificial Sequence
<220> FEATURE:
<223> OTHER INFORMATION: synthetic miRNA mmu-miR-128

<400> SEQUENCE: 241
```

```
ucacagugaa ccggucucuu u                                              21

<210> SEQ ID NO 242
<211> LENGTH: 21
<212> TYPE: RNA
<213> ORGANISM: Artificial Sequence
<220> FEATURE:
<223> OTHER INFORMATION: synthetic miRNA mmu-miR-129-5p

<400> SEQUENCE: 242
cuuuuugcgg ucugggcuug c                                              21

<210> SEQ ID NO 243
<211> LENGTH: 22
<212> TYPE: RNA
<213> ORGANISM: Artificial Sequence
<220> FEATURE:
<223> OTHER INFORMATION: synthetic miRNA mmu-miR-134

<400> SEQUENCE: 243
ugugacuggu ugaccagagg gg                                             22

<210> SEQ ID NO 244
<211> LENGTH: 22
<212> TYPE: RNA
<213> ORGANISM: Artificial Sequence
<220> FEATURE:
<223> OTHER INFORMATION: synthetic miRNA mmu-miR-140

<400> SEQUENCE: 244
cagugguuuu acccuauggu ag                                             22

<210> SEQ ID NO 245
<211> LENGTH: 23
<212> TYPE: RNA
<213> ORGANISM: Artificial Sequence
<220> FEATURE:
<223> OTHER INFORMATION: synthetic miRNA mmu-miR-145

<400> SEQUENCE: 245
guccaguuuu cccaggaauc ccu                                            23

<210> SEQ ID NO 246
<211> LENGTH: 23
<212> TYPE: RNA
<213> ORGANISM: Artificial Sequence
<220> FEATURE:
<223> OTHER INFORMATION: synthetic miRNA mmu-miR-149

<400> SEQUENCE: 246
ucuggcuccg ugucuucacu ccc                                            23

<210> SEQ ID NO 247
<211> LENGTH: 23
<212> TYPE: RNA
<213> ORGANISM: Artificial Sequence
<220> FEATURE:
<223> OTHER INFORMATION: synthetic miRNA mmu-miR-18a

<400> SEQUENCE: 247
uaaggugcau cuagugcaga uag                                            23

<210> SEQ ID NO 248
<211> LENGTH: 23
<212> TYPE: RNA
```

```
<213> ORGANISM: Artificial Sequence
<220> FEATURE:
<223> OTHER INFORMATION: synthetic miRNA mmu-miR-18b

<400> SEQUENCE: 248
uaaggugcau cuagugcugu uag                                              23

<210> SEQ ID NO 249
<211> LENGTH: 22
<212> TYPE: RNA
<213> ORGANISM: Artificial Sequence
<220> FEATURE:
<223> OTHER INFORMATION: synthetic miRNA mmu-miR-193

<400> SEQUENCE: 249
aacuggccua caaaguccca gu                                               22

<210> SEQ ID NO 250
<211> LENGTH: 23
<212> TYPE: RNA
<213> ORGANISM: Artificial Sequence
<220> FEATURE:
<223> OTHER INFORMATION: synthetic miRNA mmu-miR-199a-5p

<400> SEQUENCE: 250
cccaguguuc agacuaccug uuc                                              23

<210> SEQ ID NO 251
<211> LENGTH: 22
<212> TYPE: RNA
<213> ORGANISM: Artificial Sequence
<220> FEATURE:
<223> OTHER INFORMATION: synthetic miRNA mmu-miR-199b

<400> SEQUENCE: 251
acaguagucu gcacauuggu ua                                               22

<210> SEQ ID NO 252
<211> LENGTH: 22
<212> TYPE: RNA
<213> ORGANISM: Artificial Sequence
<220> FEATURE:
<223> OTHER INFORMATION: synthetic miRNA mmu-miR-216a

<400> SEQUENCE: 252
uaaucucagc uggcaacugu ga                                               22

<210> SEQ ID NO 253
<211> LENGTH: 22
<212> TYPE: RNA
<213> ORGANISM: Artificial Sequence
<220> FEATURE:
<223> OTHER INFORMATION: synthetic miRNA mmu-miR-216b

<400> SEQUENCE: 253
aaaucucugc aggcaaaugu ga                                               22

<210> SEQ ID NO 254
<211> LENGTH: 21
<212> TYPE: RNA
<213> ORGANISM: Artificial Sequence
<220> FEATURE:
<223> OTHER INFORMATION: synthetic miRNA mmu-miR-218

<400> SEQUENCE: 254
uugugcuuga ucuaaccaug u                                                21
```

<210> SEQ ID NO 255
<211> LENGTH: 22
<212> TYPE: RNA
<213> ORGANISM: Artificial Sequence
<220> FEATURE:
<223> OTHER INFORMATION: synthetic miRNA mmu-miR-26a

<400> SEQUENCE: 255
uucaaguaau ccaggauagg cu                                              22

<210> SEQ ID NO 256
<211> LENGTH: 22
<212> TYPE: RNA
<213> ORGANISM: Artificial Sequence
<220> FEATURE:
<223> OTHER INFORMATION: synthetic miRNA mmu-miR-31

<400> SEQUENCE: 256
aggcaagaug cuggcauagc ug                                              22

<210> SEQ ID NO 257
<211> LENGTH: 22
<212> TYPE: RNA
<213> ORGANISM: Artificial Sequence
<220> FEATURE:
<223> OTHER INFORMATION: synthetic miRNA mmu-miR-345

<400> SEQUENCE: 257
gcugaccccu aguccagugc uu                                              22

<210> SEQ ID NO 258
<211> LENGTH: 23
<212> TYPE: RNA
<213> ORGANISM: Artificial Sequence
<220> FEATURE:
<223> OTHER INFORMATION: synthetic miRNA mmu-miR-34c

<400> SEQUENCE: 258
aggcagugua guuagcugau ugc                                             23

<210> SEQ ID NO 259
<211> LENGTH: 24
<212> TYPE: RNA
<213> ORGANISM: Artificial Sequence
<220> FEATURE:
<223> OTHER INFORMATION: synthetic miRNA mmu-miR-362-5p

<400> SEQUENCE: 259
aauccuugga accuaggugu gaau                                            24

<210> SEQ ID NO 260
<211> LENGTH: 21
<212> TYPE: RNA
<213> ORGANISM: Artificial Sequence
<220> FEATURE:
<223> OTHER INFORMATION: synthetic miRNA mmu-miR-378 (old mmu-miR-422b)

<400> SEQUENCE: 260
acuggacuug gagucagaag g                                               21

<210> SEQ ID NO 261
<211> LENGTH: 22
<212> TYPE: RNA
<213> ORGANISM: Artificial Sequence
<220> FEATURE:

<223> OTHER INFORMATION: synthetic miRNA mmu-miR-384-3p

<400> SEQUENCE: 261
auuccuagaa auuguucaca au                                        22

<210> SEQ ID NO 262
<211> LENGTH: 22
<212> TYPE: RNA
<213> ORGANISM: Artificial Sequence
<220> FEATURE:
<223> OTHER INFORMATION: synthetic miRNA mmu-miR-409-3p

<400> SEQUENCE: 262
gaauguugcu cggugaaccc cu                                        22

<210> SEQ ID NO 263
<211> LENGTH: 22
<212> TYPE: RNA
<213> ORGANISM: Artificial Sequence
<220> FEATURE:
<223> OTHER INFORMATION: synthetic miRNA mmu-miR-450a-5p

<400> SEQUENCE: 263
uuuugcgaug uguccuaau au                                         22

<210> SEQ ID NO 264
<211> LENGTH: 22
<212> TYPE: RNA
<213> ORGANISM: Artificial Sequence
<220> FEATURE:
<223> OTHER INFORMATION: synthetic miRNA mmu-miR-450b-5p

<400> SEQUENCE: 264
uuuugcagua uguccugaa ua                                         22

<210> SEQ ID NO 265
<211> LENGTH: 22
<212> TYPE: RNA
<213> ORGANISM: Artificial Sequence
<220> FEATURE:
<223> OTHER INFORMATION: synthetic miRNA mmu-miR-452

<400> SEQUENCE: 265
uguuugcaga ggaaacugag ac                                        22

<210> SEQ ID NO 266
<211> LENGTH: 23
<212> TYPE: RNA
<213> ORGANISM: Artificial Sequence
<220> FEATURE:
<223> OTHER INFORMATION: synthetic miRNA mmu-miR-464

<400> SEQUENCE: 266
uaccaaguuu auucgugag aua                                        23

<210> SEQ ID NO 267
<211> LENGTH: 23
<212> TYPE: RNA
<213> ORGANISM: Artificial Sequence
<220> FEATURE:
<223> OTHER INFORMATION: synthetic miRNA mmu-miR-465a-5p

<400> SEQUENCE: 267
uauuuagaau ggcacugaug uga                                       23

```
<210> SEQ ID NO 268
<211> LENGTH: 22
<212> TYPE: RNA
<213> ORGANISM: Artificial Sequence
<220> FEATURE:
<223> OTHER INFORMATION: synthetic miRNA mmu-miR-465b-5p

<400> SEQUENCE: 268
uauuuagaau ggugcugauc ug                                              22

<210> SEQ ID NO 269
<211> LENGTH: 22
<212> TYPE: RNA
<213> ORGANISM: Artificial Sequence
<220> FEATURE:
<223> OTHER INFORMATION: synthetic miRNA mmu-miR-465c-5p

<400> SEQUENCE: 269
uauuuagaau ggcgcugauc ug                                              22

<210> SEQ ID NO 270
<211> LENGTH: 23
<212> TYPE: RNA
<213> ORGANISM: Artificial Sequence
<220> FEATURE:
<223> OTHER INFORMATION: synthetic miRNA mmu-miR-468

<400> SEQUENCE: 270
uaugacugau gugcgugugu cug                                             23

<210> SEQ ID NO 271
<211> LENGTH: 22
<212> TYPE: RNA
<213> ORGANISM: Artificial Sequence
<220> FEATURE:
<223> OTHER INFORMATION: synthetic miRNA mmu-miR-98

<400> SEQUENCE: 271
ugagguagua aguuguauug uu                                              22

<210> SEQ ID NO 272
<211> LENGTH: 22
<212> TYPE: RNA
<213> ORGANISM: Artificial Sequence
<220> FEATURE:
<223> OTHER INFORMATION: synthetic miRNA mmu-miR-99a

<400> SEQUENCE: 272
aacccguaga uccgaucuug ug                                              22

<210> SEQ ID NO 273
<211> LENGTH: 22
<212> TYPE: RNA
<213> ORGANISM: Artificial Sequence
<220> FEATURE:
<223> OTHER INFORMATION: synthetic miRNA mmu-miR-99b

<400> SEQUENCE: 273
cacccguaga accgaccuug cg                                              22

<210> SEQ ID NO 274
<211> LENGTH: 21
<212> TYPE: RNA
<213> ORGANISM: Artificial Sequence
<220> FEATURE:
<223> OTHER INFORMATION: synthetic miRNA old mmu-miR-422b
```

```
<400> SEQUENCE: 274
cuggacuugg agucagaagg c                                              21

<210> SEQ ID NO 275
<211> LENGTH: 22
<212> TYPE: RNA
<213> ORGANISM: Artificial Sequence
<220> FEATURE:
<223> OTHER INFORMATION: synthetic miRNA miR-291a-5p

<400> SEQUENCE: 275
caucaaagug gaggcccucu cu                                             22

<210> SEQ ID NO 276
<211> LENGTH: 22
<212> TYPE: RNA
<213> ORGANISM: Artificial Sequence
<220> FEATURE:
<223> OTHER INFORMATION: synthetic miRNA miR-130b

<400> SEQUENCE: 276
cagugcaaug augaaagggc au                                             22

<210> SEQ ID NO 277
<211> LENGTH: 15
<212> TYPE: RNA
<213> ORGANISM: Artificial Sequence
<220> FEATURE:
<223> OTHER INFORMATION: synthetic miRNA seed sequence motif

<400> SEQUENCE: 277
uuaaagcacu uaaau                                                     15

<210> SEQ ID NO 278
<211> LENGTH: 22
<212> TYPE: DNA
<213> ORGANISM: Artificial Sequence
<220> FEATURE:
<223> OTHER INFORMATION: synthetic quantitative real-time PCR primer
      Rex1

<400> SEQUENCE: 278
gattgtggag ccatacattg ca                                             22

<210> SEQ ID NO 279
<211> LENGTH: 18
<212> TYPE: DNA
<213> ORGANISM: Artificial Sequence
<220> FEATURE:
<223> OTHER INFORMATION: synthetic quantitative real-time PCR primer
      Rex1

<400> SEQUENCE: 279
tgccgtagcc tcgcttgt                                                  18

<210> SEQ ID NO 280
<211> LENGTH: 22
<212> TYPE: DNA
<213> ORGANISM: Artificial Sequence
<220> FEATURE:
<223> OTHER INFORMATION: synthetic quantitative real-time PCR primer
      Nanog

<400> SEQUENCE: 280
gctcagcacc agtggagtat cc                                             22
```

<210> SEQ ID NO 281
<211> LENGTH: 22
<212> TYPE: DNA
<213> ORGANISM: Artificial Sequence
<220> FEATURE:
<223> OTHER INFORMATION: synthetic quantitative real-time PCR primer Nanog

<400> SEQUENCE: 281
tccagatgcg ttcaccagat ag                                              22

<210> SEQ ID NO 282
<211> LENGTH: 23
<212> TYPE: DNA
<213> ORGANISM: Artificial Sequence
<220> FEATURE:
<223> OTHER INFORMATION: synthetic quantitative real-time PCR primer Endogenous Oct4

<400> SEQUENCE: 282
tctttccacc aggcccccgg ctc                                             23

<210> SEQ ID NO 283
<211> LENGTH: 23
<212> TYPE: DNA
<213> ORGANISM: Artificial Sequence
<220> FEATURE:
<223> OTHER INFORMATION: synthetic quantitative real-time PCR primer Endogenous Oct4

<400> SEQUENCE: 283
tgcgggcgga catggggaga tcc                                             23

<210> SEQ ID NO 284
<211> LENGTH: 23
<212> TYPE: DNA
<213> ORGANISM: Artificial Sequence
<220> FEATURE:
<223> OTHER INFORMATION: synthetic quantitative real-time PCR primer Endogenous Sox2

<400> SEQUENCE: 284
tagagataga ctccgggcga tga                                             23

<210> SEQ ID NO 285
<211> LENGTH: 23
<212> TYPE: DNA
<213> ORGANISM: Artificial Sequence
<220> FEATURE:
<223> OTHER INFORMATION: synthetic quantitative real-time PCR primer Endogenous Sox2

<400> SEQUENCE: 285
ttgccttaaa caagaccacg aaa                                             23

<210> SEQ ID NO 286
<211> LENGTH: 20
<212> TYPE: DNA
<213> ORGANISM: Artificial Sequence
<220> FEATURE:
<223> OTHER INFORMATION: synthetic quantitative real-time PCR primer Endogenous Klf4

<400> SEQUENCE: 286
gaattgtgtt tcgatgatgc                                                 20

```
<210> SEQ ID NO 287
<211> LENGTH: 23
<212> TYPE: DNA
<213> ORGANISM: Artificial Sequence
<220> FEATURE:
<223> OTHER INFORMATION: synthetic quantitative real-time PCR primer
      Endogenous Klf4

<400> SEQUENCE: 287
tcgcttcctc ttcctccgac aca                                            23

<210> SEQ ID NO 288
<211> LENGTH: 20
<212> TYPE: DNA
<213> ORGANISM: Artificial Sequence
<220> FEATURE:
<223> OTHER INFORMATION: synthetic quantitative real-time PCR primer
      Lin28

<400> SEQUENCE: 288
agtctgccaa gggtctggaa                                                20

<210> SEQ ID NO 289
<211> LENGTH: 22
<212> TYPE: DNA
<213> ORGANISM: Artificial Sequence
<220> FEATURE:
<223> OTHER INFORMATION: synthetic quantitative real-time PCR primer
      Lin28

<400> SEQUENCE: 289
cgctcactcc caatacagaa ca                                             22

<210> SEQ ID NO 290
<211> LENGTH: 20
<212> TYPE: DNA
<213> ORGANISM: Artificial Sequence
<220> FEATURE:
<223> OTHER INFORMATION: synthetic quantitative real-time PCR primer
      Exogenous Oct4

<400> SEQUENCE: 290
tctcccatgc attcaaactg                                                20

<210> SEQ ID NO 291
<211> LENGTH: 20
<212> TYPE: DNA
<213> ORGANISM: Artificial Sequence
<220> FEATURE:
<223> OTHER INFORMATION: synthetic quantitative real-time PCR primer
      Exogenous Oct4

<400> SEQUENCE: 291
cttttatttt atcgtcgacc                                                20

<210> SEQ ID NO 292
<211> LENGTH: 20
<212> TYPE: DNA
<213> ORGANISM: Artificial Sequence
<220> FEATURE:
<223> OTHER INFORMATION: synthetic quantitative real-time PCR primer
      Exogenous Klf4

<400> SEQUENCE: 292
ccttacacat gaagaggcac                                                20

<210> SEQ ID NO 293
```

```
<211> LENGTH: 20
<212> TYPE: DNA
<213> ORGANISM: Artificial Sequence
<220> FEATURE:
<223> OTHER INFORMATION: synthetic quantitative real-time PCR primer
      Exogenous Klf4

<400> SEQUENCE: 293
cttttatttt atcgtcgacc                                              20

<210> SEQ ID NO 294
<211> LENGTH: 20
<212> TYPE: DNA
<213> ORGANISM: Artificial Sequence
<220> FEATURE:
<223> OTHER INFORMATION: synthetic quantitative real-time PCR primer
      Exogenous Sox2

<400> SEQUENCE: 294
ctgcccctgt cgcacatgtg                                              20

<210> SEQ ID NO 295
<211> LENGTH: 20
<212> TYPE: DNA
<213> ORGANISM: Artificial Sequence
<220> FEATURE:
<223> OTHER INFORMATION: synthetic quantitative real-time PCR primer
      Exogenous Sox2

<400> SEQUENCE: 295
cttttatttt atcgtcgacc                                              20

<210> SEQ ID NO 296
<211> LENGTH: 24
<212> TYPE: DNA
<213> ORGANISM: Artificial Sequence
<220> FEATURE:
<223> OTHER INFORMATION: synthetic quantitative real-time PCR primer
      cMyc

<400> SEQUENCE: 296
cagaggagga acgagctgaa gcgc                                         24

<210> SEQ ID NO 297
<211> LENGTH: 28
<212> TYPE: DNA
<213> ORGANISM: Artificial Sequence
<220> FEATURE:
<223> OTHER INFORMATION: synthetic quantitative real-time PCR primer
      cMyc

<400> SEQUENCE: 297
ttatgcacca gagtttcgaa gctgttcg                                     28

<210> SEQ ID NO 298
<211> LENGTH: 22
<212> TYPE: DNA
<213> ORGANISM: Artificial Sequence
<220> FEATURE:
<223> OTHER INFORMATION: synthetic quantitative real-time PCR primer
      RPL7 input control

<400> SEQUENCE: 298
gattgtggag ccatacattg ca                                           22

<210> SEQ ID NO 299
<211> LENGTH: 18
```

```
<212> TYPE: DNA
<213> ORGANISM: Artificial Sequence
<220> FEATURE:
<223> OTHER INFORMATION: synthetic quantitative real-time PCR primer
      RPL7 input control

<400> SEQUENCE: 299
tgccgtagcc tcgcttgt                                                   18
```